US007964400B2

(12) United States Patent
Ralph

(10) Patent No.: US 7,964,400 B2
(45) Date of Patent: Jun. 21, 2011

(54) IMMUNE POTENTIATING COMPOSITIONS OF CANCER CELLS

(75) Inventor: Stephen John Ralph, Brighton (AU)

(73) Assignee: Stephen John Ralph, Mermaid Waters QLD (AU)

( * ) Notice: Subject to any disclaimer, the term of this patent is extended or adjusted under 35 U.S.C. 154(b) by 183 days.

(21) Appl. No.: 12/259,194

(22) Filed: Oct. 27, 2008

(65) Prior Publication Data

US 2009/0081792 A1    Mar. 26, 2009

Related U.S. Application Data

(62) Division of application No. 10/276,642, filed as application No. PCT/AU01/00565 on May 17, 2001, now Pat. No. 7,455,846.

(30) Foreign Application Priority Data

May 17, 2000  (AU) .................................. PQ7553

(51) Int. Cl.
    *C12N 5/00*         (2006.01)
(52) U.S. Cl. ........................................ 435/375
(58) Field of Classification Search .................. None
    See application file for complete search history.

(56) References Cited

U.S. PATENT DOCUMENTS

| 5,711,425 | A | 1/1998 | Trimble-Gomez et al. |
| 5,858,776 | A | 1/1999 | Ostrand-Rosenberg et al. |
| 5,993,828 | A | 11/1999 | Morton |
| 6,039,941 | A | 3/2000 | Blankenstein et al. |
| 6,183,734 | B1 | 2/2001 | Chen et al. |
| 6,207,170 | B1 | 3/2001 | Popescu et al. |
| 6,218,371 | B1 | 4/2001 | Krieg et al. |
| 6,277,368 | B1 | 8/2001 | Hiserodt et al. |
| 6,319,709 | B1 | 11/2001 | Ostrand-Rosenberg et al. |
| 6,451,305 | B1 | 9/2002 | Boussiotis et al. |
| 6,828,150 | B2 | 12/2004 | Cai et al. |
| 7,011,833 | B1 | 3/2006 | Sturmhoefel et al. |
| 7,455,846 | B2 * | 11/2008 | Ralph ........................ 424/277.1 |
| 2001/0012517 | A1 | 8/2001 | Popescu et al. |
| 2002/0034500 | A1 | 3/2002 | Levings et al. |
| 2002/0155135 | A1 | 10/2002 | Popescu et al. |
| 2003/0092177 | A1 | 5/2003 | Belardelli et al. |

FOREIGN PATENT DOCUMENTS

| EP | 1067194 | 1/2001 |
| EP | 1291414 | 3/2003 |
| WO | WO 94/21808 | 9/1994 |
| WO | WO 97/00085 | 1/1997 |
| WO | WO 98/23728 | 6/1998 |
| WO | WO 99/15199 | 4/1999 |
| WO | WO 99/61051 | 12/1999 |
| WO | WO 00/04918 | 2/2000 |
| WO | WO 00/31138 | 6/2000 |
| WO | WO 00/44880 | 8/2000 |
| WO | WO 01/15728 | 3/2001 |
| WO | WO 01/95919 | 12/2001 |
| WO | WO 02/36769 | 5/2002 |
| WO | WO 03/045427 | 6/2003 |

OTHER PUBLICATIONS

Denfeld, R.W. et al. 1995 "In Situ Expression of B7 and CD28 Receptor Families in Human Malignant Melanoma: Relevance for T-Cell-Mediated Anti-Tumor Immunity" *Int. J. Cancer* 62:259-265.
Morandini, R. et al. 1998 "Modulation of ICAM-1 Expression by α-MSH in Human Melanoma Cells and Melanocytes" *Journal of Cellular Physiology* 175:276-282.
Abril et al.,(1998) "Unresponsiveness to interferon associated with STAT1 protein deficiency in a gastric adenocarcinoma cell line," *Cancer Immunol. Immunother* 47:113-120.
Allison et al. 1995 "Manipulation of costimulatory signals to enhance antitumor T-cell responses" *Current Opinion in Immunology* 7:682-686.
Aman et al., (1990) "An Epstein-Barr virus immortalization associated gene segment interferes specifically with the IFN-induced antiproliferative response in human B-lymphoid cell lines," *EMBO* 9:147-152.
Attwood, T. 2000 "Genomics. The Babel of bioinformatics" *Science* 290:471-473.
Baltz, J., (1995) "Vaccines in the treatment of cancer," *Am. J. Health-Syst. Phar.*, 52:2574-2585.
Billard et al., (1986) "Treatment of hairy cell leukemia with recombinant alpha interferon: II. In vivo down-regulation of alpha interferon receptors on tumor cells," *Blood* 67: 821-826.
Bohm et al., (1998) "T cell-mediated, IFN-γ-facilitated rejection of murine B16 melanomas[1]", *J. Immunol.* 161:897-908.
Bowie et al. 1990 "Deciphering the message in protein sequences: tolerance to amino acid substitutions" *Science* 247:1306-1310.
Cavallo et al., (1995) "Co-expression of B7-1 and ICAM-1 on tumors is required for rejection and the establishment of a memory response," *Eur. J. Immunol.* 25:1154-1162.
Chen et al., (1993) "Costimulation of T cells for tumor immunity," *Immunol Today* 14: 483-485.
Chen et al., (1994) "Tumor immunogenicity determines the effect of B7 costimulation on T cell-mediated tumor immunity," *J. Exp. Med.* 179:523-532.
Chin et al., (1996) "Cell growth arrest and induction. of cyclin-dependent kinase inhibitor $p21^{WAF1/CIP1}$ mediated by STAT1," *Science* 272:719-722.
Chin et al., (1997) "Activation of the STAT signaling pathway can cause expression of caspase 1 and apoptosis," *Mol. Cell. Biol.* 17: 5328-5337.
Colamonici et al., (1992) "Correlation between interferon (IFN) α resistance and deletion of the IFN α/β genes in acute leukemia cell lines suggests selection against the IFN system," *Blood* 80: 744-749.

(Continued)

*Primary Examiner* — Ilia Ouspenski
(74) *Attorney, Agent, or Firm* — Knobbe, Martens, Olson & Bear, LLP

(57) ABSTRACT

A composition of matter is disclosed, comprising an immunostimulatory molecule and animal cells cultured in the presence of at least one interferon (IFN) for a time and under conditions sufficient to enhance the antigen presenting function of said cells. Also disclosed are immunopotentiating compositions and their use for treatment and/or prophylaxis of a disease or condition.

58 Claims, 17 Drawing Sheets

OTHER PUBLICATIONS

Coligan, J.E. et al., (1993) "In vitro assays for mouse lymphocyte function," Chapt. 3 in *Current Protocols in Immunology*, Edited by Coligan et al., Greene Pub. Associates and Wiley-Interscience, New York. 3.0.1-3.15.12.

De Maeyer et al., (1988) "Induction of IFN-α and IFN-β", Chapter 3 of *Interferons and other regulatory cytokines*, John Wiley & Sons, New York, New York, pp. 39-66.

De Maeyer et al., (1988) "The effects of interferons on cell growth and division", Chapter 7 of *Interferons and other regulatory cytokines*, John Wiley & Sons, New York, New York, pp. 134-153.

De Maeyer et al., (1988) "The effects of interferons on tumor cells", Chapter 14 of *Interferons and other regulatory cytokines*, John Wiley & Sons, New York, New York, pp. 334-363.

Dezfouli, S. et al. (2003) "Enhancing CTL responses to melanoma cell vaccines in vivo:synergistic increases obtained using IFNgamma primed and IFNbeta treated B7-1+B16-F10 melanoma cells" Immunology and Cell Biology 81:459-471.

Dols et al., (2003) "Allogeneic breast cancer cell vaccines," *Clin. Breast Cancer Suppl.* 3: 173-180.

Dron et al., (1993) "Interferon-resistant Daudi cells are deficient in interferon-α-induced ISGF3α activation, but remain sensitive to the interferon-α-induced increase in ISGF3γ content," *J. Interferon Res.* 13:377-383.

Gao, P.Q et al. (1993) "Interferon-gamma priming effects in the activation and deactivation of ISGF3 in K562 cells" Journal of Biological Chemistry 268:12380-12387.

Greenwand et al. 2005 "The B7 Family Revisited" *Annu Rev Immunol* 23:515-548.

Guadagni, F. et al. (1989) "Selective interferon-induced enhancement of tumor-associated antigens on a spectrum of freshly isolated human adenocarcinoma cells" Journal of the National Cancer Institute 81:502-512.

Guo et al. 1994 "Effective tumor vaccine generated by fusion of hepatoma cells with activated B cells" *Science* 263:518-520.

Gutterman, J. (1994) "Cytokine therapeutics: lessons from interferon α," *PNAS USA.*, 91:1198-1205.

Haque et al., (1998) "Signal transduction in the interferon system," *Semin. Oncol.* 25:14-22.

Hersey et al., (1994) "Expression of the co-stimulatory molecule B7 on melanoma cells," *Int. J. Cancer* 58:527-532.

Hertzog et al., (1988) "Interferons in rheumatoid arthritis: alterations in production and response related to disease activity," *Clin. Immunol. Immunopathol.*, 48:192-201.

Heyman et al., (1994) "Interferon system defects in malignant T-cells," *Leukemia* 8:425-434.

Honglian et al., "Induction of anti-hepatoma immunity by recombinant retrovirus expressing B7-1/B7-2 costimulatory molecules", *J Med Coll PLA*, vol. 15(2), 2000: pp. 138-142.

Hsueh et al., (2002) "Active immunotherapy by reinduction with a polyvalent allergeneic cell vaccine correlates with improved survival in recurrent monastic melanoma," *Ann Surg Oncol* 9: 486-492.

Isaacs et al., (1957) "Virus interference. I. The interferon," *Proc. R. Soc. Lond. (Biol.)* 147:258-267.

Johns et al., (1992) "Antiproliferative potencies of interferons on melanoma cell lines and xenografts: higher efficacy of interferon β," *J. Natl. Cancer Inst.* 84:1185-1120.

Kanda et al., (1992) "The EBNA2-related resistance towards alpha interferon (IFN-α) in Burkitt's lymphoma cells effects induction of IFN-induced genes but not the activation of transcription factor ISGF-3," *Mol. Cel. Biol.* 12:4930-4936.

Kaplan et al., (1998) "Demonstration of an interferon γ-dependent tumor surveillance system in immunocompetent mice," *PNAS USA* 95:7556-7561.

Kim et al., "Therapeutic anti-tumor response induced with epitope-pulsed fibroblasts genetically engineered for b7.1 expression and IFN-γ sectertion", *Int. J. Cancer*, vol. 87, 2000: pp. 427-433.

Kolla et al., (1996) "Modulation of interferon (IFN)-inducible gene expression by retinoic acid. Up regulation of STAT1 protein in IFN-unresponsive cells," *J. Biol. Chem.* 271:10508-10514.

Kuniyasu et al., (1997) "Growth inhibitory effect of interferon-β is associated with the induction of cyclin-dependent kinase inhibitor p27$^{Kip1}$ in a human gastric carcinoma cell line," *Cell Growth Differ.* 8:47-52.

Lasek et al., "Antitumor effects of the combination therapy with TNF-α gene-modified tumor cells and interleukin 12 in a melanoma model in mice", *Cancer Gene Therapy*, vol. 7, No. 12, 2000: pp. 1581-1590.

Lehtonen et al., (1997) "Interferons up-regulate STAT1, STAT2 and IFR family transcription factor gene expression in human peripheral blood mononuclear cells and macrophages," *J. Immunol.* 159:794-803.

Levy et al., (1989) "Cytoplasmic activation of ISGF3, the positive regulator of interferon-α-stimulated transcription, reconstituted in vitro," *Genes & Dev.* 3:1362-1371.

Lin et al., "Considerations Regarding the Use of Cytokines in Active Specific Immunotherapy of Cancer", *Vaccine Research*, vol. 5, No. 1, 1996: pp. 41-48.

Martin-Fontecha et al., (1996) "Heterogeneous effects of B7-1 and B7-2 in the induction of both protective and therapeutic anti-tumor immunity against different mouse tumors," *Eur. J. Immunol.* 26:1851-1859.

Mashko et al., (1990) "TGATG vector: a new expression system for cloned foreign genes in *Escherichia coli* cells," *Gene* 88:121-126.

McAdam et al., (1998) "The role of B7 co-stimulation in activation and differentiation of CD4+ and CD8+ T cells," *Immunol. Rev.* 165:231-247.

Meyer et al., "Potential of CD80-transfected human breast carcinoma cells to induce peptide-specific T lymphocytes in an allogeneic human histocompatibility leukocyte antigens (HLA)-A2.1+-matched situation", *Cancer Gene Therapy*, vol. 6, No. 3, 1999: pp. 282-288.

Nociari et al., (1998) "A novel one-step, highly sensitive fluorometric assay to evaluate cell-mediated cytotoxicity," *J. Immuno. Methods* 213:157-167.

Perou et al., (1999) "Distinctive gene expression patterns in human mammary epithelial cells and breast cancers," *PNAS USA* 96:9212-9217.

Pestka et al., (1987) "Interferons and their actions," *Annu. Rev. Biochem.* 56:727-777.

Pfeffer et al., (1990) "The down-regulation of α-interferon receptors in human lymphoblastoid cells: relation to cellular responsiveness to the antiproliferative action of α-interferon," *Cancer Research* 50:2654-2657.

Prehn, R., (1996) "On the probability of effective anticancer vaccines," *The Cancer Journal* 8:1-4.

Ralph et al., (1998) "Revising interferons—prodigies among the cytokines," *Today's Life Science* 10:37-43.

Ramarathinam et al., (1994) "T cell costimulation by B7/BB1 induces CD8 T cell-dependent tumor rejection: an important role of B7/BB1 in the induction, recruitment, and effector function of anti-tumor t cells," *J. Exp. Med.* 179:1205-1214.

Sims et al., (1993) "A novel interferon-inducible domain: structural and functional analysis of the human interferon regulatory factor 1 gene promoter," *Mol. Cell. Biol.* 13: 690-702.

Skolnick et al. 2000 "From genes to protein structure and function: novel applications of computational approaches in the genomic era" *Trends in Biotech* 18:34-39.

Stark et al., (1998) "How cells respond to interferons," *Annu. Rev. Biochem.* 67:227-264.

Subiza et al., (1995) "Prospects in cancer vaccines," *The Cancer Journal* 8:293-298.

Sun et al., (1998) "Interferon-α resistance in a cutaneous t-cell lymphoma cell line is associated with lack of STAT1 expression," *Blood* 91:570-576.

Wilks et al., (1994) "Cytokine signal transduction and the jak family of protein tyrosine kinases," *BioEssays* 16:313-320.

Wines et al., (1993) "A colourimetric dye assay to detect anti-viral activity of interferons: sensitivity for measuring cellular responsiveness to interferons," *Biochem. Mol. Biol. Int.* 31:1111-1190.

Wong et al., (1997) "Interferon-resistant human melanoma cells are deficient in ISGF3 components, STAT1, STAT2, and p48-ISGFEγ" *J. Biol. Chem.* 272(45):28779-28785.

Wong et al., (1998) "IFN-γ priming up-regulates IFN-stimulated gene factor 3 (ISGF3) components, augmenting responsiveness of IFN-resistant melanoma cells to type I IFNs," *J. Immunol.*, 160:5475-5484.

Xu et al., (1994) "Primary leukemia cells resistant to α-interferon in vitro are defective in the activation of the DNA-binding factor interferon-stimulated gene factor 3," *Blood* 84:1942-1949.

\* cited by examiner

MHC Class I surface levels

A:

B:

............ background fluorescence
———— no Interferon
- - - - + Interferon

| Cell line | fold increase in mean fluorescence levels of B7-1 standardised to B16 wild type |
|---|---|
| B16 wild type | 1 |
| B16B7-1Medium | 4 |
| B16B7-1High | 30 |

A:

B:

C:

......... background fluorescence
——— no Interferon
——— + Interferon

IMMUNE POTENTIATING COMPOSITIONS OF CANCER CELLS

CROSS-REFERENCE TO RELATED APPLICATIONS

This application is a divisional of application Ser. No. 10/276,642, filed Jun. 30, 2003, which is a U.S. National Phase of International Application No. PCT/AU01/00565, filed May 17, 2001, which claims the benefit of Australian Patent Application AU PQ7553, filed May 17, 2000, all of which are hereby expressly incorporated by reference in their entireties.

FIELD OF THE INVENTION

This invention relates generally to immune potentiating compositions. More particularly, the present invention is directed to compositions of matter comprising cells exhibiting enhanced antigen presenting functions. The compositions of the present invention are generally useful in facilitating the stimulation of host immune cell responses, including selective and targeted immune cell responses. The compositions of the present invention are particularly useful in the treatment and/or prophylaxis of cancers and tumours.

BACKGROUND OF THE INVENTION

Bibliographic details of the publications numerically referred to in this specification are collected at the end of the description.

The interferons (IFNs) comprise a group of glycoproteins produced by various cells in response to viral infections, specific antigens or mitogens. Since their discovery (1), the IFNs have been found to play important roles in, for example, antiviral, anti-proliferative, differentiative and immunomodulatory responses (2).

Following binding of IFNs to their receptor, intracellular tyrosine kinases of the JAK family become activated and phosphorylate transcription factor molecules called Stats (Signal transducers and activators of transcription). IFN-gamma signals by activating the formation of a homodimer of Stat 1. IFN-alpha or beta mainly signal by activating the interferon sensitive gene factor 3 (ISGF3), a complex of Stat1 and/or Stat2, as homo or heterodimers that combine to produce trimeric molecules containing a third protein, p48 ISGF3-gamma. After activation, the transcription factor complexes migrate to the nucleus, binding to target DNA sequences thereby affecting the expression of interferon sensitive genes (ISGs). The Stat1 homodimer binds a sequence TTCNNNGAA, known as the GAS site. IFN signalling also activates one other interferon regulator factor, IRF-1. Both factors, IRF-1 and ISGF3 bind via regulatory response elements in the promoter regions of ISGs that comprise direct repeats of the DNA sequence GAAANN, leading to activation of transcription from the IGS (for reviews, see (3, 4)).

The genes encoding IFNs and components of the IFN signalling pathway are proposed to belong to a family of tumour suppressor genes (5). Accordingly, mutations disrupting any steps in the IFN signal transduction pathway would be expected to reduce cellular responsiveness to IFN, abrogating the tumour suppressive function of IFN action and thereby facilitating the onset of cancer.

The effect of IFN in the treatment of advanced malignant melanoma has been demonstrated in several clinical trials. In this regard, IFN-alpha is effective in only a group (~23%) of skin melanoma patients. An explanation was proposed for this phenomenon based on abnormalities detected in the IFN signalling properties of melanoma cells (6-8). Studies on growth of short-term cultures at low passage number established from advanced stage III metastatic melanomas revealed all patients' samples to be resistant to IFN when compared to IFN-sensitive melanoma cell lines and melanocytes (6). As a result, the majority of patients with advanced metastatic melanomas will fail to respond significantly to IFNs because their tumour cells fail to adequately respond to the direct actions of the IFNs. IFNs act in vivo in two ways to either indirectly stimulate immune effector cells or directly act on the tumour cell targets (9). Studies of tumour cell lines produced in knockout mice which have been made IFN-insensitive (by using either Stat1-deficient or IFN-gamma receptor-deficient mice) have revealed that the direct effects of IFN are important for immune surveillance (10). Cancer cells established in the IFN-gamma insensitive mice, when passaged into syngeneic wild type mice, were no longer rejected by the immune system. Thus, it was concluded that IFN action was mediated in part through its direct effects on the tumour cells, presumably by inducing enhanced tumour cell immunogenicity (10). Thus, loss of responsiveness to IFNs as tumour suppressors is one of the early and important developments in the onset of malignancy as it allows tumours to evade immune surveillance, providing the tumours with a significant survival advantage.

Many studies have reported various defects in the IFN system as being responsible for the different sensitivities to type I IFNs in cell lines established from other tumour types: (i) IFN-alpha/-beta gene deletion in acute leukaemia cell lines (11) and malignant T cells (12); (ii) alteration or down regulation of IFN-alpha receptor gene expression in hairy cell leukaemia (13) and lymphoblastoid cells (14); (iii) interference with the induction of the expression of IFN-stimulated genes in B lymphoid cell lines (15) and Burkitt's lymphoma cells (16); (iv) defects in the activation of transcription factors in Daudi cells (17) and primary leukaemia cells (18). In addition, melanoma cell lines with a wide variation in their responsiveness to the anti-proliferative (19) and antiviral (20) activities of IFNs, ranging from highly sensitive to relatively resistant, have been described.

Initial studies by the present inventors on IFN signalling in melanoma cell lines with different responsiveness to IFN revealed that these cell lines did not show significant differences in the levels of IFN binding to cell surface receptors (21) or in the activation of the IFN receptor associated JAK tyrosine kinases (7). Thus, loss of IFN responsiveness did not appear to be due to abnormalities in the IFN mediated activation of receptor signalling. However, in all IFN-resistant melanoma cells examined, deficiencies were detected at the next level in the IFN activated signalling pathways (6). In this regard, much lower intracellular levels of the trans-activating relay factors essential for transmitting the IFN signal from the membrane to the cell nucleus were detected [for review, see 8]. Hence, changes in gene expression normally induced by IFNs and which are essential if tumours are to be recognized and eliminated by the body's immune system will not occur in the IFN-resistant tumour cells because the signal reaching the nucleus is insufficient.

Cellular responsiveness to IFNs can be increased by prior treatment with IFN (22). This process, called "priming" (6), increases the levels of the cognate transcription factors, including IRF-1 and all three components of ISGF3: Stat1; Stat2; and p48. Regulation of the IRF-1, Stat2 and p48 promoters have been described (for example, see (23) and expression of these genes is regulated by the IFNs. Stat1 protein is involved in activating expression of IRF-1, p48 and Stat2.

Stat1 is at a pivotal point in IFN signalling as it is required for both type I and II IFN receptor signals (3). The regulation of Stat1 activity has become an important biological question for other reasons as well, given other key roles for Stat1 in important cell functions. Thus, IFNs act via Stat1 to regulate cell growth by directly inducing expression of the cell cycle inhibitor, CKI p21 WAF (24, 25). In addition, Stat1 regulates expression of caspases 1, 2 and 3 involved in apoptosis (26).

In work leading up to the present invention, the inventors' analyses of human melanoma cells revealed that Stat1 (6, 7) and IRF-1 were consistently deficient in IFN-resistant melanoma cells. In particular, the evidence pointed to a key role for the transcription factor, Stat1, which was poorly expressed at the mRNA and protein levels in IFN-resistant cells and moreover, responsiveness to IFN was greatly increased by transfecting IFN-resistant melanoma cells to express increased levels of Stat1 (6). Similar results have been shown to occur in breast cancer cell samples as well (27, 28) raising the possibility of a more widespread problem, which highlights the broader significance of Stat1 deficiency to cancers in general. Consistent with this hypothesis, several studies have since reported other cancer types in which Stat1 deficiencies have been commonly noted (29, 30).

The present inventors also found that by treating melanoma cells with high levels of IFN-gamma (gamma-priming), the treated cells express markedly increased levels of Stat1 as well as of p48 and Stat2 (6). Even in type I IFN-resistant melanoma cells, Stat1 levels were increased after gamma-priming. In addition, the cellular responsiveness to treatment with type I IFN was increased after gamma-priming, including significantly greater ISGF3 binding activity detected by electrophoretic gel mobility shift assay (EMSA) and increased induction of ISGs detected by immunochemical methods. Amongst the ISGs whose expression was increased were the IFN inducible surface antigens, class I MHC and ICAM-1 (6), which are important in immune cell recognition of tumour cells.

SUMMARY OF THE INVENTION

The present inventors have surprisingly discovered that a stronger immune response against a cancer can be elicited by vaccination with a composition comprising interferon treated cancer cells in combination with an immunostimulatory molecule that is either present on the surface of the cancer cells or in soluble form. The combination of interferon treatment and immunostimulatory molecule produces a synergistic enhancement in antigen presenting function of the treated cells, which when introduced into a suitable host, elicit a markedly improved stimulation of the immune response against antigens presented by those cells. The above discovery has been reduced to practice in the form of compositions of matter, kits, assays and methods of treatment, as described hereinafter.

Thus, in one aspect of the present invention, there is provided a composition of matter comprising an immunostimulatory molecule and animal cells cultured in the presence of a type II interferon (IFN) in exogenous form and at least one type I IFN in exogenous form for a time and under conditions sufficient to enhance the antigen presenting function of said cells, wherein said animal cells have been washed to remove said IFNs.

In a preferred embodiment, the type II IFN is present in the culture medium at a concentration of about 100 to about 2000 international units/mL.

In another preferred embodiment, the type I IFN is present in the culture medium at a concentration of about 100 to about 2000 international units/mL.

The immunostimulatory molecule can be present on the surface of said cells or in soluble form.

The animal cells are preferably cancer or tumour cells. Suitably, the cancer or tumour cells include, but are not restricted to, melanoma cells and mammary carcinoma cells.

In another aspect of the present invention, there is provided a method for enhancing immunopotentiation of animal cells, comprising:

culturing animal cells expressing an immunostimulatory membrane molecule in the presence of a type II interferon (IFN) in exogenous form and at least one type I IFN in exogenous form for a time and under conditions sufficient to enhance the antigen presenting functions of said cells; and washing said cells to remove said IFNs.

Preferably, the method further comprises isolating cells expressing said immunostimulatory membrane molecule from a heterogeneous population of animal cells.

The method may further comprise modifying the animal cells to express said immunostimulatory membrane molecule.

Preferably, the step of modification comprises introducing into said animal cells a polynucleotide from which the immunostimulatory membrane molecule can be expressed.

Suitably, the animal cells are cultured by contacting said cells with a type II IFN for a time and under conditions sufficient to permit cellular responsiveness to at least one type I IFN and then contacting said cultured cells with the at least one type I IFN for a time and under conditions sufficient to enhance the antigen presenting function of said cells.

Preferably, the type II IFN is selected from the group consisting of an IFN-gamma, a biologically active fragment of an IFN-gamma, a variant of an IFN-gamma, a variant of a said biologically active fragment, a derivative of an IFN-gamma, a derivative of a said biologically active fragment, a derivative of a said variant and an analogue of an IFN-gamma.

The at least one type I IFN is preferably selected from the group consisting of an IFN-alpha, an IFN-beta, a biologically active fragment of an IFN-alpha, a biologically active fragment of an IFN-beta, a variant of an IFN-alpha, a variant of an IFN-beta, a variant of a said biologically active fragment, a derivative of an IFN-alpha, a derivative of an IFN-beta, a derivative of a said biologically active fragment, a derivative of a said variant, an analogue of an IFN-alpha and an analogue of an IFN-beta.

Preferably, the method as broadly described above further comprises rendering the animal cells inactive or incapable of proliferation. For example, the animal cells may be irradiated with a suitable amount of radiation such as, for example, gamma-irradiation, as is known in the art, to render the animal cells incapable of proliferating in the intended host.

In yet another aspect, the invention contemplates a method for enhancing immunopotentiation of animal cells, comprising:

culturing animal cells in the presence of a type II interferon (IFN) in exogenous form and at least one type I IFN in exogenous form for a time and under conditions sufficient to enhance the antigen presenting functions of said cells;

washing said cells to remove said IFNs; and combining said cells with an immunostimulatory molecule in soluble form.

Another aspect of the present invention resides in a composition of matter comprising an immunostimulatory molecule and animal cells cultured in the presence of a type II interferon (IFN) in exogenous form and one or both of a first type I IFN in exogenous form and a second type I IFN in exogenous form for a time and under conditions sufficient to enhance the antigen presenting function of said cells, wherein said animal cells have been washed to remove said IFNs, wherein said type II IFN is selected from the group consisting of an IFN-gamma, a biologically active fragment of an IFN-gamma, a variant of an IFN-gamma, a variant of a said biologically active fragment, a derivative of an IFN-gamma, a derivative of a said biologically active fragment, a derivative of a said variant and an analogue of an IFN-gamma, wherein said first type I IFN is selected from the group consisting of an IFN-beta, a biologically active fragment of an IFN-beta, a variant of an IFN-beta, a variant of a said biologically active fragment, a derivative of an IFN-beta, a derivative of a said biologically active fragment, a derivative of a said variant and an analogue of an IFN-beta, and wherein said second type I IFN is selected from the group consisting of an IFN-alpha, a biologically active fragment of an IFN-alpha, a variant of an IFN-alpha, a variant of a said biologically active fragment, a derivative of an IFN-alpha, a derivative of a said biologically active fragment, a derivative of a said variant and an analogue of an IFN-alpha.

In yet another aspect, the invention features a composition of matter comprising an immunostimulatory molecule and animal cells cultured in the presence of a type II interferon (IFN) in exogenous form and a type I IFN in exogenous form for a time and under conditions sufficient to enhance the antigen presenting function of said cells, wherein said animal cells have been washed to remove said IFNs, wherein said type II IFN is selected from the group consisting of an IFN-gamma, a biologically active fragment of an IFN-gamma, a variant of an IFN-gamma, a variant of a said biologically active fragment, a derivative of an IFN-gamma, a derivative of a said biologically active fragment, a derivative of a said variant and an analogue of an IFN-gamma, and wherein said type I IFN is selected from the group consisting of an IFN-beta, a biologically active fragment of an IFN-beta, a variant of an IFN-beta, a variant of a said biologically active fragment, a derivative of an IFN-beta, a derivative of a said biologically active fragment, a derivative of a said variant and an analogue of an IFN-beta.

In another aspect, the invention extends to a composition of matter comprising an immunostimulatory molecule and animal cells cultured in the presence of a type II interferon (IFN) in exogenous form and a type I IFN in exogenous form for a time and under conditions sufficient to enhance the antigen presenting function of said cells, wherein said animal cells have been washed to remove said IFNs, wherein said type II IFN is selected from the group consisting of an IFN-gamma, a biologically active fragment of an IFN-gamma, a variant of an IFN-gamma, a variant of a said biologically active fragment, a derivative of an IFN-gamma, a derivative of a said biologically active fragment, a derivative of a said variant and an analogue of an IFN-gamma, and wherein said type I IFN is selected from the group consisting of an IFN-alpha, a biologically active fragment of an IFN-alpha, a variant of an IFN-alpha, a variant of a said biologically active fragment, a derivative of an IFN-alpha, a derivative of a said biologically active fragment, a derivative of a said variant and an analogue of an IFN-alpha.

In another aspect, the invention contemplates a method for enhancing or otherwise improving the immunogenicity of an antigen, comprising:

providing animal cells cultured in the presence of a type II interferon (IFN) in exogenous form and at least one type I IFN in exogenous form for a time and under conditions sufficient to enhance the antigen presenting functions of said cells, wherein said animal cells have been washed to remove said IFNs; and loading said antigen onto the IFN-treated animal cells.

Suitably, the antigen is of viral, bacterial, fungal, or protozoan origin.

According to another aspect, the invention envisions a composition of matter for eliciting an immune response against a target antigen, comprising animal cells cultured in the presence of a type II interferon (IFN) in exogenous form and at least one type I IFN in exogenous form for a time and under conditions sufficient to enhance the antigen presenting functions of said cells, wherein said animal cells have been washed to remove said IFNs and wherein an antigen corresponding to said target antigen has been loaded onto the IFN-treated animal cells.

In another aspect, the invention resides in a vaccine for stimulating a host's immune system, comprising a composition of matter as broadly described above, said vaccine optionally further comprising one or more pharmaceutically acceptable carriers, adjuvants and/or diluents.

In yet another aspect, the invention provides a method for treatment and/or prophylaxis of a disease or condition, comprising administering to a patient in need of such treatment a therapeutically effective amount of a composition or vaccine as broadly described above.

In one embodiment, said administration comprises administering separately, sequentially or simultaneously to the patient a soluble immunostimulatory molecule and the cultured animal cells.

According to a further aspect, the invention provides a kit comprising a composition of matter including animal cells cultured in the presence of a type II interferon (IFN) in exogenous form and at least one type I IFN in exogenous form for a time and under conditions sufficient to enhance the antigen presenting function of said cells, wherein said animal cells have been washed to remove said IFNs, together with an immunostimulatory molecule.

In a preferred aspect of the invention, there is provided a method for treatment and/or prophylaxis of tumorigenesis, comprising administering to a patient in need of such treatment a therapeutically effective amount of a composition or vaccine as broadly described above.

In a still further aspect, the invention provides a process for assessing the responsiveness of animal cells to treatment with at least one interferon (IFN), comprising detecting in said animal cells the level and/or functional activity of a polypeptide involved in IFN signalling or the level and/or functional activity of a modulatory agent that modulates said polypeptide or the level and/or functional activity of a downstream cellular target of said polypeptide or the level of an expression product of a genetic sequence encoding a member selected from the group consisting of said polypeptide, said modulatory agent and said downstream cellular target.

Preferably, the polypeptide is Stat1.

The invention, in yet another aspect, contemplates the use of a target cell in an assay for detecting cytolytic activity of a cytotoxic T lymphocyte (CTL) for said target cell, wherein said target cell has been cultured in the presence of a type II interferon (IFN) in exogenous form and at least one type I IFN in exogenous form for a time and under conditions sufficient to enhance the antigen presenting function of said target cell, and washed to remove said IFNs.

In one embodiment, said target cell expresses an immunostimulatory membrane molecule. In an alternate embodiment, said target cell is contacted with said CTL in the presence of a soluble immunostimulatory molecule.

Preferably, said CTL is a CD8+ CTL.

In still yet another aspect, the invention features a method for detecting cytolytic T lymphocyte (CTL) mediated lysis of a target cell, comprising:
providing a target cell cultured in the presence of a type II interferon (IFN) in exogenous form and at least one type I IFN in exogenous form for a time and under conditions sufficient to enhance the antigen presenting functions of said target cell, wherein said target cell has been washed to remove said IFNs;
contacting the target cell with a CTL that has cytolytic activity for said target cell; and
detecting CTL-mediated lysis of said target cell.

The invention also encompasses the use of a member selected from the group consisting of an antigen binding molecule that is immuno-interactive with a polypeptide or modulatory agent as broadly described above, and a detector polynucleotide or oligonucleotide that hybridises to said expression product in a kit for assessing the responsiveness of animal cells to treatment with at least one interferon (IFN).

Figure 1:
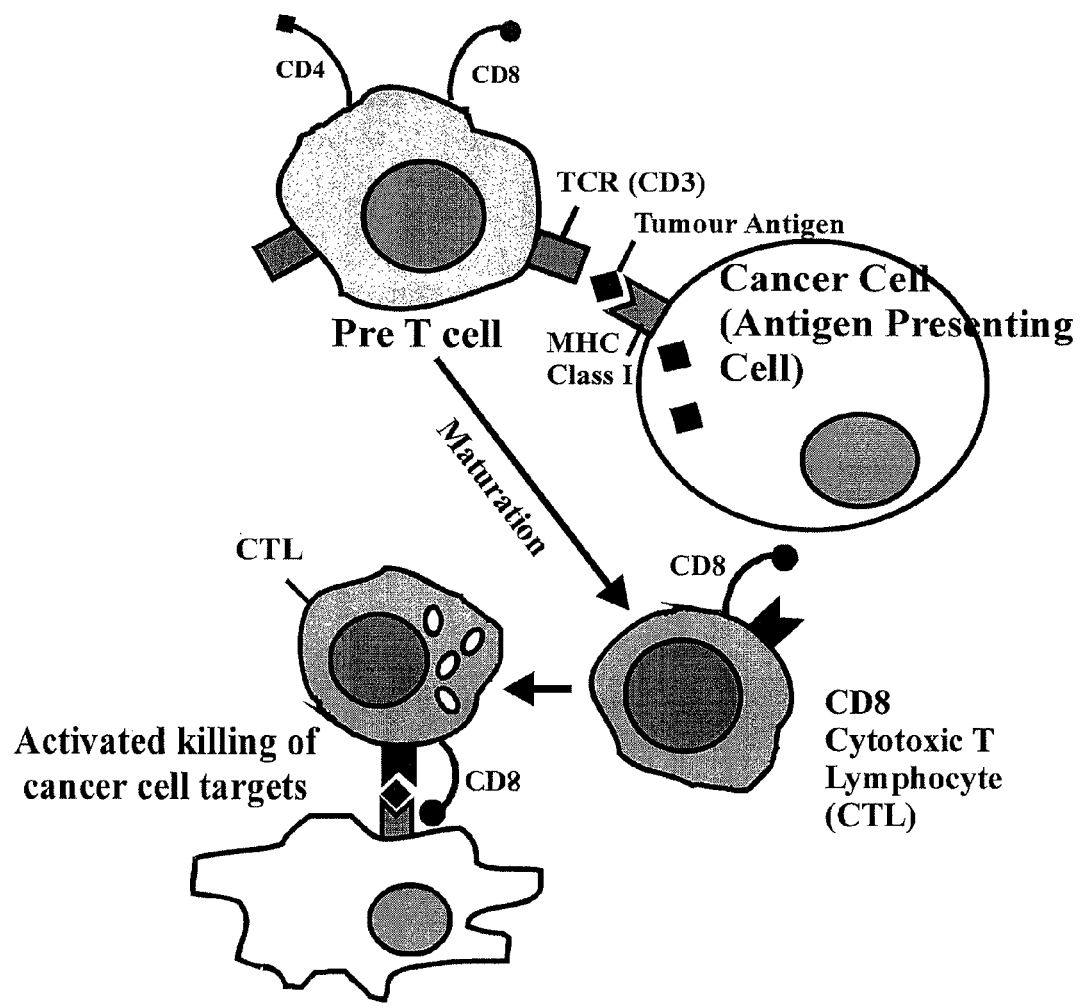
FIG. 1 is a schematic representation showing a cytotoxic T lymphocyte response to a cancer cell.

BRIEF DESCRIPTION OF THE SEQUENCES:
SUMMARY TABLE

TABLE A

| SEQUENCE ID NUMBER | SEQUENCE | LENGTH |
| --- | --- | --- |
| SEQ ID NO: 1 | Full-length human CDS encoding interferon gamma as set forth under GenBank Accession No. J00219 | 501 nts |
| SEQ ID NO: 2 | Polypeptide encoded by SEQ ID NO: 1 | 166 aa |
| SEQ ID NO: 3 | Full-length human CDS encoding interferon beta 1 as set forth under GenBank Accession No. 11428335 | 564 nts |
| SEQ ID NO: 4 | Polypeptide encoded by SEQ ID NO: 3 | 187 aa |
| SEQ ID NO: 5 | Full-length human CDS encoding interferon beta 2 as set forth under GenBank Accession No. 32673 | 639 nts |
| SEQ ID NO: 6 | Polypeptide encoded by SEQ ID NO: 5 | 212 aa |
| SEQ ID NO: 7 | Full-length human CDS encoding interferon alpha as set forth under GenBank Accession No. M54886 | 567 nts |
| SEQ ID NO: 8 | Polypeptide encoded by SEQ ID NO: 7 | 188 aa |
| SEQ ID NO: 9 | Full-length human CDS encoding interferon alpha 1 as set forth under GenBank Accession No. 11429098 | 570 nts |
| SEQ ID NO: 10 | Polypeptide encoded by SEQ ID NO: 9 | 189 aa |
| SEQ ID NO: 11 | Full-length human CDS encoding interferon alpha 2 as set forth under GenBank Accession No. 12734961 | 567 nts |
| SEQ ID NO: 12 | Polypeptide encoded by SEQ ID NO: 11 | 188 aa |
| SEQ ID NO: 13 | Full-length human CDS encoding B7-1 as set forth under GenBank Accession No. 4885122 | 867 nts |
| SEQ ID NO: 14 | Polypeptide encoded by SEQ ID NO: 13 | 288 aa |
| SEQ ID NO: 15 | Full-length human CDS encoding B7-2 as set forth under GenBank Accession No. 5901919 | 972 nts |
| SEQ ID NO: 16 | Polypeptide encoded by SEQ ID NO: 15 | 323 aa |
| SEQ ID NO: 17 | CDS encoding *Sus scrofa* B7-1 protein precursor as set forth under GenBank Accession No. AF203442 | 690 nts |
| SEQ ID NO: 18 | Polypeptide encoded by SEQ ID NO: 17 | 229 aa |
| SEQ ID NO: 19 | CDS encoding soluble human B7-1 protein precursor | 702 nts |
| SEQ ID NO: 20 | Polypeptide encoded by SEQ ID NO: 19 | 233 aa |

DETAILED DESCRIPTION OF THE INVENTION

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

The term "about" is used herein to refer to conditions (e.g., amounts, concentrations, time etc) that vary by as much as 30%, preferably by as much as 20%, and more preferably by as much as 10% to a specified condition.

The terms "administration simultaneously" or "administering simultaneously" refer to the administration of a single composition containing both an immunostimulatory molecule and interferon treated animal cell, or the administration of each active as separate compositions and/or delivered by separate routes within a short enough period of time that the effective result is equivalent to that obtained when both such actives are administered as a single composition.

By "agent" is meant a naturally occurring or synthetically produced molecule which interacts either directly or indirectly with a target member, the level and/or functional activity of which are to be modulated.

The term "analogue" refers to a molecule substantially similar in function to a reference molecule or to a biologically active fragment thereof.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity.

By "autologous" is meant something (e.g., cells, tissues etc) derived from the same organism.

The term "allogeneic" as used herein refers to cells, tissues, organisms etc that are of different genetic constitution.

By "biologically active fragment" is meant a fragment of a full-length parent polypeptide which fragment retains the activity of the parent polypeptide. A biologically active fragment will, therefore, inter alia have a biological activity of a parent polypeptide selected from an interferon alpha, an interferon beta, an interferon gamma, a B7-1 molecule and a B7-2 molecule. As used herein, the term "biologically active fragment" includes deletion mutants and small peptides, for example of at least 8, preferably at least 10, more preferably at least 15, even more preferably at least 20 and even more preferably at least 30 contiguous amino acids, which comprise the above activities. Peptides of this type may be obtained through the application of standard recombinant nucleic acid techniques or synthesised using conventional liquid or solid phase synthesis techniques. For example, reference may be made to solution synthesis or solid phase synthesis as described, for example, in Chapter 9 entitled "Peptide Synthesis" by Atherton and Shephard which is included in a publication entitled "Synthetic Vaccines" edited by Nicholson and published by Blackwell Scientific Publications. Alternatively, peptides can be produced by digestion of a polypeptide of the invention with proteinases such as endoLys-C, endoArg-C, endoGlu-C and *staphylococcus* V8-protease. The digested fragments can be purified by, for example, high performance liquid chromatographic (HPLC) techniques.

As used herein, a "cellular composition", "cellular vaccine" or "cellular immunogen" refers to a composition comprising at least one cell population, which is optionally inactivated, as an active ingredient.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "corresponds to" or "corresponding to" is meant a polynucleotide (a) having a nucleotide sequence that is substantially identical or complementary to all or a portion of a reference polynucleotide sequence or (b) encoding an amino acid sequence identical to an amino acid sequence in a peptide or protein. This phrase also includes within its scope a peptide or polypeptide having an amino acid sequence that is substantially identical to a sequence of amino acids in a reference peptide or protein.

By "derivative" is meant a polypeptide that has been derived from the basic sequence by modification, for example by conjugation or complexing with other chemical moieties or by post-translational modification techniques as would be understood in the art. The term "derivative" also includes within its scope alterations that have been made to a parent sequence including additions, or deletions that provide for functionally equivalent molecules.

To enhance immune response ("immunoenhancement"), as is well-known in the art, means to increase the animal's capacity to respond to foreign or disease-specific antigens (e.g., cancer antigens) i.e., those cells primed to attack such antigens are increased in number, activity, and ability to detect and destroy the those antigens. Strength of immune response is measured by standard tests including: direct measurement of peripheral blood lymphocytes by means known to the art; natural killer cell cytotoxicity assays (see, e.g., Provinciali M. et al (1992, *J. Immunol. Meth.* 155: 19-24), cell proliferation assays (see, e.g., Vollenweider, I. And Groseurth, P. J. (1992, *J. Immunol. Meth.* 149: 133-135), immunoassays of immune cells and subsets (see, e.g., Loeffler, D. A., et al. (1992, *Cytom.* 13: 169-174); Rivoltini, L., et al. (1992, *Can. Immunol. Immunother.* 34: 241-251); or skin tests for cell-mediated immunity (see, e.g., Chang, A. E. et al (1993, *Cancer Res.* 53: 1043-1050). Any statistically significant increase in strength of immune response as measured by the foregoing tests is considered "enhanced immune response" "immunoenhancement" or "immunopotentiation" as used herein. Enhanced immune response is also indicated by physical manifestations such as fever and inflammation, as well as healing of systemic and local infections, and reduction of symptoms in disease, i.e., decrease in tumour size, alleviation of symptoms of a disease or condition including, but not restricted to, leprosy, tuberculosis, malaria, naphthous ulcers, herpetic and papillomatous warts, gingivitis, artheroscleroosis, the concomitants of AIDS such as Kaposi's sarcoma, bronchial infections, and the like. Such physical manifestations also define "enhanced immune response" "immunoenhancement" or "immunopotentiation" as used herein.

As used herein, the term "function" refers to a biological, enzymatic, or therapeutic function.

By "greatly increased levels" or "high levels" in the context of molecular expression is meant expression of a molecule at levels that are 10-fold, more preferably 50-fold, more preferably 100-fold and more preferably 200-fold above a reference level. For example, B16High cells as used herein, express greatly increased levels of a B7 molecule on their surface, which levels are 10-fold, more preferably 50-fold, more preferably 100-fold and more preferably 200-fold above wild-type B16 cells.

"Homology" refers to the percentage number of amino acids that are identical or constitute conservative substitutions as defined in Table A infra. Homology may be determined using sequence comparison programs such as GAP (Deveraux et al. 1984, Nucleic Acids Research 12, 387-395). In this way, sequences of a similar or substantially different length to those cited herein might be compared by insertion of gaps into the alignment, such gaps being determined, for example, by the comparison algorithm used by GAP.

"Hybridisation" is used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA U pairs with A and C pairs with G. In this regard, the terms "match" and "mismatch" as used herein refer to the hybridisation potential of paired nucleotides in complementary nucleic acid strands. Matched nucleotides hybridise efficiently, such as the classical A-T and G-C base pair mentioned above. Mismatches are other combinations of nucleotides that do not hybridise efficiently.

Reference herein to "immuno-interactive" includes reference to any interaction, reaction, or other form of association between molecules and in particular where one of the molecules is, or mimics, a component of the immune system.

"Inactivation" of a cell is used herein to indicate that the cell has been rendered incapable of cell division to form progeny. The cell may nonetheless be capable of response to stimulus, or biosynthesis and/or secretion of cell products such as cytokines. Methods of inactivation are known in the art. Preferred methods of inactivation are treatment with toxins such as mitomycin C, or irradiation. Cells that have been fixed or permeabilised and are incapable of division are also examples of inactivated cells.

By "isolated" is meant material that is substantially or essentially free from components that normally accompany it in its native state.

A composition is "immunogenic" if it is capable of either: a) generating an immune response against an antigen (e.g., a tumour antigen) in a naive individual; or b) reconstituting, boosting, or maintaining an immune response in an individual beyond what would occur if the compound or composition was not administered. A composition is immunogenic if it is capable of attaining either of these criteria when administered in single or multiple doses.

By "modulating" is meant increasing or decreasing, either directly or indirectly, the level and/or functional activity of a target molecule. For example, an agent may indirectly modulate the said level/activity by interacting with a molecule other than the target molecule. In this regard, indirect modulation of a gene encoding a target polypeptide includes within its scope modulation of the expression of a first nucleic acid molecule, wherein an expression product of the first nucleic acid molecule modulates the expression of a nucleic acid molecule encoding the target polypeptide.

By "obtained from" is meant that a sample such as, for example, a nucleic acid extract or polypeptide extract is isolated from, or derived from, a particular source of the host. For example, the extract may be obtained from a tissue or a biological fluid isolated directly from the host.

The term "oligonucleotide" as used herein refers to a polymer composed of a multiplicity of nucleotide units (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotides and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule may vary depending on the particular application. An oligonucleotide is typically rather short in length, generally from about 10 to 30 nucleotides, but the term can refer to molecules of any length, although the term "polynucleotide" or "nucleic acid" is typically used for large oligonucleotides.

By "operably linked" is meant that transcriptional and translational regulatory nucleic acids are positioned relative to a polypeptide-encoding polynucleotide in such a manner that the polynucleotide is transcribed and the polypeptide is translated.

The term "patient" refers to patients of human or other mammal and includes any individual it is desired to examine or treat using the methods of the invention. However, it will be understood that "patient" does not imply that symptoms are present. Suitable mammals that fall within the scope of the invention include, but are not restricted to, primates, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes).

By "pharmaceutically-acceptable carrier" is meant a solid or liquid filler, diluent or encapsulating substance that may be safely used in topical or systemic administration.

The term "polynucleotide" or "nucleic acid" as used herein designates mRNA, RNA, cRNA, cDNA or DNA. The term typically refers to oligonucleotides greater than 30 nucleotides in length.

The terms "polynucleotide variant" and "variant" refer to polynucleotides displaying substantial sequence identity with a reference polynucleotide sequence or polynucleotides that hybridise with a reference sequence under stringent conditions that are defined hereinafter. These terms also encompasses polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. The terms "polynucleotide variant" and "variant" also include naturally occurring allelic variants.

"Polypeptide", "peptide" and "protein" are used interchangeably herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers.

The term "polypeptide variant" refers to polypeptides which vary from a reference polypeptide by the addition, deletion or substitution of at least one amino acid. It is well understood in the art that some amino acids may be changed to others with broadly similar properties without changing the nature of the activity of the polypeptide. Accordingly, polypeptide variants as used herein encompass polypeptides that have similar activities to a parent polypeptide selected from an interferon alpha, an interferon beta, an interferon gamma, a B7-1 molecule and a B7-2 molecule. Preferred variant polypeptides comprise conservative amino acid substitutions. Exemplary conservative substitutions in a polypeptide may be made according to the following table:

TABLE B

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile, |
| Phe | Met, Leu, Tyr |
| Ser | Thr |
| Thr | Ser |
| Trp | Tyr |
| Tyr | Trp, Phe |
| Val | Ile, Leu |

Substantial changes in function are made by selecting substitutions that are less conservative than those shown in TABLE B. Other replacements would be non-conservative substitutions and relatively fewer of these may be tolerated. Generally, the substitutions which are likely to produce the greatest changes in a polypeptide's properties are those in which (a) a hydrophilic residue (e.g., Ser or Asn) is substituted for, or by, a hydrophobic residue (e.g., Ala, Leu, Ile, Phe or Val); (b) a cysteine or proline is substituted for, or by, any other residue; (c) a residue having an electropositive side chain (e.g., Arg, His or Lys) is substituted for, or by, an electronegative residue (e.g., Glu or Asp) or (d) a residue having a smaller side chain (e.g., Ala, Ser) or no side chain (e.g., Gly) is substituted for, or by, one having a bulky side chain (e.g., Phe or Trp).

By "primer" is meant an oligonucleotide which, when paired with a strand of DNA, is capable of initiating the synthesis of a primer extension product in the presence of a suitable polymerising agent. The primer is preferably single-stranded for maximum efficiency in amplification but may alternatively be double-stranded. A primer must be sufficiently long to prime the synthesis of extension products in the presence of the polymerisation agent. The length of the primer depends on many factors, including application, temperature to be employed, template reaction conditions, other reagents, and source of primers. For example, depending on the complexity of the target sequence, the oligonucleotide primer typically contains 15 to 35 or more nucleotides, although it may contain fewer nucleotides. Primers can be large polynucleotides, such as from about 200 nucleotides to several kilobases or more. Primers may be selected to be "substantially complementary" to the sequence on the template to which it is designed to hybridise and serve as a site for the initiation of synthesis. By "substantially complementary", it is meant that the primer is sufficiently complementary to hybridise with a target nucleotide sequence. Preferably, the primer contains no mismatches with the template to which it is designed to hybridise but this is not essential. For example, non-complementary nucleotides may be attached to the 5' end of the primer, with the remainder of the primer sequence being complementary to the template. Alternatively, non-complementary nucleotides or a stretch of non-complementary nucleotides can be interspersed into a primer, provided that the primer sequence has sufficient complementarity with the sequence of the template to hybridise therewith and thereby form a template for synthesis of the extension product of the primer.

"Probe" refers to a molecule that binds to a specific sequence or sub-sequence or other moiety of another molecule. Unless otherwise indicated, the term "probe" typically refers to a polynucleotide probe that binds to another nucleic acid, often called the "target nucleic acid", through complementary base pairing. Probes may bind target nucleic acids lacking complete sequence complementarity with the probe, depending on the stringency of the hybridisation conditions. Probes can be labelled directly or indirectly.

The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably linked to the nucleotide sequence.

By "recombinant polypeptide" is meant a polypeptide made using recombinant techniques, i.e., through the expression of a recombinant polynucleotide.

By "reporter molecule" as used in the present specification is meant a molecule that, by its chemical nature, provides an analytically identifiable signal that allows the detection of a complex comprising an antigen-binding molecule and its target antigen. The term "reporter molecule" also extends to use of cell agglutination or inhibition of agglutination such as red blood cells on latex beads, and the like.

As used herein "stimulating" an immune or immunological response refers to administration of a composition that initiates, boosts, or maintains the capacity for the host's immune system to react to a target substance, such as a foreign molecule, an allogeneic cell, or a tumour cell, at a level higher than would otherwise occur. Stimulating a "primary" immune response refers herein to eliciting specific immune reactivity in a subject in which previous reactivity was not detected; for example, due to lack of exposure to the target antigen, refractoriness to the target, or immune suppression. Stimulating a "secondary" response refers to the reinitiation, boosting, or maintenance of reactivity in a subject in which previous reactivity was detected; for example, due to natural immunity, spontaneous immunisation, or treatment using one or several compositions or procedures.

By "therapeutically effective amount", in the context of treating a condition, is meant the administration of that amount of immunopotentiating composition that elicits an immune response in an individual in need of such treatment, either in a single dose or as part of a series, that is effective for treatment of that condition. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

The term "valency" as used herein refers to the number of binding sites available per molecule.

By "vector" is meant a nucleic acid molecule, preferably a DNA molecule derived, for example, from a plasmid, bacteriophage, or plant virus, into which a nucleic acid sequence may be inserted or cloned. A vector preferably contains one or more unique restriction sites and may be capable of autonomous replication in a defined host cell including a target cell or tissue or a progenitor cell or tissue thereof, or be integrable with the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector may also include a selection marker such as an antibiotic resistance gene that can be used for selection of suitable transformants. Examples of such resistance genes are well known to those of skill in the art.

Abbreviations

The following abbreviations are used in the present specification.
aa Amino acid(s)
CDS Coding sequence
IFN Interferon
IFN-alpha alpha-Interferon
IFN-beta beta-Interferon
IFN-gamma gamma-Interferon
Ig Immunoglobulin
IL Interleukin
ISGF3gamma IFN-stimulated gene factor 3 (ISGF3gamma is a transcription factor which is a complex of STAT molecules including STAT1 and STAT2 (31))
ISRE IFN-stimulated response element
JAK-1 Janus Kinase-1
MAbs Monoclonal antibodies
MHC Major Histocompatability Complex
MLC Mixed lymphocyte cultures
MLR Mixed lymphocyte reaction
nts nucleotides
p48-ISGF3gamma A component of ISGF-3 induced by gamma interferon
STAT Signal transducers and activators of transcription
TYK-2 Tyrosine Kinase-2

Immunopotentiating Compositions

The present invention stems at least in part from the discovery that there is a synergistic enhancement in immunopotentiation of animal cells by culturing the animal cells in the presence of at least one interferon followed by washing the animal cells to remove the interferon(s), wherein the animal cells express on their surface, or are otherwise provided in combination, an immunostimulatory molecule.

The invention thus provides in one aspect a method for enhancing immunopotentiation of animal cells, comprising culturing animal cells with at least one interferon for a time and under conditions sufficient to enhance the antigen presenting function of the cells and washing the animal cells to remove the at least one interferon, wherein the cells express on their surface, or are otherwise provided in combination, an immunostimulatory molecule.

In a preferred embodiment, the method further comprises isolating cells expressing said immunostimulatory molecule from a heterogeneous population of animal cells. Any method of isolation is contemplated by the present invention. Suitable methods for isolating particular cells are known to those of skill in the art. For example, one can take advantage of one or more particular characteristics of a cell to specifically isolate that cell from a heterogeneous population. Such characteristics include, but are not limited to, anatomical location of a cell, cell density, cell size, cell morphology, cellular metabolic activity, cell uptake of ions such as $Ca^{2+}$, $K^+$, and $H^+$ ions, cell uptake of compounds such as stains, markers expressed on the cell surface, protein fluorescence, and membrane potential. Suitable methods that can be used in this regard include surgical removal of tissue, flow cytometry techniques such as fluorescence-activated cell sorting (FACS), immunoaffinity separation (e.g., magnetic bead separation such as Dynabead™ separation), density separation (e.g., metrizamide, Percoll™, or Ficol™ gradient centrifugation), and cell-type specific density separation.

In the present case, the cells are preferably isolated by flow cytometry or by immunoaffinity separation using an antigen-binding molecule that is immuno-interactive with the immunostimulatory molecule.

According to an alternate embodiment, the method further comprises modifying the animal cells to express on their surface the immunostimulatory molecule. Thus, the immunostimulatory molecule can be an immunostimulatory membrane molecule, wherein at least a portion of said molecule is exposed to the extracellular environment (i.e., the exterior of a respective cell). In this instance, the immunostimulatory molecule is preferably an immunostimulatory membrane molecule, which is suitably a T cell co-stimulatory molecule. In one embodiment, the T cell co-stimulatory molecule is a B7 molecule, or biologically active fragment thereof, or variant or derivative of these. The B7 molecule includes, but is not restricted to, B7-1 and B7-2. Preferably, the B7 molecule is B7-1. Suitable polypeptide sequences for B7-1 and B7-2 include, but are not restricted to, those set forth respectively in SEQ ID NO: 14 and 16, including biologically-active fragments thereof, and variants or derivatives of these. In an alternate embodiment, the T cell co-stimulatory molecule is an ICAM molecule such as ICAM-1 and ICAM-2.

Preferably, the step of modification comprises introducing into said animal cells a polynucleotide from which the immunostimulatory molecule can be translated. Suitably, the polynucleotide is operably linked to a regulatory polynucleotide preferably in the form of an expression vector. Regulatory polynucleotides which can be utilised to regulate expression of the polynucleotide include, but are not limited to, a promoter, an enhancer, and a transcription terminator. Such regulatory polynucleotides are known to those of skill in the art. The expression vector preferably comprises at least one promoter. Suitable promoters that can be utilised to induce expression of the polynucleotide include constitutive promoters and inducible promoters.

Any suitable polynucleotide encoding the B7 molecule can be employed. Polynucleotides encoding B7-1 molecules which can be utilised in accordance with the invention are described, for example, in Freeman et al. (1989, *J. Immunol.* 143: 2714-2722), Freeman et al. (1992, *Blood* 79: 489-494), and in the GenBank database under locus designations HUMIGB7 (Accession number M27533) and NM_005191 (Accession number NM_005191). An exemplary polynucleotide sequence encoding B7-1 is set forth in SEQ ID NO: 13. Suitable polynucleotides encoding B7-2 molecules are described, for example, in Azuma et al. (1993, *Nature* 336: 76-79), Chen et al. (1994, *J. Immunol.* 152: 4929-4963), and in the GenBank database under locus designation NM_006889 (Accession number NM_006889). A suitable B7-2 encoding polynucleotide is set forth in SEQ ID NO: 15.

An exemplary expression vector for expression of the immunostimulatory protein includes the herpes simplex amplicons described for example by Fong et al. in U.S. Pat. No. 6,051,428.

It will be understood by persons of skill in the art that the techniques for assembling and expressing DNA encoding the immunostimulatory molecule, e.g., synthesis of oligonucleotides, nucleic acid amplification techniques, transforming cells, constructing vectors, expression systems, and the like and transducing or otherwise introducing such DNA into animal cells are well-established in the art, and most practitioners are familiar with the standard resource materials for specific conditions and procedures.

In another embodiment, the immunostimulatory molecule is suitably in soluble form. In a preferred embodiment of this type, the immunostimulatory protein is a B7 molecule that lacks a functional transmembrane domain. Preferably, the soluble B7 molecule comprises a B7 extracellular domain. Soluble B7-1 molecules of this type are disclosed, for example, by McHugh et al (1998, *Clin. Immunol Immunopathol.* 87(1): 50-59), Faas et al. (2000, *J. Immunol.* 164(12): 6340-6348) and Jeannin et al. (2000, *Immunity* 13(3): 303-312). Examples of polypeptide sequences for soluble B7-1 include, but are not limited to, those set forth in SEQ ID NO: 18 and 20, including biologically-active fragments thereof, and variants or derivatives of these. In another preferred embodiment of this type, the immunostimulatory protein is a B7 derivative. The B7 derivative is suitably a chimeric or fusion protein comprising a B7 molecule, or biologically active fragment thereof, or variant or derivative of these, linked together with an antigen binding molecule which is preferably an immunoglobulin molecule or biologically active fragment thereof.

Preferred chimeric proteins in accordance with the present invention include chimeric proteins which comprise a polypeptide corresponding to a biologically active fragment of a B7 molecule. For example, a derivative of a B7 molecule useful in the method of the present invention is a B7Ig fusion protein that comprises a polypeptide corresponding to the extracellular domain of the B7 molecule and an immunoglobulin constant region that alters the solubility, affinity and/or valency of the B7 molecule.

In a preferred embodiment, a polynucleotide encoding the amino acid sequence corresponding to the extracellular domain of the B7-1 molecule, containing amino acids from about position 1 to about position 215, is joined to a polynucleotide encoding the amino acid sequences corresponding to the hinge, CH2 and CH3 regions of human Ig Cγ1, using PCR, to form a construct that is expressed as a B7Ig fusion protein. DNA encoding the amino acid sequence corresponding to a B7Ig fusion protein has been deposited with the American Type culture Collection (ATCC) in Rockville, Md., under the Budapest Treaty on May 31, 1991 and accorded accession number 68627. Techniques for making and assembling such B7 derivatives are disclosed for example by Linsley et al. (U.S. Pat. No. 5,580,756). Reference also may be made to Sturmhoefel et al. (1999, *Cancer Res.* 59: 4964-4972) who disclose fusion proteins comprising the extracellular region of B7-1 or B7-2 fused in frame to the Fc portion of IgG2a.

The half-life of a soluble immunostimulatory protein may be prolonged by any suitable procedure if desired. Preferably, such molecules are chemically modified with polyethylene glycol (PEG), including monomethoxy-polyethylene glycol, as for example disclosed by Chapman et al (1999, *Nature Biotechnology* 17: 780-783).

The step of culturing may comprise contacting said cells with at least one type I interferon and/or a type II interferon. The at least one type I interferon is preferably selected from the group consisting of an IFN-alpha, an IFN-beta, a biologically active fragment of an IFN-alpha, a biologically active fragment of an IFN-beta, a variant of an IFN-alpha, a variant of an IFN-beta, a variant of a said biologically active fragment, a derivative of an IFN-alpha, a derivative of an IFN-beta, a derivative of a said biologically active fragment, a derivative of a said variant, an analogue of IFN-alpha and an analogue of IFN-beta. Preferably, the type II interferon is selected from the group consisting of an IFN-gamma, a biologically active fragment of an IFN-gamma, a variant of an IFN-gamma, a variant of said biologically active fragment, a derivative of an IFN-gamma, a derivative of said biologically active fragment, a derivative of said variant and an analogue of an IFN-gamma.

Suitably, the IFN-gamma comprises the amino acid sequence set forth in SEQ ID NO: 2.

In one embodiment, the IFN-beta is an IFN-beta 1, which suitably comprises the amino acid sequence set forth in SEQ ID NO: 4. In an alternate embodiment, the IFN-beta is an IFN-beta 2, which preferably comprises the amino acid sequence set forth in SEQ ID NO: 6.

In one embodiment, the IFN-alpha comprises the amino acid sequence set forth in SEQ ID NO: 8. In an alternate embodiment, the IFN-alpha is an IFN-alpha 1, which suitably comprises the amino acid sequence set forth in SEQ ID NO: 10. In yet another embodiment, the IFN-alpha is an IFN-alpha 2, which suitably comprises the amino acid sequence set forth in SEQ ID NO: 12.

For example, IFN-alpha and/or IFN-beta may be used directly on the cells or the cells may first be cultured in the presence of IFN-gamma prior to treatment with IFN-alpha and/or IFN-beta. Although not intending to limit the present invention to any one theory or particular mode of action, it is proposed this IFN-gamma restores or enhances levels of transcriptional factors required for transcriptional activation of genes regulated by IFN-alpha and IFN-beta.

Accordingly, the step of culturing preferably comprises contacting said cells with a type II IFN for a time and under conditions sufficient to permit cellular responsiveness to at least one type I interferon and then contacting said cultured cells with the at least one type I IFN for a time and under conditions sufficient to enhance the antigen presenting function of said cells.

In one embodiment, the cells cultured in the presence of the type II IFN are contacted with a type I IFN selected from the group consisting of an IFN-beta, a biologically active fragment of an IFN-beta, a variant of an IFN-beta, a variant of a said biologically active fragment, a derivative of an IFN-beta, a derivative of a said biologically active fragment, a derivative of a said variant and an analogue of an IFN-beta.

In another embodiment, the cells cultured in the presence of the type II IFN are contacted with a type I IFN selected from the group consisting of an IFN-alpha, a biologically active fragment of an IFN-alpha, a variant of an IFN-alpha, a variant of a said biologically active fragment, a derivative of an IFN-alpha, a derivative of a said biologically active fragment, a derivative of a said variant and an analogue of an IFN-alpha.

In yet another embodiment, the cells cultured in the presence of the type II IFN are contacted with a first type I IFN selected from the group consisting of an IFN-beta, a biologically active fragment of an IFN-beta, a variant of an IFN-beta, a variant of a said biologically active fragment, a derivative of an IFN-beta, a derivative of a said biologically active fragment, a derivative of a said variant and an analogue of an IFN-beta, and a second type I interferon selected from the group consisting of an IFN-alpha, a biologically active fragment of an IFN-alpha, a variant of an IFN-alpha, a variant of a said biologically active fragment, a derivative of an IFN-alpha, a derivative of a said biologically active fragment, a derivative of a said variant and an analogue of an IFN-alpha.

Suitably, the cells are cultured with a type II IFN (e.g., IFN-gamma), from about 16 to about 96 hours and subsequently with one or more type I interferons (e.g., IFN-alpha and/or IFN-beta) from about 16 to about 72 hours. Preferably, the cells are cultured with a type II IFN (e.g., IFN-gamma) from about 48 to about 96 hours and subsequently with one or more type I interferons (e.g., IFN-alpha and/or IFN-beta) from about 24 to about 72 hours.

The cells may be treated with IFN-gamma at a concentration of about 100 to about 2000 international units/mL and subsequently with IFN-alpha and/or IFN-beta at a concentration of about 100 to about 2000 international units/mL. Preferably, the cells are cultured with IFN-gamma at a concentration of about 1000 international units/mL and subsequently with IFN-alpha and/or IFN-beta at a concentration of about 1000 international units/mL.

It will be appreciated that the animal cells are, therefore, subjected to at least one IFN in concentrated form unattainable in a recipient host. Not wishing to be bound by any one particular theory or mode of action, the culturing in the presence of the at least one IFN potentiates both the ability of the animal cells to process antigens via antigen processing pathways and to present the processed antigens on the cell surface. The presence of the immunostimulatory molecule, which is preferably a T cell co-stimulatory molecule, on the surface of the animal cells, or in combination therewith, provides the means to effect T cell activation through, for example, the CD28 or CTLA4 receptors present on T cells.

Preferably, the step of culturing further comprises expanding the population of isolated cells in culture. Such expansion techniques are known to those of skill in the art. For example, the expanded population of cells as described infra is prepared from isolated cells grown in flasks. The production of the expanded population can, if desired, be scaled up by culturing the cells in bioreactors or fermentors or other such vessels or devices suitable for the growing of cells in bulk. The isolated population is preferably expanded in the presence of suitable complete growth media (for example, RPMI OR DMEM containing 10% foetal calf sera or serum free media) in the presence of one or more cytokines/growth factors including, but not restricted to, fibroblast growth factor, at 37° C., 5-7% carbon dioxide.

One particular advantage of the present invention is that no predetermined selection of the types of antigens presented on the cells occurs since the cells are used as a source of immunogen. Accordingly, a large array of the antigens normally processed by the cells will be available to activate immune cell processes, resulting in a wide variation in the populations of responding immune cells to the range of different antigenic targets. By way of example, a cancer cell will expresses multiple tumour-associated antigens shared by the tumour of a patient to be treated.

Furthermore, antigens are presented in the configuration evolved through natural selection, which is used by antigen presenting cells and, hence, provides for strong immune cell activation. Alternatively, treated cells may be loaded with particular antigenic peptides, which are preferably tumour antigens, to yield specific targeted vaccines. For example, reference may be made to Van Pel et al (1995, *Immunol Rev* 145: 229-50) who describe various genes encoding tumour antigens recognised by CTL. Reference also may be made to Itoh et al (1994, *J. Immunol.* 153: 1202-1215) and Cole et al (1995, *Cancer Res.* 55: 748-752) who describe the use of loading peptides on tumour cells as targets for CTL killing.

Preferred cells are those with a defined MHC genomic region or equivalent and with the capability of increasing or enhancing class I MHC presentation of antigenic molecules to cell surfaces.

The cells of the present invention may be isolated from the intended host, treated and then re-introduced or reinfused into that host. It is particularly convenient to use cells obtained from the host to be treated, either by surgical resection, biopsy, blood sampling, or other suitable technique. Such cells are referred to herein as "autologous" cells. Alternatively, cells or cell lines (e.g., tumour cell lines) may be prepared and/or cultured from one source and introduced into a different host. Such cells are referred to herein as "allogeneic" cells. One particular form of allogeneic cells comprises a generic cell line with shared major and/or minor histocompatibility antigens to potential recipients.

Suitably, the generic cell line naturally expresses the immunostimulatory molecule, preferably an immunostimulatory membrane molecule, at levels sufficient to trigger an immune response, preferably a T cell immune response, and more preferably a cytotoxic T lymphocyte immune response, in the intended host.

It is preferred the generic cell line comprises major histocompatibility (MHC) class I antigens compatible with a high percentage of the population that is susceptible or predisposed to a particular condition. Suitably, the condition being treated or prevented by vaccination is a cancer or tumour. Preferably, the generic cell line expresses high levels of an endogenous B7 molecule. It is also preferred that the generic cell line is highly susceptible to treatment with at least one IFN as described herein (i.e., implied high level expression of class I HLA).

In one embodiment, treated cells (e.g., cancer cells) or cell lines are suitably rendered inactive to prevent further proliferation once administered to the subject. Any physical, chemical, or biological means of inactivation may be used, including but not limited to irradiation (preferably with at least about 5,000 cGy, more preferably at least about 10,000 cGy, more preferably at least about 20,000 cGy); or treatment with mitomycin-C (preferably at least 10 µg/mL; more preferably at least about 50 µg/mL).

The present invention extends to animal cells from, for example, avian species, reptiles and mammals. Mammals are preferred and include humans, livestock animals (e.g., sheep, cows, horses, pigs), laboratory test animals (e.g., mice, rats, rabbits, guinea pigs), companion animals (e.g., cats, dogs) and captive wild animals (e.g., kangaroos, deer, foxes). Humans are the most preferred animals and both autologous and allogeneic cells may be employed in human subjects.

The animal cells are preferably cancer or tumour cells. The compositions or vaccines in accordance with the present invention would be derived from the tumour or cancer cells. For example, in the treatment of lung cancer in accordance with the practices of this invention, the lung cancer cells would be treated as described hereinabove to produce a lung cancer vaccine. Similarly, breast tumour or cancer cells, prostate cancer cells, colon cancer cells, pancreas cancer cells, stomach cancer cells, bladder cancer cells, kidney cancer cells and the like would be produced and employed as immunotherapeutic agents in accordance with the practices for the prevention and/or treatment of the tumour or cancer cell from which the composition of matter or vaccine according to the invention was produced. In a preferred embodiment, the cancer or tumour cells are preferably selected from the group consisting of melanoma cells and mammary carcinoma cells.

The compositions of matter according to the invention could also be prepared to treat various infectious diseases that affect humans and animals by loading antigens of a pathogenic organism (e.g., viral, bacterial, fungal, protozoan) onto the treated cells. As there is heterogeneity in the type of immunogenic and protective antigens expressed by different varieties of organisms causing the same disease, polyvalent compositions and vaccines could be prepared by preparing the composition or vaccine from a pool of organisms expressing the different antigens of importance. The invention, therefore, also encompasses a method for stimulating a patient's immune system, and preferably for modulating the T cell response of the patient to one or more antigens by administering to the patient animal cells cultured in the presence of at least one interferon (IFN) for a time and under conditions sufficient to enhance the antigen presenting functions of said cells, together with the or each antigen. Accordingly, the immunogenicity of an antigen can be enhanced or otherwise improved in vitro, by isolating animal cells from a subject, "pulsing" or contacting them with the antigen, then using the pulsed cells to stimulate autologous T cells in vitro or in vivo.

The compositions of matter according to the invention could also be prepared to treat immunocompromised animals that may be suffering or have a propensity to suffer from bacterial, viral or yeast infection, protozoan or other parasite infection or have a cancer such as melanoma or other sarcoma or tumour.

From the foregoing, the invention broadly resides in a composition of matter comprising an immunostimulatory molecule and animal cells cultured in the presence of at least one interferon for a time and under conditions sufficient to enhance the antigen presenting function of said cells, wherein said cells have been washed to remove said interferon(s).

In a preferred embodiment, the present invention provides a composition of matter comprising animal cells which express an immunostimulatory membrane protein, and which have been cultured in the presence of IFN-gamma and one or both of IFN-alpha and IFN-beta for a time and under conditions sufficient to enhance the antigen presenting function of said cells, wherein said cells have been washed to remove said IFNs.

The treated cells in combination with the immunostimulatory molecule above can be used as actives for the treatment or prophylaxis of various conditions as, for example, a tumour or cancer. These therapeutic agents can be administered to a patient either by themselves or in vaccines where they are mixed with one or more pharmaceutically acceptable carriers, adjuvants and/or diluents.

Vaccines

The invention also contemplates a vaccine for stimulating a host's immune system, comprising a composition of animal cells as broadly described above, said vaccine optionally further comprising one or more pharmaceutically acceptable carriers, adjuvants and/or diluents.

Cultured animal cells in combination with an immunostimulatory molecule according to the invention may be used as actives in the preparation of vaccines. Such preparation uses routine methods known to persons skilled in the art. Typically, such vaccines are prepared as injectables, either as liquid solutions or suspensions; solid forms suitable for solution in, or suspension in, liquid prior to injection may also be prepared. The preparation may also be emulsified. The active immunogenic ingredients are often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants that enhance the effectiveness of the vaccine. Examples of adjuvants which may be effective include but are not limited to: aluminium hydroxide, N-acetyl-muramyl-L-threonyl-D-isoglutamine (thur-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 1983A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. For example, the effectiveness of an adjuvant may be determined by measuring the amount of antibodies resulting from the administration of the vaccine, wherein those antibodies are directed against one or more antigens presented by the treated cells of the vaccine.

The cells should be administered in a pharmaceutically acceptable carrier, which is non-toxic to the cells and the individual. Such carrier may be the growth medium in which the cells were grown. Compatible excipients include isotonic saline, with or without a physiologically compatible buffer like phosphate or Hepes and nutrients such as dextrose, physiologically compatible ions, or amino acids, and various culture media suitable for use with cell populations, particularly those devoid of other immunogenic components. Carrying reagents, such as albumin and blood plasma fractions and nonactive thickening agents, may also be used. Non-active biological components, to the extent that they are present in the vaccine, are preferably derived from a syngeneic animal or human as that to be treated, and are even more preferably obtained previously from the subject. The injection site may be subcutaneous, intraperitoneal, intramuscular, intradermal, or intravenous.

If a soluble immunostimulatory molecule is employed as an active in the vaccine, the immunostimulatory molecule can be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric, maleic, and the like. Salts formed with the free carboxyl groups may also be derived from inorganic basis such as, for example, sodium, potassium, ammonium, calcium, or ferric hydroxides, and such organic basis as isopropylamine, trimethylamine, 2-ethylamino ethanol, histidine, procaine, and the like.

If desired, devices or compositions containing the vaccine and suitable for sustained or intermittent release could be, in effect, implanted in the body or topically applied thereto for the relatively slow release of such materials into the body.

It will be appreciated that the soluble immunostimulatory molecule may be administered to a patient separately to the administration of the cell-containing composition. Depending on the specific conditions being treated, the immunostimulatory molecule may be formulated and administered systemically or locally. Techniques for formulation and administration may be found in "Remington's Pharmaceutical Sciences," Mack Publishing Co., Easton, Pa., latest edition. Suitable routes may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

The number of IFN-treated cells and optionally the quantity of the immunostimulatory molecule to be administered may depend on the subject to be treated inclusive of the age, sex, weight and general health condition thereof. In this regard, precise amounts of the agent(s) for administration will depend on the judgement of the practitioner. In determining the effective amount of the agent(s) to be administered in the treatment of a disease or condition, the physician may evaluate the progression of the disease or condition over time. In any event, those of skill in the art may readily determine suitable dosages of the agents of the invention without undue experimentation. Cell-containing compositions and vaccines are suitably administered to a patient in the range of between about $10^4$ and $10^{10}$, and more preferably between about $10^6$ and $10^8$ treated cells/administration. The dosage of the immunostimulatory molecule administered to a patient should be sufficient in combination with the cellular component of the vaccine to effect a beneficial response in the patient over time such as a reduction in the symptoms associated with the cancer or tumour. Dosage amount and interval may be adjusted individually to provide plasma levels of the immunostimulatory molecule which are sufficient to maintain immunostimulatory effects. Usual patient dosages for systemic administration range from 1-2000 mg/day, commonly from 1-250 mg/day, and typically from 10-150 mg/day. Stated in terms of patient body weight, usual dosages range from 0.02-25 mg/kg/day, commonly from 0.02-3 mg/kg/day, typically from 0.2-1.5 mg/kg/day.

Also encapsulated by the present invention is a method for treatment and/or prophylaxis of a disease or condition, comprising administering to a patient in need of such treatment a therapeutically effective amount of a composition or vaccine as broadly described above.

In one embodiment, the cell-containing composition or vaccine of the invention could also be used for generating large numbers of $CD8^+$ or CD4+ CTL, for adoptive transfer to immunosuppressed individuals who are unable to mount normal immune responses. For example, antigen-specific $CD8^+$ CTL can be adoptively transferred for therapeutic purposes in individuals afflicted with HIV infection (Koup et al, 1991, *J. Exp. Med.* 174: 1593-1600; Carmichael et al., 1993, *J. Exp. Med.* 177: 249-256; and Johnson et al., 1992, *J. Exp. Med.* 175: 961-971), malaria (Hill et al, 1992, *Nature* 360: 434-439) and malignant tumours such as melanoma (Van der Brogen et al., 1991, *Science* 254: 1643-1647; and Young and Steinman 1990, *J. Exp. Med.*, 171: 1315-1332).

In another embodiment, the cell-containing composition or vaccine is suitable for treatment or prophylaxis of a cancer or tumour. Cancers or tumours which could be suitably treated in accordance with the practices of this invention include cancers or tumours of the lung such as small and large cell adenocarcinomas, squamous cell carcinoma, and brionchoalveolar carcinoma; breast tumours, such as ductal and lobular adenocarcinoma; gynecologic tumours, such as squamous and adenocarcinoma of the uterine cervix, and uterine and ovarian epithelial adenocarcinomaovary; colon tumours, such as epithelial adenocarcinoma and their metastases; pancreatic tumours such as pancreatic ductal adenocarcinomas; prostate tumours, such as prostatic adenocarcinoma; stomach; bladder tumours, such as transitional squamous cell carcinoma; kidney, bone, liver tumours, such as hepatoma and cholangiocarcinoma; tumours of the reticuloendothelial (RES) system, such as nodular or diffuse B or T cell lymphoma; plasmacytoma, and acute or chronic leukemia;

oesophageal cancer; brain tumours, such as astrocytoma, oligodendroglioma, ependymoma, medulloblastomas, primitive neural ectodermal tumour, gliomas, glioblastomas, and gliosarcomas; testicular tumours; skin tumours, such as malignant melanoma; soft tissue tumours, such as soft tissue sarcoma and leiomyosarcoma; and the various leukemias and lymphomas. In a preferred embodiment, the cancer is melanoma or breast cancer.

In yet another embodiment, the cell-containing composition or vaccine is suitable for treatment or prophylaxis of a viral, bacterial or parasitic infection. Viral infections contemplated by the present invention include, but are not restricted to, infections caused by HIV, Hepatitis, Influenza, Japanese encephalitis virus, Epstein-Barr virus and respiratory syncytial virus. Bacterial infections include, but are not restricted to, those caused by *Neisseria* species, *Meningococcal* species, *Haemophilus* species *Salmonella* species, *Streptococcal* species, *Legionella* species and *Mycobacterium* species. Parasitic infections encompassed by the invention include, but are not restricted to, those caused by *Plasmodium* species, *Schistosoma* species, *Leishmania* species, *Trypanosoma* species, *Toxoplasma* species and *Giardia* species.

The effectiveness of the immunization may be assessed using any suitable technique. For example, CTL lysis assays may be employed using stimulated splenocytes or peripheral blood mononuclear cells (PBMC) on peptide coated or recombinant virus infected cells using $^{51}$Cr or Alamar Blue™ labeled target cells. Such assays can be performed using for example primate, mouse or human cells (Allen et al., 2000, *J. Immunol.* 164(9): 4968-4978 also Woodberry et al., infra). Alternatively, the efficacy of the immunization may be monitored using one or more techniques including, but not limited to, HLA class I tetramer staining—of both fresh and stimulated PBMCs (see for example Allen et al., supra), proliferation assays (Allen et al., supra), ELISPOT assays and intracellular IFN-gamma staining (Allen et al., supra), ELISA Assays—for linear B cell responses; and Western blots of cell sample expressing the synthetic polynucleotides Process for Assessing Cellular Responsiveness to Interferon Treatment The invention also extends to a process for assessing the responsiveness of animal cells to treatment with at least one interferon. The process comprises detecting in animal cells: (1) the level and/or functional activity of a polypeptide involved in interferon signalling; (2) the level and/or functional activity of a cellular modulatory agent that modulates said polypeptide; (3) the level and/or functional activity of a downstream cellular target of said polypeptide; or (4) the level of an expression product of a genetic sequence encoding a member selected from the group consisting of said polypeptide, said modulatory agent and said downstream cellular target.

Suitably, the polypeptide is selected from the group consisting of Stat1, IRF-1, Stat2 and p48 ISGF3. Preferably, the polypeptide is Stat1.

Detection of Polypeptides

Polypeptides, modulators and target polypeptides as mentioned above may be detected by contacting a sample of the animal cells or extract thereof with an antigen-binding molecule that is immuno-interactive with the polypeptide, modulator or target polypeptide and detecting the presence of a complex comprising the said antigen-binding molecule and the said polypeptide, modulator or target in said contacted sample.

Any suitable technique for determining formation of the complex may be used. For example, an antigen-binding molecule according to the invention, having a reporter molecule associated therewith may be utilised in immunoassays. Such immunoassays include, but are not limited to, radioimmunoassays (RIAs), enzyme-linked immunosorbent assays (ELISAs) and immunochromatographic techniques (ICTs), Western blotting which are well known to those of skill in the art. For example, reference may be made to Coligan et al., CURRENT PROTOCOLS IN IMMUNOLOGY, (John Wiley & Sons, Inc, 1994), which discloses a variety of immunoassays that may be used in accordance with the present invention. Immunoassays may include competitive assays as understood in the art or as for example described infra. It will be understood that the present invention encompasses qualitative and quantitative immunoassays.

Suitable immunoassay techniques are described for example in U.S. Pat. Nos. 4,016,043, 4,424,279 and 4,018,653. These include both single-site and two-site assays of the non-competitive types, as well as the traditional competitive binding assays. These assays also include direct binding of a labelled antigen-binding molecule to a target antigen.

Two site assays are particularly favoured for use in the present invention. A number of variations of these assays exist, all of which are intended to be encompassed by the present invention. Briefly, in a typical forward assay, an unlabelled antigen-binding molecule such as an unlabelled antibody is immobilised on a solid substrate and the sample to be tested brought into contact with the bound molecule. After a suitable period of incubation, for a period of time sufficient to allow formation of an antibody-antigen complex, another antigen-binding molecule, suitably a second antibody specific to the antigen, labelled with a reporter molecule capable of producing a detectable signal is then added and incubated, allowing time sufficient for the formation of another complex of antibody-antigen-labelled antibody. Any unreacted material is washed away and the presence of the antigen is determined by observation of a signal produced by the reporter molecule. The results may be either qualitative, by simple observation of the visible signal, or may be quantitated by comparing with a control sample containing known amounts of antigen. Variations on the forward assay include a simultaneous assay, in which both sample and labelled antibody are added simultaneously to the bound antibody. These techniques are well known to those skilled in the art, including minor variations as will be readily apparent. In accordance with the present invention, the sample is one that might contain an antigen including serum, whole blood, and plasma or lymph fluid. The sample is, therefore, generally a circulatory sample comprising circulatory fluid.

In the typical forward assay, a first antibody having specificity for the antigen or antigenic parts thereof is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well known in the art and generally consist of cross-linking covalently binding or physically adsorbing, the polymer-antibody complex is washed in preparation for the test sample. An aliquot of the sample to be tested is then added to the solid phase complex and incubated for a period of time sufficient and under suitable conditions to allow binding of any antigen present to the antibody. Following the incubation period, the antigen-antibody complex is washed and dried and incubated with a second antibody specific for a portion of the antigen. The second antibody has generally a reporter molecule associated therewith that is used to indicate the binding of the second antibody to the antigen. The amount of labelled antibody that binds, as determined by the associated reporter molecule, is proportional to the amount of antigen bound to the immobilised first antibody.

An alternative method involves immobilising the antigen in the biological sample and then exposing the immobilised antigen to specific antibody that may or may not be labelled with a reporter molecule. Depending on the amount of target and the strength of the reporter molecule signal, a bound antigen may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

In a preferred embodiment, the polypeptides, modulators and target polypeptides as broadly described above may be detected, quantified or semi-quantified by flow cytometric analysis and immunofluorescent staining of intracellular antigens with antibodies to quantify and compare individual cells for antigen expression levels as for example disclosed by Clevenger, et al (1987, *J Cell Physiol.* 130: 336-343) and by Kuhar and Lehman (1991, *Oncogene* 6:1499-1506).

In an alternate embodiment, detection, quantification and semi-quantification may be effected using immunohistological analysis (e.g. diaminobenzidine staining of thin sections) as is known in the art.

From the foregoing, it will be appreciated that the reporter molecule associated with the antigen-binding molecule may include the following:
  (a) direct attachment of the reporter molecule to the antigen-binding molecule;
  (b) indirect attachment of the reporter molecule to the antigen-binding molecule; i.e., attachment of the reporter molecule to another assay reagent which subsequently binds to the antigen-binding molecule; and
  (c) attachment to a subsequent reaction product of the antigen-binding molecule.

The reporter molecule may be selected from a group including a chromogen, a catalyst, an enzyme, a fluorochrome, a chemiluminescent molecule, a lanthanide ion such as Europium ($Eu^{34}$), a radioisotope and a direct visual label.

In the case of a direct visual label, use may be made of a colloidal metallic or non-metallic particle, a dye particle, an enzyme or a substrate, an organic polymer, a latex particle, a liposome, or other vesicle containing a signal producing substance and the like.

A large number of enzymes suitable for use as reporter molecules is disclosed in U.S. Pat. Nos. 4,366,241, 4,843,000, and 4,849,338. Suitable enzymes useful in the present invention include alkaline phosphatase, horseradish peroxidase, luciferase, P-galactosidase, glucose oxidase, lysozyme, malate dehydrogenase and the like. The enzymes may be used alone or in combination with a second enzyme that is in solution.

Suitable fluorochromes include, but are not limited to, fluorescein isothiocyanate (FITC), tetramethylrhodamine isothiocyanate (TRITC), R-Phycoerythrin (RPE), and Texas Red. Other exemplary fluorochromes include those discussed by Dower et al. (International Publication WO 93/06121). Reference also may be made to the fluorochromes described in U.S. Pat. No. 5,573,909 (Singer et al), U. S Pat. No. 5,326,692 (Brinkley et al). Alternatively, reference may be made to the fluorochromes described in U.S. Pat. Nos. 5,227,487, 5,274,113, 5,405,975, 5,433,896, 5,442,045, 5,451,663, 5,453,517, 5,459,276, 5,516,864, 5,648,270 and 5,723,218.

In the case of an enzyme immunoassay, an enzyme is conjugated to the second antibody, generally by means of glutaraldehyde or periodate. As will be readily recognised, however, a wide variety of different conjugation techniques exist which are readily available to the skilled artisan. The substrates to be used with the specific enzymes are generally chosen for the production of, upon hydrolysis by the corresponding enzyme, a detectable colour change. Examples of suitable enzymes include those described supra. It is also possible to employ fluorogenic substrates, which yield a fluorescent product rather than the chromogenic substrates noted above. In all cases, the enzyme-labelled antibody is added to the first antibody-antigen complex. It is then allowed to bind, and excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of antigen which was present in the sample.

Alternately, fluorescent compounds, such as fluorescein, rhodamine and the lanthanide, europium (EU), may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. The fluorescent-labelled antibody is allowed to bind to the first antibody-antigen complex. After washing off the unbound reagent, the remaining tertiary complex is then exposed to light of an appropriate wavelength. The fluorescence observed indicates the presence of the antigen of interest. Immunofluorometric assays (IFMA) are well established in the art. However, other reporter molecules, such as radioisotope, chemiluminescent or bioluminescent molecules may also be employed.

Detection of Polynucleotides

In another embodiment, the method for detection comprises detecting expression in animal cells, or in extracts thereof, the level of an expression product of a genetic sequence encoding a member selected from the group consisting of said polypeptide, said modulatory agent and said downstream cellular target. Expression of the a polynucleotide may be determined using any suitable technique. For example, a labelled polynucleotide encoding a said member may be utilised as a probe in a Northern blot of a RNA extract obtained from the muscle cell. Preferably, a nucleic acid extract from the animal is utilised in concert with oligonucleotide primers corresponding to sense and antisense sequences of a polynucleotide encoding a said member, or flanking sequences thereof, in a nucleic acid amplification reaction such as RT PCR. A variety of automated solid-phase detection techniques are also appropriate. For example, very large scale immobilised primer arrays (VLSIPS™) are used for the detection of nucleic acids as for example described by Fodor et al., (1991, *Science* 251:767-777) and Kazal et al., (1996, *Nature Medicine* 2:753-759). The above generic techniques are well known to persons skilled in the art.

Methods for Assessing Cytotoxic T Lymphocyte Activity

The cytotoxic activity of T lymphocytes may be assessed by any suitable technique known to those of skill in the art. For example, a sample comprising T lymphocytes to be assayed for cytotoxic activity is obtained and the T lymphocytes are then exposed to IFN-treated target cells according to the invention. After an appropriate period of time, which may be determined by assessing the cytotoxic activity of a control population of T lymphocytes which are known to be capable of being induced to become cytotoxic cells, the T lymphocytes to be assessed are tested for cytotoxic activity in a standard cytotoxic assay. Such assays may include, but are not limited to, the chromium release CTL assay and the Alamar Blue™ fluorescence assay known in the art.

The method of assessing CTL activity is particularly useful for evaluating an individual's capacity to generate a cytotoxic response against cells expressing tumour or antigens of a pathogenic organism (e.g., viral antigens). Accordingly, this method is useful for evaluating an individual's ability to mount an immune response against a cancer or a pathogenic organism.

The invention also contemplates the use of IFN treatment in accordance with the teachings of the present invention to enhance the sensitivity of detecting cytolytic T lymphocyte (CTL) mediated lysis of a target cell. Accordingly, IFN treatment of a target cell can be used advantageously to develop assays with improved sensitivity for detecting an immune response, particularly a CTL response, and more particularly a $CD8^+$ CTL response, against that target cell.

In order that the invention may be readily understood and put into practical effect, particular preferred embodiments will now be described by way of the following non-limiting examples.

EXAMPLES

Example 1

Cell Cultures in IFN Stimulation

Melanoma cell line B16 (American type Culture Collection, Rockville, Md., USA), alone or transduced with a vector expressing murine B7-1 (polynucleotide encoding murine B7-1 cloned into pEF-MC1Neo-pA using PCR based methods), was grown in RPMI 1640 media supplemented with 10% v/v inactivated foetal calf serum (FCS), L-glutamine and sodium pyruvate at 37° C. in a 5% v/v $CO_2$ incubator. In all experiments, cells were maintained in serum free media (without 10% v/v FCS) for 24 h before stimulation with IFN. In those experiments using gamma-priming, cells were pretreated with 1000 IU/mL IFN-gamma (Amersham, Sydney, New South Wales, Australia) for 16-18 h at 37° C. in 5% v/v $CO_2$ incubator prior to stimulation with 1000 IU/mL IFN-alpha2a (Hoffman-La Roche, Basel, Switzerland) for the indicated time periods.

Recombinant IFNs were used throughout the study. Murine IFN-beta was obtained from Toray Industries, Inc., Kanagawa, Japan. Murine IFN-gamma was produced in the laboratory using the pPR-TGATG-1 vector system in *E. coli* strain DH50α (43) and was isolated from inclusion bodies, denatured in 6M Guanidinium HCl, refolded by slow dialysis, clarified and purified by ion-exchange chromatography on S-Sepharose Fast Flow (Pharmacia). The biological activity of IFNs in IU/mL was calibrated against NIH IFN-alpha and -beta reference standards (IFN-beta # Gb02-902-511, IFN-alpha # Ga02-901-511 obtained from the National Institute of Allergy and Infections Diseases, Bethesda, Md.) using an antiviral bioassay based on the inhibition of cytopathic effect of Semliki Forest virus in MDBK cells, similar to that described in (44).

Example 2

Cytotoxic T Cell Assay

Chromium Release Assay

A four hour $^{51}Cr$ release Cytotoxic T Cell assay was carried out using the B16 mouse melanoma cell line as targets or alternatively, transfected B16 cells expressing B7-1. The targets were set up at a sub-confluent state, 60 hrs before the CTL assay. Within 12 hrs of setting up the cells in culture (in Dulbecco's Modified Eagles medium, 10% FCS, 50 μg/mL Penicillin, 50 μg/mL Streptomycin), Murine Interferon gamma at 1000 IU/mL was added, followed by an addition of Murine Interferon beta at 1000 IU/mL 24 hrs later.

A standard Chromium release assay was carried out where the targets were labelled with 150 μCi/mL $Na_2^{51}CrO_4$ for 60-90 min and used to incubate with cultured splenocytes for 4 hrs at 37° C., 5% $CO_2$. CTL lysis was determined at effector:target (E:T) ratios ranging from 100:1 to 0.4:1. Supernatants (50 μL/sample) were harvested and counted using a scintillation cocktail (200 μL/sample well) (Star Scint, Can berra Packard) in a Top Count (Canberra Packard) using a 96 well plate format. Supernatants were also counted directly using a Gamma Counter (Can berra Packard). percent Specific Lysis was calculated using the following formula:

$$\% \text{ Specific Lysis} = 100 \times \frac{(\text{experimental release} - \text{spontaneous release})}{(\text{maximum release} - \text{spontaneous release})}$$

Maximum release of the targets was determined by lysis with 1% NP-40. In a CTL assay where spontaneously released values (cpm) were in excess of 20% of the maximum release, the assay was discarded.

Fluorescence Based CTL Assay

For the cytotoxicity assay using Alamar Blue™ (BioSource International, Camarillo, Calif., USA), the methods of Nociari et al., 1998 (42) were followed. Thus, $1 \times 10^3$ target cells were seeded per well and effector:target ratios (E:T) of 30:1, 25:1, 20:1, 15:1, 10:1, 7.5:1, 5:1, 2.5:1, 1.25:1, 0.625:1, 0.3125:1, 0.156:1 and 0.078:1 were used, as required. Each E:T ratio was performed in quadruplicate wells. Alamar Blue™ stock solution was added to the wells at time 0 after setting up the CTL assay at a final concentration of 10% and the plate was incubated at 37° C. in a humidified $CO_2$ incubator and read at 24 h. The fluorescence signal generated in each well was determined using an excitation wavelength of 520-530 nm and the emission at 590-595 nm. Fluorescence units detected for Targets alone and Effectors alone were correlated with values for the E:T mixed wells.

The cell lysis was calculated using the following equation:

$$\% \text{ Lysis} = 100 \times \frac{\left\{ \begin{array}{c} (AF*\text{Targets Alone}) + \\ (AF \text{ Effectors Alone}) \end{array} \right\} - \{(AF\ E{:}T\ \text{mixture})\}}{(AF\ \text{Targets Alone})}$$

* AF represents the mean of the absolute fluorescence units of Targets alone, or Effectors alone, or E:T mixture, minus the average fluorescence units of the media plus dye controls.

Example 3

Preparation of Splenocytes for CTL Assays

C57B7/6J male mice were subjected to an immunisation regime, 13 days prior the CTL assay. The mice were injected in the intra peritoneal cavity with irradiated $10^7$ B16 cells or B16-B7.1 cells. The cell preparations used as vaccine were pre-treated with interferon gamma for 72 h and murine interferon beta for 48 h prior to use. Six days after injection of immunogen, splenic lymphocytes were prepared. Red blood cells were lysed with 0.83% ammonium chloride solution buffered in Tris, pH 7.2 at 37° C., 2 mins. Splenic lymphocytes were plated out into 24 well plates at $4 \times 10^6$ cells/well in RPMI-1640 (Sigma) supplemented with 10% FCS (Commonwealth Serum Lab), 50 U/mL Penicillin (Trace Scientific Ltd), 50 µg/mL Streptomycin (Trace Scientific Ltd), 1.66 mM L-Glutamate (Sigma), 2 mM Sodium Pyruvate (Sigma), 20 mM Hepes (Sigma), 50 µM 2-mercaptoethanol (ICN).

To the splenic lymphocytes in culture, $2 \times 10^5$ irradiated stimulator cells/well were added and incubated at 37° C., 5% $CO_2$. Stimulators comprised of B16 cells or B16-B7.1 cells, which were pre treated with murine interferon gamma for 72 h and murine interferon beta for 48 h.

Two days before the CTL assay, the mixed lymphocyte culture (MLC)/stimulator medium was replenished with fresh medium.

On the day of the CTL assay, the MLC/stimulators were pooled and resuspended in a small volume and layered onto a cushion of Ficoll-Paque (Sigma). CTLs were collected from the interface between the cushion and the growth medium after centrifuging at 1200 rpm, 20 min. CTLs were washed in PBS and resuspended at $3-6 \times 10^7$ cells/mL were then ready to be plated out at Effector:Target ratios of 100:1-0.4:1.

Example 4

Immunofluorescence Cytometry

After IFN treatment, cells ($3 \times 10^5$) were incubated with an appropriate dilution (1×PBS containing 0.5% v/v FCS) of anti-monomorphic MHC Class I antiserum for 1 h on ice. After washing three times with 1×PBS/0.5% v/v FCS, anti-mouse FITC-conjugated antiserum (Silenus) was added and incubated for an additional 1 h on ice. The cells were again washed three times and incubated in fixative solution (1% v/v formaldehyde, 0.03% $NaN_3$ and 1 g/50 mL glucose) overnight and then analysed by flow cytometry using a Becton Dickinson FACS IV gated.

The methods used for analysing cells by immunofluorescence scanning on a FACSCalibur™ (Becton-Dickinson, Mountain View, Calif.) have been previously described. (see Wong et al., *J. Immunol.* 1998, 160: 5475-5484). Antibodies used were: Rat IgG2a, anti-murine B7-1 monoclonal antibody IG10, Phycoerythrin conjugated (Pharmingen, San Diego, Calif.); IgG2a, YN1/17.4 Rat anti-murine ICAM-1 monoclonal antibody (ATCC CRL1879, American Type Culture Collection, Rockville, Md.); Mouse anti-murine MHC H-2 $K^bD^b$ monoclonal antibody, ASH 1474 kindly supplied by Professor Ian MacKenzie, Austin Research Institute, Heidelberg, Melbourne).

Example 5

CD4/CD8 CTL Purification

Dynabead kits were used to separate and purify the different CD8+ and CD4+ CTL populations according to the manufacturer's instructions (Dynal Pty Ltd, Carlton South, Victoria, Australia).

Example 6

Figure 2:
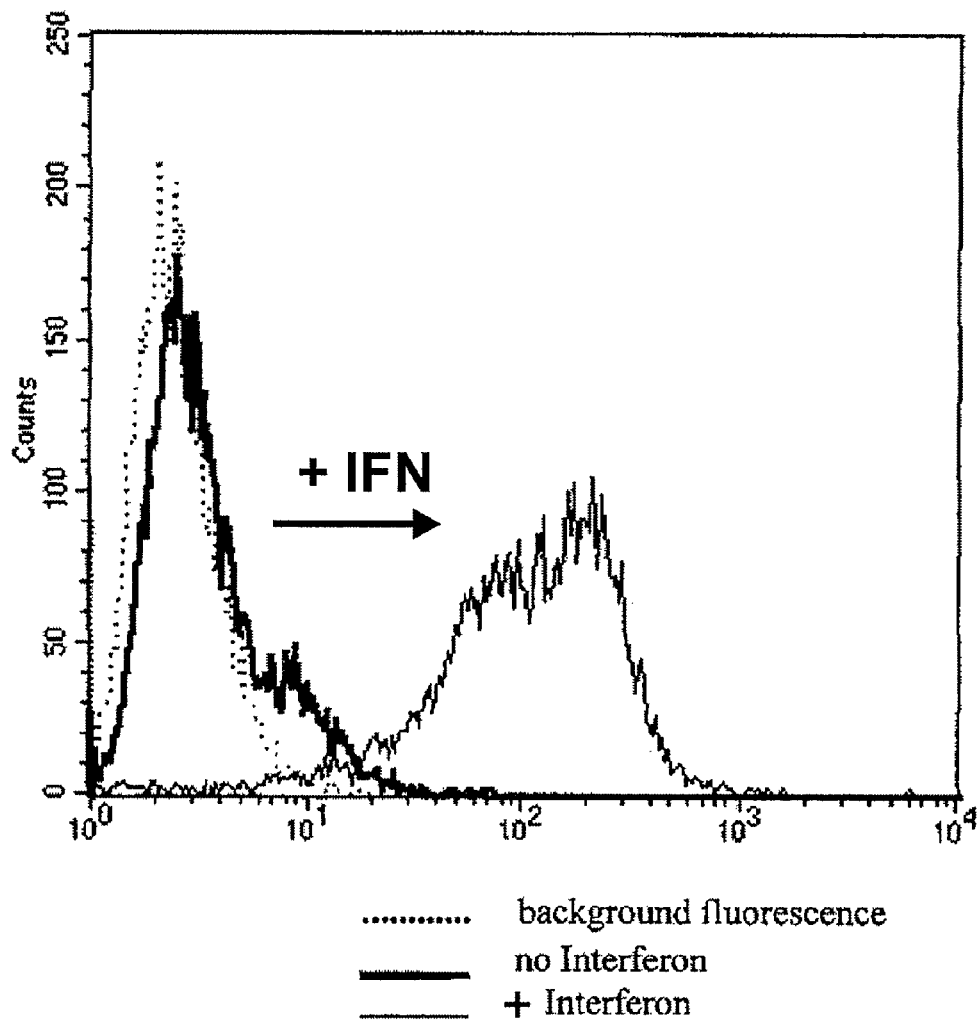
FIG. 2 is a graphical representation showing the effect of interferon treatment on MHC Class I expression on the surface of B16 murine melanoma cells.

Interferon Treatment Significantly Increases Cell Surface Levels of the CTL Reactive Receptor Molecules The B16 murine melanoma model is a close facsimile of advanced stage malignant melanoma in humans. As it was shown for human melanoma cell lines, treatment of the wild type B16 F10 cell line with either types of interferon resulted in significant increases in the levels of expression of MHC Class I antigens on the cell surface. Also, again as with the human melanoma cell lines, interferon gamma/beta treatment was found to consistently provide the highest increase in the expression of surface MHC class I molecules on the murine B16 melanoma cells. An example of the interferon-mediated increase in MHC class I immunofluorescence scanning profile of the stained cells in presented is FIG. 2. Note that B16 cells, in the absence of interferon treatment, exhibit low levels of MHC class I expression above non-specific background fluorescence. Large increases in expression of MHC class I were reproducibly obtained when cells were first primed with 1000 IU/mL-interferon gamma before treatment with interferon alpha (1000 IU/mL) for a further period. Typical results of a time course of induction by interferons and the relative increases in MHC Class I expression are presented in Table 1. It can be seen that the increases in MHC class I expression levels often were up to 100 times greater than that of control non-treated cell populations. Treatment with interferon gamma 72h/beta48h was selected as optimal because this treatment commonly produced the highest levels of class I expression and the levels then declined after long periods of interferon treatment.

Example 7

Figure 3:
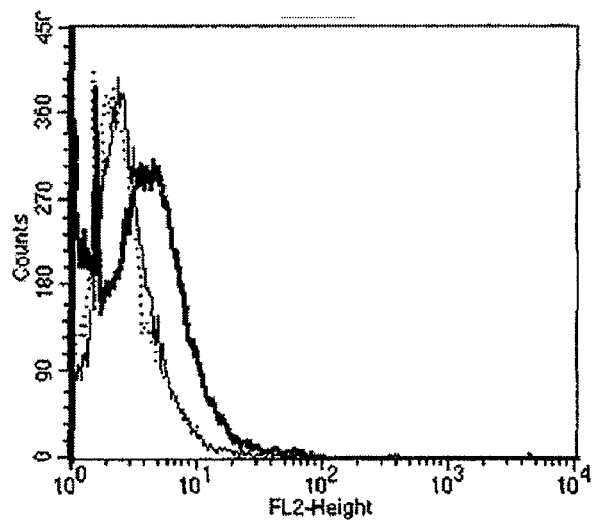
FIG. 3A is a graphical representation showing the levels of B7-1 on B16 wild type cells.
FIG. 3B is a graphical representation showing the levels of ICAM-1 on B16 wild type cells.
Figure 3:
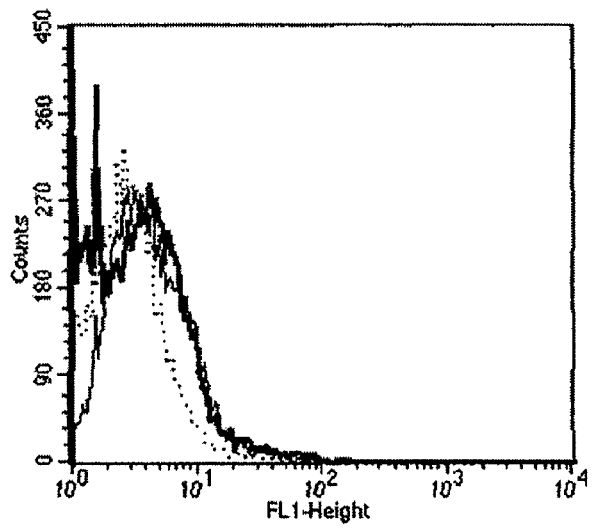

Interferon Treatment has a Small Effect on B7-1 or ICAM-1 Expression on B16 Cells The co-stimulatory molecule, B7-1 has been discussed above and shown to play a key role in stimulating activation and proliferation of CTLs. In the absence of B7-1 expression, CD3 activation results in death and subsequent loss of killer T cell function (32). B7-1 binds to the surface receptor, CD28 (33, 34, 35) and the combined signal of MHC class I with CD3 and B7-1 with CD28 drives the proliferative response expanding the representative clones of reactive CTLs. Levels of the B7-1 antigen and another molecule on B16, ICAM-1, also involved in T cell-cancer cell binding interactions were not greatly increased by treatment with interferon (FIG. 3). Occasionally, marginal increases (2-4 times control levels) in expression of B7-1 and ICAM-1 were detected but these were not routinely reproducible and at other times, no significant increase was found (Table 2a,b respectively). Others have also shown that B16 cells express low to undetectable levels of ICAM-1 or B7-2 (36, 37, 38). For this reason, and because the absence of B7 causes T cell loss, B16 cell lines were produced which expressed increased levels of B7-1 antigen.

Example 8

Production of Transfected B16 Cell Lines Expressing Increased Levels of B7-1

Figure 4:
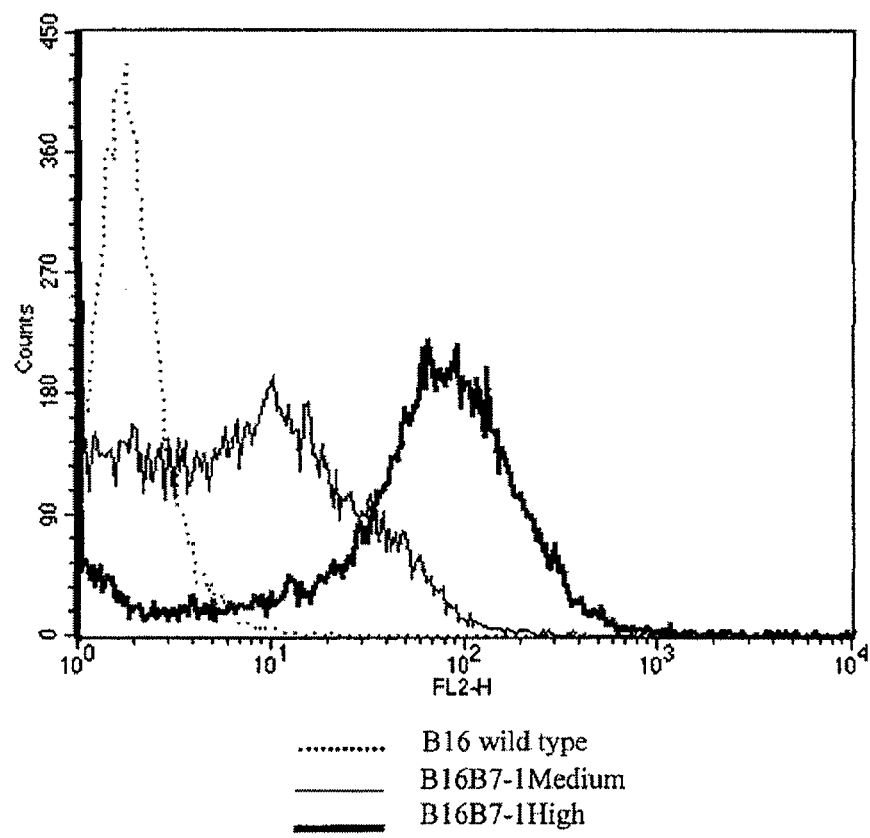
FIG. 4 is a graphical representation showing the levels of B7-1 on B16 cell lines transfected with a vector expressing B7-1.

The wild type B16-F10 cells deficient in B7 expression were found to be poor producers of CTL immune responses (see below). Therefore, sub-lines of B136-F10 cells were derived by transfection expressing high levels of B7 antigen. These lines were selected to constitutively express higher levels of B7-1 relative to wild type B16 cells. Two clonally derived B16-F10 cell lines transfected to express different levels of B-7 were produced and further investigated. Clone B7-1Med (with medium B7-1 expression levels) and B7-1Hi (with high expression were analysed by immunofluorescence scanning before and after interferon treatment (results presented in FIG. 4).

Example 9

Figure 5:
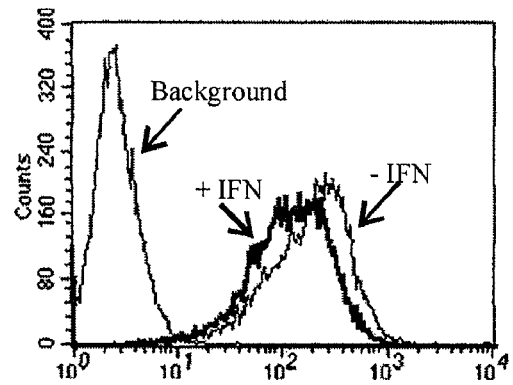
FIG. 5A is a graphical representation showing the levels of B7-1 on B16B7-1High cells are unaffected by interferon treatment.
FIG. 5B is a graphical representation showing the levels of ICAM-1 on B16B7-1High cells remain at similar levels relative to those on wild type B16 cells.
FIG. 5C is a graphical representation showing increased levels of MHC Class I on B16B7-1High cells relative to wild type B16 cells.
Figure 5:
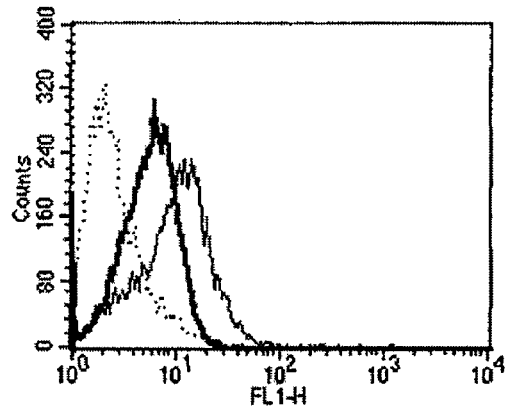
Figure 5:
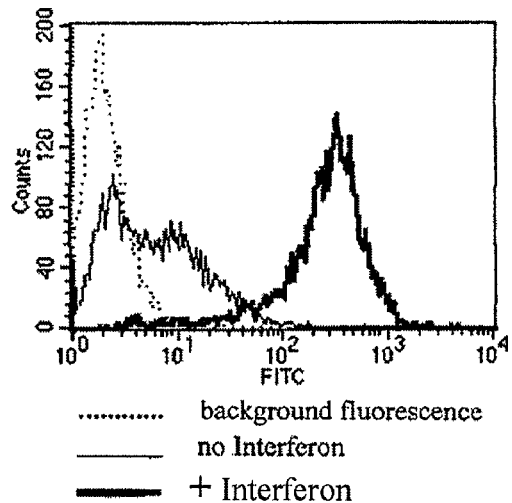

Increased Levels of Expression of MHC Class 1, B7-1 and ICAM-1 on B16 Cells Transfected with Murine B7-1 Antigen and Treated with Interferons The levels of B7-1 expression on these cloned lines remained unaffected by the different treatments of these cells with interferons. In addition, both of the B7-1 positive (B7+) cell lines generally retained their response to interferon treatment despite having been transfected. Similar increased levels of MHC Class I resulted after interferon treatment as before, but no significant increases in ICAM-1 were detected compared with the slight increase produced on wild type B16-F10 cells after optimal induction with interferons (FIG. 5).

Example 10

Treating Target Cells with Interferons Greatly Increases the Extent of Cytotoxic Lysis Detection of cell lysis in cytotoxic assays depends on the ability to induce adequate production of immune effector cells in mixed lymphocyte cultures (MLC) which include cytotoxic T lymphocytes, large granular lymphocytes or natural killer cells. These effector cells can then be assayed by their ability to lyse target cells loaded with an appropriate indicator such as 51-Chromium, luciferase or other molecules allowing detecting of membrane disruption or compromised target cell viability. The cytolytic reaction requires the effector cell to recognise and bind to the target cell via a series of coordinated complex interactions on the opposing cell surfaces that result in activation of the killing response. The low levels of immune cell populations resulting after in vivo immunisation are often insufficient to allow their immediate detecting in most in vitro assays. Thus, an interim preparatory step is required whereby population numbers of cytotoxic effector cells must first be amplified before assay in order that they are detected. This interim procedure commonly involves culturing cytotoxic immune effector cells derived from the host source in the presence of irradiated feeder/stimulator cells. Co-cultures also often include additional factors such as the cytokine interleukin-2 (IL-2) and antigen for the purpose of helping to expand the effector cell numbers by growth stimulation over a period of several days in culture.

During the procedure for assaying immunised mice for levels of cytotoxic responses, splenic lymphocytes are commonly harvested from the mice and then plated out into culture dishes together with irradiated feeder/stimulator cells. These cultures are incubated for about one week, often containing supplemented IL-2 and serve the purpose of inducing growth and increased numbers of immune cells to facilitate detecting of the cytotoxic effector cells. The inventors analysed the effects of pretreating cancer cells with interferons on the production of effector anti-cancer immune cells by using in vitro cytotoxicity assays. Thus, wild type B16 cells treated or not with interferons were compared by assaying their effects when used either as immunogens (single injection into mice), or as
stimulators added to MLC from injected mice (syngeneic or allogeneic) or as
51-Chromium-loaded target cells.

All cancer cell preparations used as stimulators were lethally irradiated before co-culture with the splenic derived effector populations in the absence of IL-2 as it was found that sufficient cytotoxic effector cell activity was produced without requiring additional IL-2.

Example 11

B7-1 Hi B16 Cells Produce Greater Immune Responses than the Wild Type B16 Cells

Figure 6:
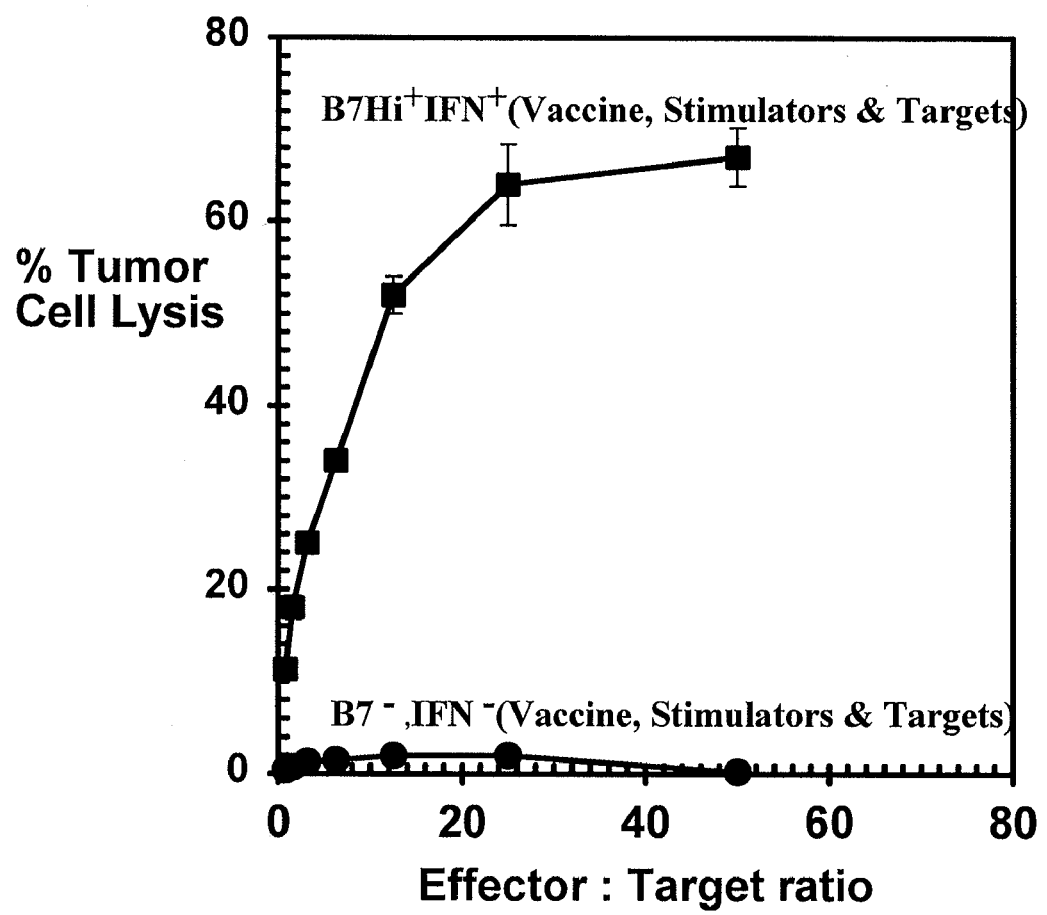
FIG. 6 is a graphical representation showing increased killing of tumour targets by CTL obtained from animals vaccinated with interferon treated B16B7-1High cells.

No significant anti-cancer immune cell activity was produced when the untreated wild type B16 melanoma cells were used as immunogen, stimulators and target cells as measured using the in vitro cytotoxicity assay (see FIG. 6). However, when the B7-1 highly expressing B16 cells were used throughout, significant anti-cancer immune cell activity was measured with 30% lysis at an effector to target ratio of 12.5:1. This result confirmed that the expression of B7-1 was important to stimulate the production of immune effector cells.

Example 12

Figure 7:
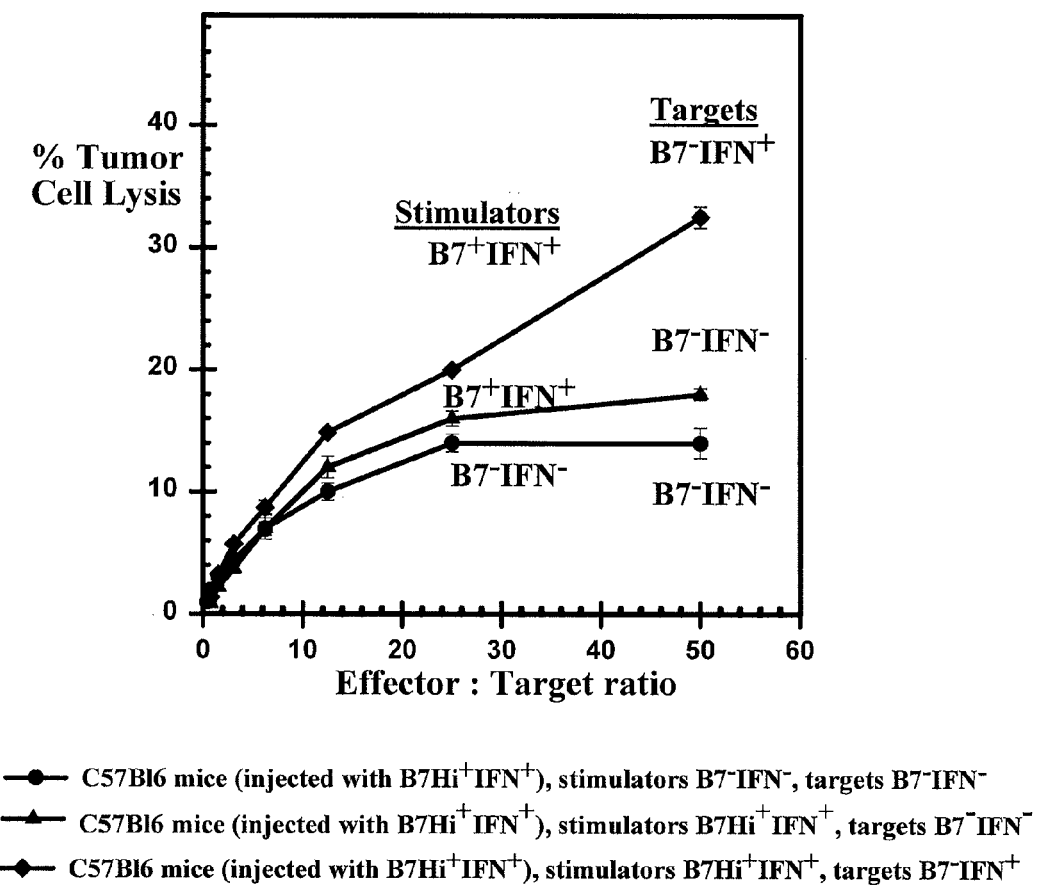
FIG. 7 is a graphical representation showing the effect of B7 expression and interferon treatment on stimulator populations and on target cells.

B7-1 Transfected B16 Cells Treated with Interferons and Used as Stimulators and/or Target Cell Populations Produce Significant Immune Responses A preparation of MLC from syngeneic mice immunised with interferon treated, B7-1 Hi B16 cells was divided into two portions. Each of these were amplified using either interferon treated B7-1Hi B16 cells (B7+, IFN+; FIG. 7) or wild type B16 stimulator cells not reacted with interferons (B7−, IFN−; FIG. 7). The immune responses were assayed using interferon treated wild type B16 cells as the targets for both MLC preparations. Use of the B7+, IFN+ stimulator cells resulted in a significant immune response above the level produced by B7−, IFN− stimulators. This result highlights the benefits obtained by using the interferon treatment of B7-1 positive cells in the immunopotentiating composition of the invention in order to produce an immune response against B7 negative cancer cell targets.

Example 13

Figure 8A:
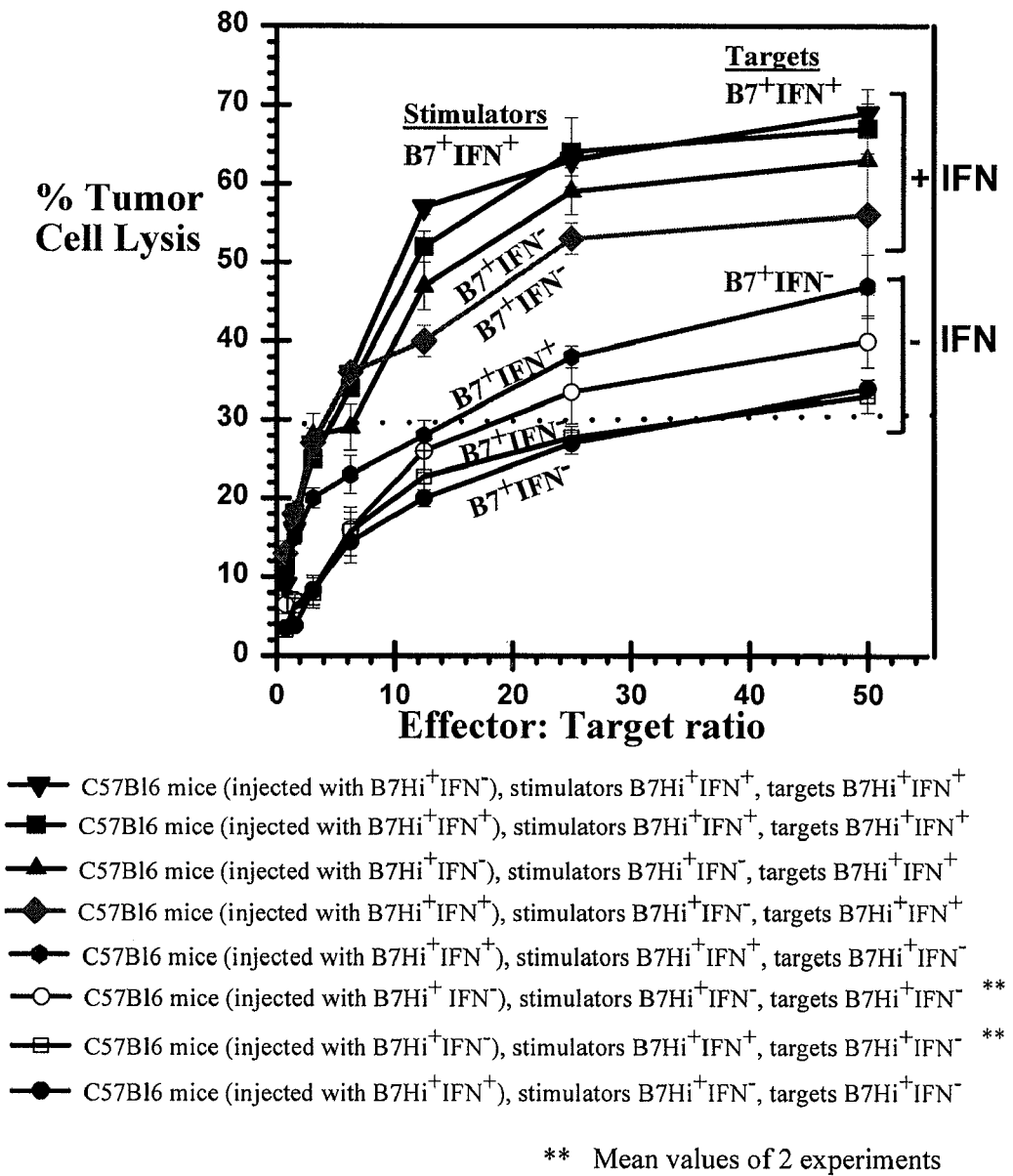
FIG. 8A is a graphical representation showing the combined effect of B7 expression and interferon treatment on the resulting in vitro CTL response.
Figure 8B:
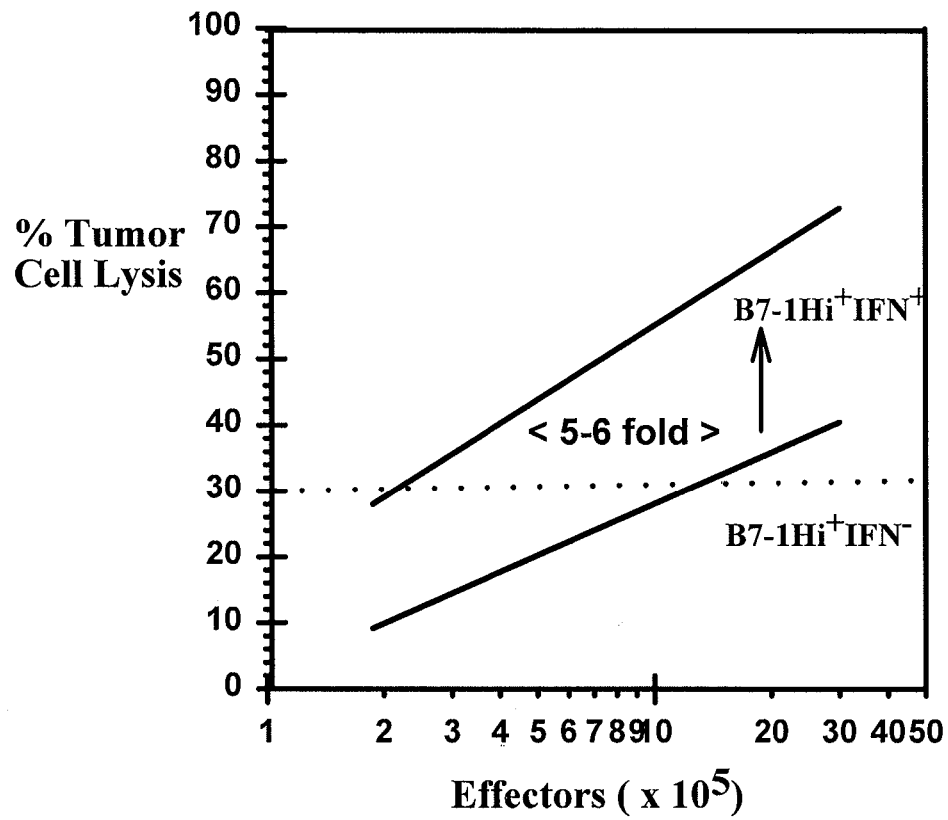
FIG. 8B is a graphical representation showing the combined effect of B7.1 expression and interferon treatment on the resulting in vitro CTL response.

Preparations Combining Interferon Treatment of B7 Positive Cells Provide Stronger Immune Cell Responses than those Obtained without Use of Interferon The results from a comparison of B7-1Hi B16 cells treated or not with interferon and used as stimulators and targets is presented in FIG. 8A (B7+, IFN+ vs B7+, IFN). Thus, when the B7Hi stimulators and target cells are treated with interferon (B7+, IFN+), significantly enhanced efficiencies of target cell killing (FIG. 8B; 5 times more lytic units calculated using the quantitative method outlined in [24]) result compared to those obtained using B7Hi B16 cells without interferon treatment (B7+, IFN−). Thus, reduced immune response resulted when B7 positive stimulators and target cells were not treated with interferon. Up to 60-70% lysis of target cells occurred at effector: target ratios of only 12.5:1 when the B7 positive stimulators and targets were interferon treated first (see FIG. 8). These results clearly demonstrate the beneficial impact of the treatment with interferon in the generation of strong immune responses when B7 positive cancer cells are used in the immunopotentiating composition.

Example 14

Figure 9:
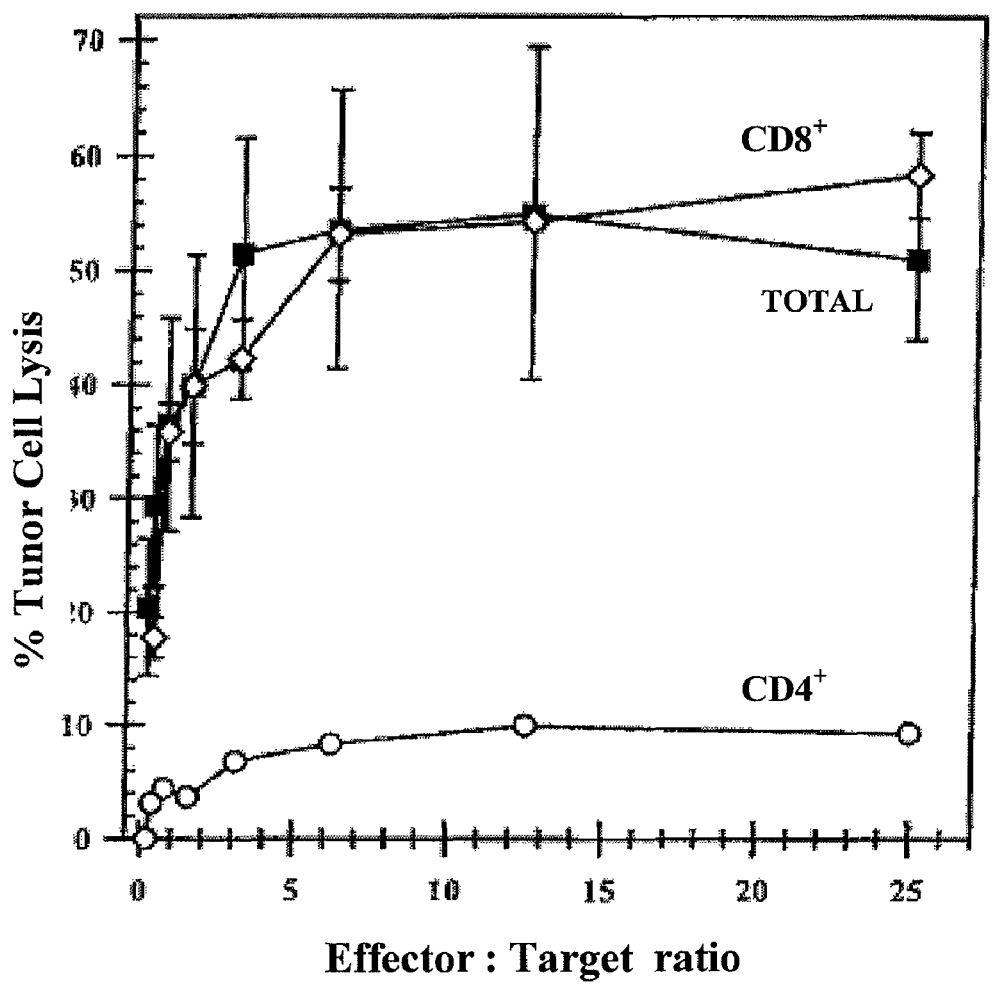
FIG. 9 is a graphical representation showing the immune effector population in the MLCs from mice vaccinated with B16-F10/B7-1$^{hi}$ cells comprises CD8+ CTLs. Samples of MLC populations prepared from mice vaccinated with B16-F10/B7-1$^{hi}$ cells were either used whole (-■-) or subjected to cell affinity purification with either anti-murine CD4 (-○-) or anti-CD8 (-◇-) mAbs on Dynabeads and the different cell populations assayed for in vitro cytotoxic activity using 51-chromium loaded B16-F10/B7-1$^{hi}$ cells as targets. Error bars ±S.D.

Cytotoxic Responses are Predominantly the Result of CD8 Positive T Lymphocyte Killer Activity Analysis of the type of immune effector cells which resulted from stimulation with the B16B7-1Hi interferon treated cells in MLC from syngeneic mice was carried out using Dynabeads™ and cell affinity purification with either IgG2a rat anti-murine CD4 (GK1.5, American Type Culture Collection TIB207, Rockville, Md.) or IgG anti-Cd8 (53-69.72, American Type Culture Collection TIB105, Rockville, Md.). The results presented in FIG. 9 revealed that the CD8 positive selected killer T cell population accounted for almost the entire immune effector cell species responsible for the anti-tumour cell cytolytic activity. No significant level of cytolytic activity was detected in the CD4 population. After affinity separation, no detectable cytolytic activity remained in the residual cell population either, indicating that all immune effector cells had been accounted for in the CD8 depleted population by this procedure.

Example 15

Figure 10:
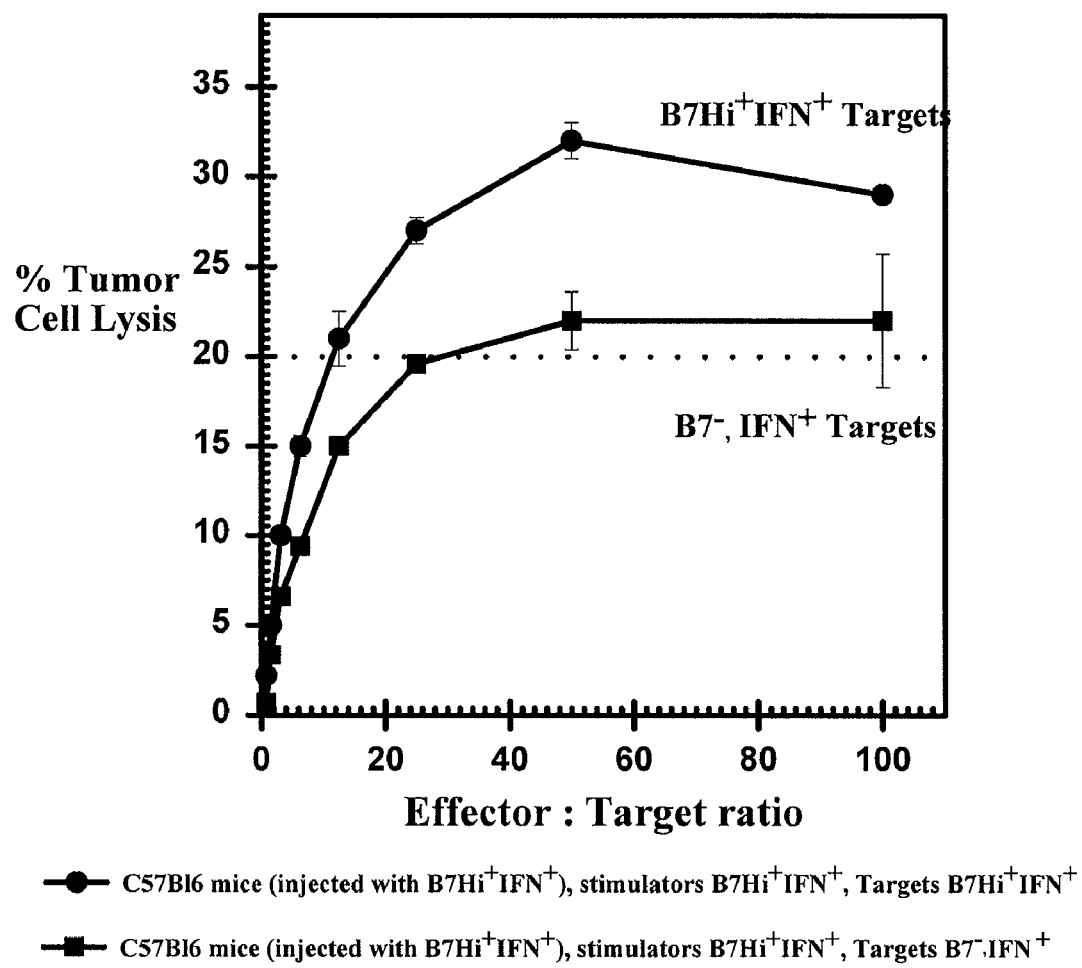
FIG. 10 is a graphical representation showing killing of different target cells by CTL obtained from animals vaccinated with interferon treated B16B7-1 High cells.

Expression of B7 on the Target Cancer Cells and their Treatment with Interferon is not Required to Obtain Efficient Killing The present inventors have established that strong immune responses to modified cancer cells can be produced. A key issue regarding the proposed immunopotentiating composition as a form of therapy is whether those immune effector cells induced are capable of recognising and efficiently killing endogenous cancer cells in the animal which lack B7 expression and have not reacted with interferon. The inventors, therefore, determined the effects of B7 expression and interferon treatment on the recognition and killing of target cells measured using the cytotoxicity assay. Firstly, the effect of B7 expression on target cells was examined. The target populations used were either B7Hi interferon treated cells (B7+, IFN+ targets) or wild type B16 cells treated with interferon (B7−, IFN+). The interferon treated B7-1 Hi vaccine was applied to syngeneic mice and interferon treated B7-1Hi stimulators (B7+, IFN+) were used and the MLC tested on the two different targets. The results are presented in FIG. 10. When wild type B16 (B7−, IFN+) cells were used as the targets, only 20% maximum lysis was obtained. However, a maximum lysis of 35% was obtained with interferon treated B16B7-1Med as targets. Quantitative comparison of relative lytic units [24] showed that B7 expression on the targets (B7+, IFN+) made them 3 times more susceptible to lysis than B7 negative cells (B7−, IFN+). Nevertheless, B7 negative target cells are efficiently lysed by the immune effector cells. When the targets tested were B16 wild type cells (B7−) treated or not with interferon (see FIG. 7), the results showed that B7-1 negative cancer cells not treated with interferon were still killed efficiently by MLC induced using the immunopotentiating composition. Comparing the relative lytic units for the interferon treated versus the untreated cancer cell targets, there was a 50% reduction in lytic efficiency against the target cells not treated with interferons B7−, IFN−. Thus, it can be concluded that even in situations where the cancer cells do not express B7 and have not been induced by interferon, they are still susceptible to efficient killing by immune cells induced using the immunopotentiating composition.

Example 16

Use of the Immunopotentiating Composition Produces Immune Responses in Syngeneic Mice Equivalent to those Obtained in Allogeneic Mice Immune cell responses are often severe in graft versus host rejection because these responses are induced against backgrounds involving considerable genetic differences between the grafted and the host immune systems. Allogeneic responses are commonly used as the hallmark standard for immune reactions because the genetic differences involved are usually large enough to provoke a strong immune response which can then be readily detected. For these reasons, the immunopotentiating composition of the invention was purposely compared for its ability to provoke comparatively strong anti-cancer immune killer cell responses in both syngeneic and allogeneic systems. For the allogeneic system, the Balb/c white mouse strain was used, which is genetically defined at the MHC locus as H-2d as opposed to the H-2b of the C57Black6 mouse strain from which the B16 melanoma is derived.

Figure 11:
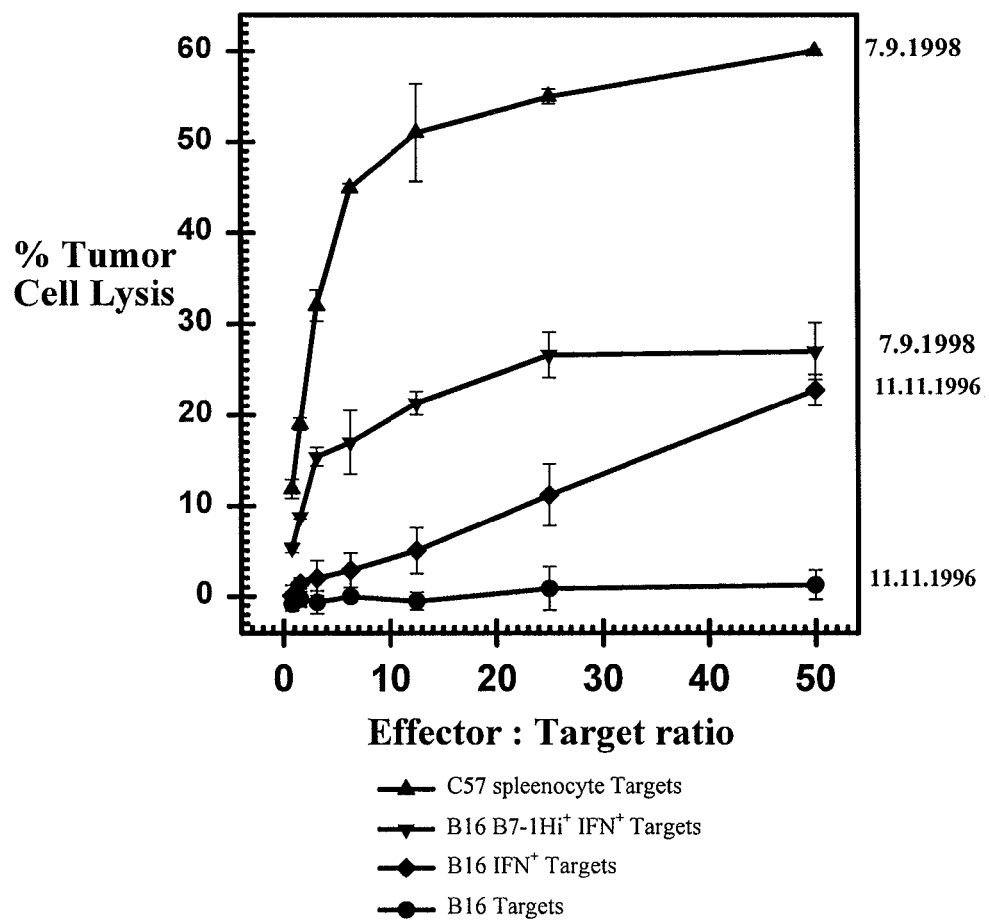
FIG. 11 is a graphical representation showing the results of analyses of CTL responses obtained when Balb/c mice were used as the allogeneic control system compared to the responses obtained in C57B16 syngeneic mice.

FIG. 11 shows the results from analyses of CTL responses obtained when Balb/c mice were used as the allogeneic control system compared to the responses obtained in C57B16 syngeneic mice. In the control allogeneic assays, MLC from Balb/c mice provided efficient killing [plateau at ~60% maximum lysis at effector:target ratio of 50:1 (7.9.98 FIG. 11)] of C57B16 splenocytes when they were used for both the stimulators and targets. When interferon treated B16 wild type cells (B7−IFN+) were substituted as the targets, allogeneic killing remained high, with results showing a similar profile in the lytic curve. However, no significant killing activity was detected when samples from the same allogeneic MLC population were assayed on the untreated B16 wild type target cells (B7−, IFN−, results not shown). Thus, interferon treatment also significantly improved allogeneic mediated cytotoxic lysis of wild type B16 target cells. Furthermore, interferon treated B16 wild type cells proved to be more effective targets than untreated B16 wild type cells in assays using either the allogeneic or syngeneic MLC, albeit that responses with syngeneic MLC were only detected at high effector: target ratios and resulted in much lower levels of cytolysis, <10% (FIG. 11). Much greater cytotoxic lysis was observed in all assays comparing interferon treated versus non-treated targets.

Figure 12:
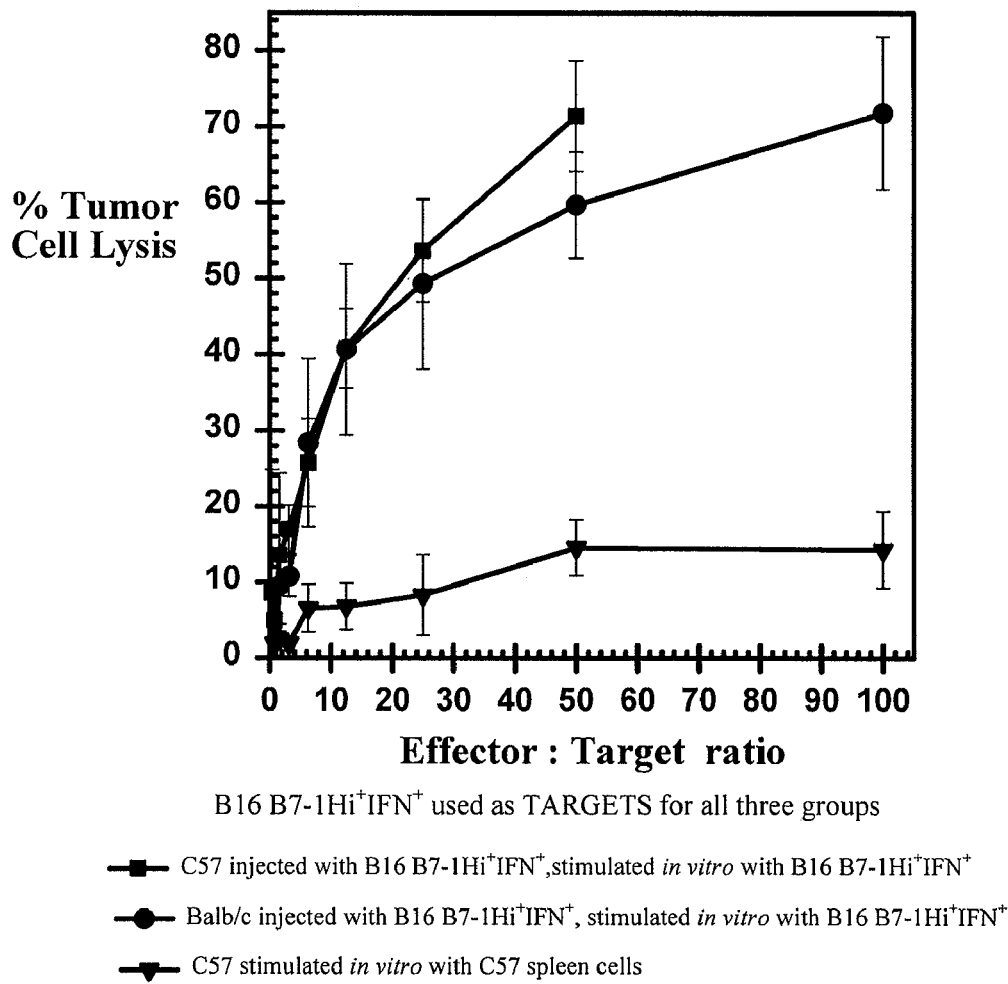
FIG. 12 is a graphical representation showing an example of a comparative analysis of the immune responses obtained in allogeneic versus syngeneic mice injected with the B7Hi interferon treated B16 vaccine, and analysed after stimulation on B7Hi interferon treated B16 cells using B7Hi interferon treated target cells.

FIG. 12 shows an example of a comparative analysis of the immune responses obtained in allogeneic versus syngeneic mice injected with the B7Hi interferon treated B16 vaccine, and analysed after stimulation on B7Hi interferon treated B16 cells using B7Hi interferon treated target cells. It can be seen from the cytotoxicity assay that the resulting immune responses induced in the two genetically different systems are very similar, both producing strong lysis of the target cells. This is confirmed by comparative analysis of the relative lytic units produced by each. The result was determined as $10^5$ effector cells/1 Lytic Unit (30% lysis) for both preparations (see reference (39)). Thus, using the optimal immunopotentiating composition described, the levels of response induced in syngeneic mice approach those normally only produced using allogeneic systems.

Example 17

Preclinical Trials Using the Immunopotentiating Composition as a Cancer Vaccine Treatment of cells with gamma interferon for 72 h and beta interferon for 48 h was shown to optimally induce increased levels of surface expression of MHC class I on melanoma cells, particularly on human melanoma cells. Levels of ICAM-1 and B7 antigens on the human cells were also elevated by interferon treatment. However, given the common loss of B7 expression on these cells, the immunopotentiating composition includes transfection to express B7-1 antigen. The transfected B7 expressing murine melanoma cells were shown to be unaltered in their responses to the optimal interferon treatment showing similar strong inductions of MHC Class I antigen. Results from studies with the B16 melanoma model showed the expression of B7-1 and interferon treatment were important for producing CD8 positive CTLs with potent cytolytic activity against B16 cancer cells and that these cells were capable of lysing target cells even though they did not express B7 antigen. Given the level of immunity shown to be induced by the B7Hi interferon treated B16 cells measured by cytotoxicity assay, the same cell preparations were tested for their ability to induce anti-cancer immunity in whole animals when injected as a vaccine. The protocol compared the use of B7Hi/B16 transfected cells to vaccination with wild type B16 cells. The cells were irradiated and cohorts of mice were vaccinated by intraperitoneal injection weekly for up to six weeks. Vaccinated mice were challenged at week 7 with an injection subcutaneously on the rear flank with $5 \times 10^5$ B7Med B16 cells. The results from this trial are presented in FIG. 13. All twenty control animals receiving only the challenge cancer cells succumbed to a 2 cm tumour growth by day 38. However, mice vaccinated with the B7Hi interferon treated immunopotentiating composition produced the greatest resistance to the challenge with 90% (18 out of 20 mice) surviving with no sign of tumour and continued to remain tumour free thereafter. The other trial cohorts showed different levels of immunity, with less successful outcomes [refer to FIG. 13 for details]. Thus, it can be concluded that the B7Hi/interferon treated immunopotentiating composition induced potent CD8 positive CTL responses and these were capable of providing sufficient immunity to protect the majority of vaccinated mice from the cancer cells.

Example 18

Heterogeneous Antigenic Vaccine

Either autologous or MHC matched allogeneic cells are chosen. The cells are propagated and maintained in culture. Populations of cells ($1-2 \times 10^6$/mL) are pre-treated with high levels of gamma-interferon (500-1000 IU/mL) for 16-24 h before challenge with high levels of Type I interferon (500-1000 IU/mL) for 24-48 h until maximal expression of MHC class 1 molecules including B-7 is detected. The cells are treated by, for example, irradiation or other suitable means to destroy replicative ability under conditions to be established for the particular cells. The cell preparation may include adjuvants such as ISCOMS (trademark) and bacterial products at therapeutic doses. The vaccines are then injected subcutaneously or intramuscularly. Successive doses of the vaccine are prepared fresh and injected weekly over several weeks until the cytotoxic T-cell response of the recipient to the non-interferon treated cells is significantly elevated.

Example 19

Targeted Antigenic Vaccine

Either autologous or MHC matched allogeneic cells are chosen. The cells are propagated and maintained in culture. Populations of cells ($1-2 \times 10^6$/mL) pre-treated with high levels of gamma interferon (500-1000 IU/mL) for 16-24 h before challenge with high levels of Type I interferon (500-1000 IU/mL) for 24-48 h until maximal expression of MHC class I molecules is detected. The cells are then subjected to acid elution of peptide epitopes from the MHC surface molecules using washing with cold acid buffers (0.131M citrate, 0.066M $Na_2HPO4$, pH 3.0) for 1 minute at 4° C. The cells are washed with cold PBS and then incubated in the presence of specific peptide antigens and beta-2-microglobulin. The cells are then treated by, for example, irradiation or other suitable means to destroy replicative ability under conditions to be established for the particular cells. The cell preparation may include adjuvants such as ISCOMS™ and bacterial products at therapeutic doses. The vaccines are then injected subcutaneously or intramuscularly. Successive doses of the vaccine are prepared fresh and injected weekly over several weeks until the cytotoxic T-cell response of the recipient to the non-interferon treated cells is significantly elevated.

Example 20

Assessment of Responsiveness of Melanoma Cells to Interferon Treatment

The present inventors have established that deficient levels of Stat1 exist in IFN-resistant skin melanoma cells at low passage in culture. Immunofluorescence cytometry detects relative levels of Stat1 expression. This analysis provides a way of analysing samples of melanoma cells directly harvested and prepared from patients' tumours. Thus, cells from the melanoma lines are permeabilised and fixed as outlined in (38), before immunostaining with a specific murine IgG1 anti-Stat1 monoclonal antibody and detection using an FITC-conjugated affinity purified sheep-anti-mouse Ig secondary antibody. The samples are counterstained with a melanoma specific marker. The murine IgG2a chondroitin sulfate proteoglycan (MCSP) as a melanoma specific marker. Isotype matched control mouse Ig is used for control immunostaining of cell samples. Immunostained cell samples are analysed using an immunofluorescence cytometer, for example a FACSCalibur™ (Becton-Dickinson). The development of this technique provides improved specificity and sensitivity when determining the levels of Stat1 expression and their variation directly in the tumour cells extracted from the patient melanoma samples. This information is useful for determining whether potentially IFN resistant cancer cells exist in the patient's tumour samples in vivo. Direct samples of primary melanoma for this analysis either as 3 mm punch biopsies from anaesthetised skin or thin needle aspirates providing at least $10^6$-$10^7$ melanoma cells per sample, is more than sufficient for the analyses. This assay provides information on responsiveness of melanoma cells to IFN in relation to the staging of development of melanoma and patient responses.

Example 21

Figure 14A:
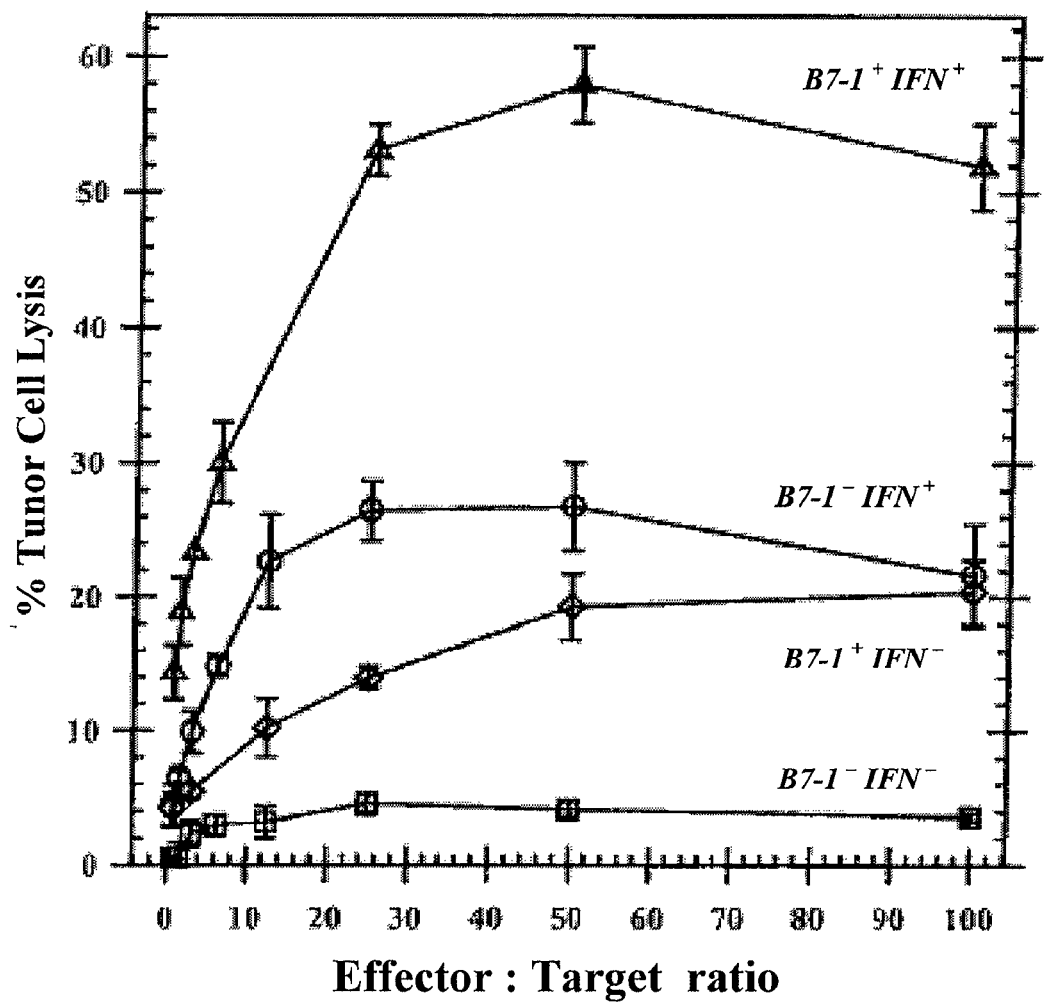
FIG. 14A is a graphical representation showing the effects of IFN-gamma/-beta treatment and B7-1 expression on the susceptibility of B16-F10 cells to cytotoxic killing. MLCs prepared from mice vaccinated with B16-F10/B7$^{hi}$ cells were examined for their ability to kill preparations of B16-F10 target cells differing in their expression of B7-1 and treatment with IFNs and were measured using in vitro cytotoxicity assays. Error bars ±S.D. The target cells were as follows: control untreated B16-F10 cells (-◇-); B16-F10 cells treated with IFN-gamma/-beta (-○-); B166-F10/B7$^{hi}$ cells (-□-) and B16-F10/B7-1$^{hi}$ cells treated with IFN-gamma/-beta (-Δ-).
Figure 14B:
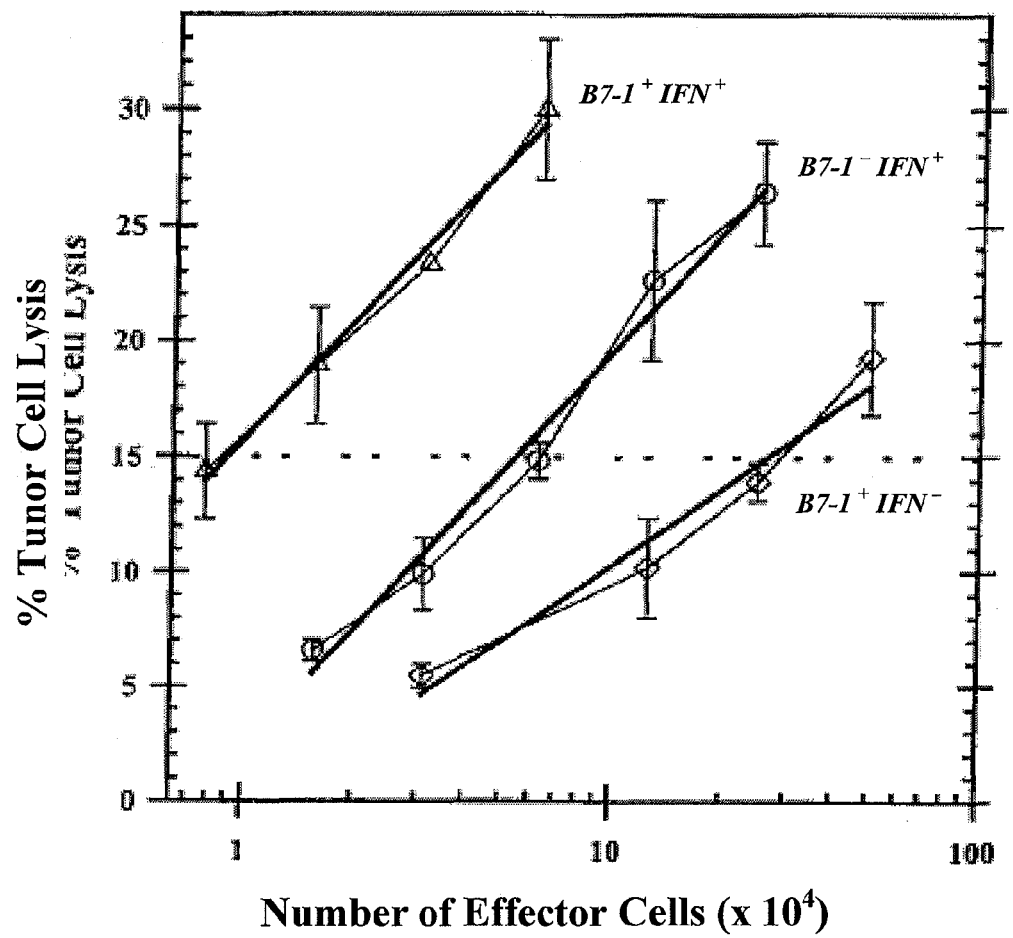
FIG. 14B is a graphical representation showing quantitative comparison of the susceptibility of different B16-F10 cell preparations to cytotoxic activity derived from mice vaccinated with IFN-gamma/-beta treated B16-F10/B7-1$^{hi}$ cells. The results in A were analysed according to the method of Wunderlich and Shearer (41) with one lytic unit defined as the relative number of effectors required to produce 15% cytolysis. Error bars ±S.D. The target cells were as follows: B16-F10 cells treated with IFN-gamma/-beta (-○-); B16-F10/B7-1 µl cells (-□-); B16-F10/B7-1$^{hi}$ cells treated with IFN-gamma/-beta (-Δ-).

B7-1 Transfected B16-F10 Cells Treated with IFNs as Target Cell Populations are More Highly Susceptible to CTL-Mediated Cytotoxicity Analysed by in Vitro Assay Given the marked increase in tumour cell killing activity obtained in mice receiving the IFN-gamma/-beta treated B16-F10/B7-1$^{hi}$ cell vaccine (FIGS. 6-9), the effectors derived from these mice were analysed further. An assessment of the relative contributions of each of the modifications, B7-1 expression versus IFN treatment on the extent of killing was made. Thus, MLCs were compared for their ability to kill B16-F10 tumour cell target preparations differing in their expression of B7-1 and IFN-gamma/-beta treatment. When control B16-F10 (B7-1 negative, non-IFN treated) cells were used as targets, low levels of CTL activity were detected albeit that the resulting levels of cell killing varied slightly between 0 to ~5% of maximum lysis over eight separate experiments (an example curve is shown in FIG. 14A). IFN-gamma/-beta treated B16-F10 cells used as targets provoked a greater cell killing response (between 15-22% maximum lysis), consistently well above the levels of killing of control B16-F10 cells not treated with IFN. Quantitative comparison of the relative killing of targets based on the method outlined in (41) could not be made because of the low level of killing of the control B16-F10 cells. Results from repeated experiments comparing the effect of B7-1 expression on the B16-F10 target cells treated with or without IFN-gamma/-beta are presented in FIG. 14A. Thus, IFN-gamma/-beta treated B16-F10/B7-1$^{hi}$ cell targets were compared with non-treated B16-F10/B7-1$^{hi}$ cell targets. The results revealed plateaus of cell lysis of between 60-70% for the IFN-gamma/-beta treated B7-1$^{hi}$ cells. These values were much higher compared to the range of values (between 15-40%) obtained in several different experiments using non-treated B16-F10/B7-1$^{hi}$ cells as targets. Quantitative analysis of the relative lytic units from the results in FIG. 14A revealed that the combination of high B7-1 expression and IFN-gamma/-beta treatment of B16-F10 cells increased their cytolysis by nearly sixfold (FIG. 14B) over the killing of B 16-F10 cells treated with IFN-gamma/-beta. In addition, the latter cells were killed almost fivefold more efficiently than B16-F10/B7-1$^{hi}$ target cells not treated with the IFNs. Thus, the IFN treatment resulted in an overall ~27 fold increase of killing of B7-1 positive B16-F10 cells.

On the basis of these results, it can be concluded that B7-1 negative B16-F10 cells not treated with IFN were killed at low efficiency by cytotoxic immune effector cells resulting from the use of an immunogenic vaccine comprising IFN-gamma/-beta treated B16-F10/B7-1$^{hi}$ cells. In addition, expression of B7-1 together with the effects of IFN-gamma/-beta treatment on the target tumour cells greatly enhances the ability of CTLs to bind and kill these tumour cells.

Example 22

Figure 15:
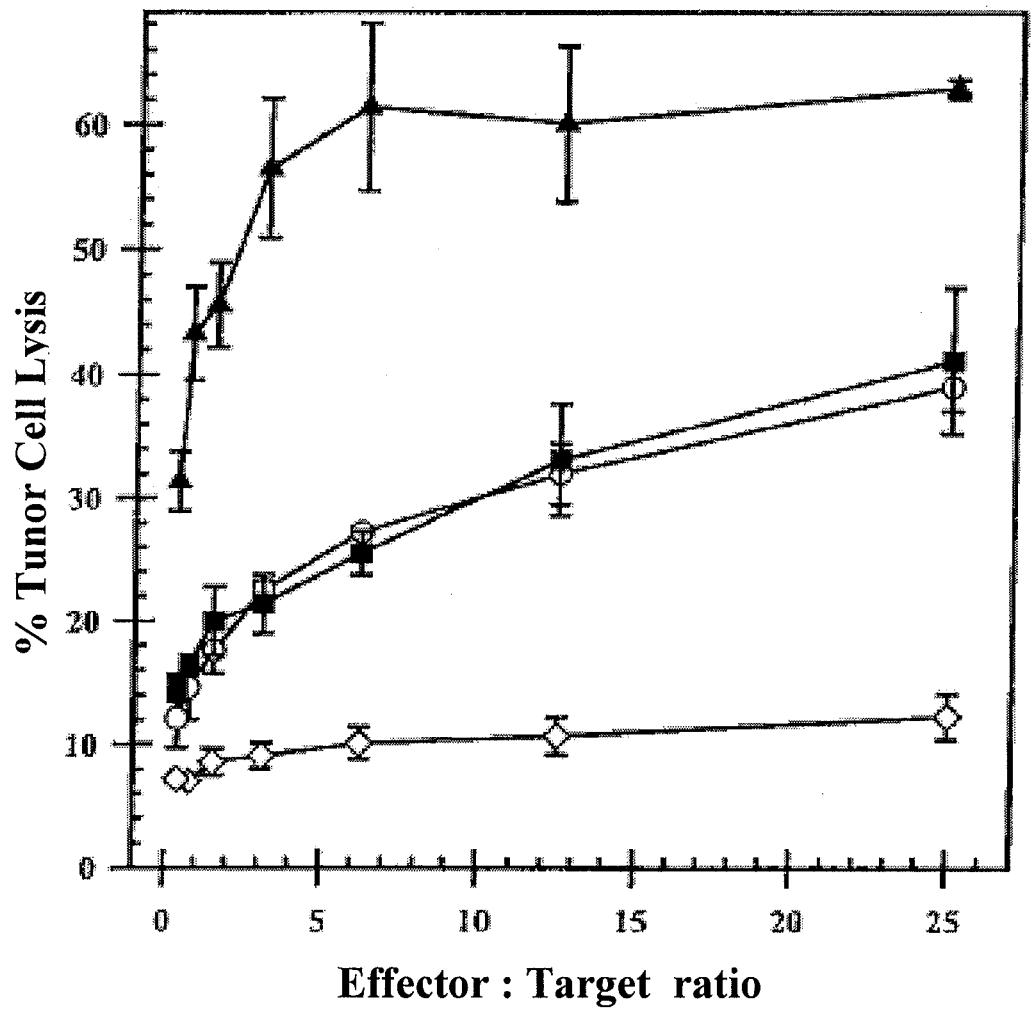
FIG. 15 is a graphical representation showing MLC cytotoxic effector cell specificity for B16-F10 melanoma versus syngeneic EL-4 thymoma cell target populations. MLCs from age and sex matched C57BL/6Jmice vaccinated with either EL-4 cells or with IFN-gamma/-beta treated B16-F10/B7-1$^{hi}$ cells were tested by in vitro cytotoxicity assay for their ability to kill different target cell populations. Error bars ±S.D. The target cells were as follows: IFN-gamma/-beta treated B16-F10/B7-1$^{hi}$ cell vaccine, stimulators and target cells (-▲-); EL-4 cell vaccine and stimulators, IFN treated B16-F10/B7-1$^{hi}$ target cells (-■-); IFN-gamma/-beta treated B16-F10/B7-1$^{hi}$ cell vaccine and stimulators, EL-4 target cells (-○-); EL-4 cell vaccine, stimulators and target cells (-◇-).

CD8$^+$ T Cells Produced are Specific for B16-F10 and Not Syngeneic EL-4 Thymoma Cells When syngeneic EL-4 thymoma cells were tested and compared with B16-F10 melanoma cells as targets, the results in two separate experiments showed a low level of cytolysis of EL-4 target cells, more noticeably at the higher E:T ratios >6:1 (see FIG. 15). However, based on lytic unit analysis (results not shown) the susceptibility of EL-4 target cells to cytolysis was quantitatively estimated to be tenfold lower than the killing of the B16-F10/B7-1$^{hi}$ cells. Thus, the CTL reactivity towards the syngeneic EL-4 thymoma cells was considerably lower.

Discussion of the Examples

The immunopotentiating composition has been designed and established to enhance the production of cytolytic anti-tumour cell activity in animals. When the appropriate combination of modifications is applied, significant gains in killer cell activity by as much as 5-20 times can be produced. The techniques involve the use of recombinant interferons that are readily available now from commercial sources. The procedure was designed on the basis of theoretical principles derived from observations that the properties of the interferons include many aspects related to increasing the antigen processing and presentation of cells. Focusing on three of the most important surface components, ICAM-1, B7-1 and MHC Class I, the effect of gamma priming, and Stat1 upregulation enabled us to formulate the subject immunopotentiating composition. Firstly, fluorescence analysis of cells treated with either type I or type II interferons alone or in combination allowed us to determine the optimal treatments inducing the highest simultaneous expression of MHC Class I, B7-1 and ICAM-1 receptors required for efficient CTL responses. Thus, interferon gamma for 72 h and interferon beta for 48 h, including a 24 h priming incubation with interferon gamma produced values of MHC class I and ICAM-1 expression close to the maxima plateau level. Surface expression levels then declined over longer time periods of incubation.

In the case of the B16 murine melanoma cell line, however, despite the large increase in surface expression of MHC Class I and ICAM-1 molecules, no B7-1 was detected. This is likely to be a common problem given that many cancers are B7 negative (for example, see (40)). For this reason, the inventors adopted the practice of transfecting cancer cells to express the B7-1 antigen. The important role played by B7-1 and its action as a co-stimulatory molecule signalling through the CTL CD28 receptor has been previously well established in other studies both in vitro and in vivo in promoting CTL survival and expansion as opposed to T cell anergy in the absence of B7-1 (34, 35). Interestingly, despite the absence of detectable B7-1 on the surface of the interferon treated wild type B16-F10 cells, these cells proved to be much better targets than the untreated wild type B16-F10 cells (FIGS. 6-9). This result held not only for the syngeneic, but also for allogeneic MLC (FIGS. 11, 12). Thus, the combination of interferon treatment and B7-1 are important for the induction of sufficient immune responses to allow efficient killing of the target cancer cells.

The modifications involved in producing B7-1 expressing B16-F10 cells by transfection with selectable expression vectors did not affect the ability of the interferon treatments to induce comparable increases in the levels of ICAM-1 and MHC Class I expression on the selectable B7-1 positive clones (FIG. 5). This was important as it then allowed us to compare interferon treated B7-1 positive with the B7-1 negative wild type B16-F10 cell lines for the propensity to act as efficient stimulators and/or target cells. The effect of B7-1 expression was very significant and cells treated with interferons, when used as immunogen, MLC stimulators and as targets yielded efficiencies of cytolytic responses similar to those obtained with allogeneic MLC on interferon treated B16 cell preparations.

Figure 13:
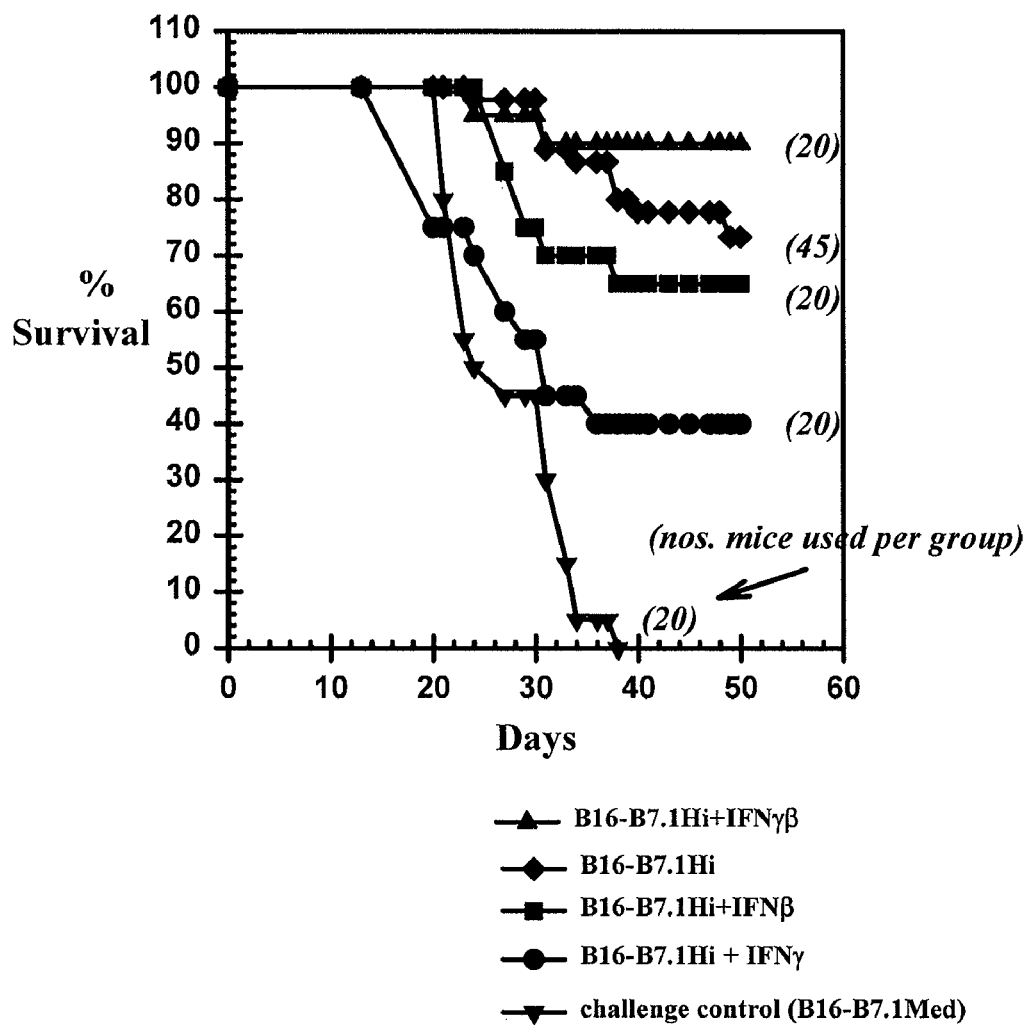
FIG. 13 is a graphical representation showing the results of preclinical trials using the immunopotentiating composition of the invention as a vaccine.

The results of the cytotoxicity assays showing the importance of the combined interferon treatment and B7 expression in the immunopotentiating composition should be considered together with the outcomes of the preclinical trial. Although the B7Hi vaccine alone did protect 70-75% of the animals, it was not as good as the outcome of 90% with the interferon combined (FIG. 13). The cytotoxicity assays showed a considerable improvement with a gain of 5 times greater activity using the interferon combination compared to without interferon. On balance, it can be concluded that the best formulation comprises combined interferon treatment and B7 expression in order to maximise antigen presenting function of the tumour cells thereby providing an optimal immunopotentiating vaccine that promotes high levels of anti-tumour CTL activity and protection of vaccinated mice from challenge with tumour cells.

The disclosure of every patent, patent application, and publication cited herein is hereby incorporated herein by reference in its entirety.

The citation of any reference herein should not be construed as an admission that such reference is available as "Prior Art" to the instant application Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

Tables

TABLE 1

Induction of MHC Class I antigen expression on B16-F10 by IFNs

| Time course of IFN treatment (h) | Mean fluorescence (ungated values)* | Mean fluorescence (gated values)** | % popln gated | Factor increase over control (ungated) |
|---|---|---|---|---|
| No IFN Control | 11 ± 1 | | | 1 |
| IFNγ (24) | 617 ± 5 | 642 | 97 | 55 |
| IFNγ (48) | 915 ± 0 | 940 | 99 | 81 |
| IFNγ (72) | 758 ± 3 | 833 | 92 | 67 |
| IFNγ (96) | 905 ± 5 | 1057 | 87 | 80 |
| IFNβ (24) | 269 ± 5 | 293 | 97 | 24 |
| IFNβ (48) | 202 ± 2 | 220 | 99 | 18 |
| IFNβ (72) | 330 ± 4 | 365 | 94 | 29 |
| IFNβ (96) | 29 ± 2 | 73 | 44 | 3 |
| IFNγ(48)β(24) | 862 ± 4 | 993 | 88 | 76 |
| IFNγ(72)β(48) | 1336 ± 10 | 1381 | 98 | 118 |
| IFNγ(96)β(72) | 635 ± 4 | 683 | 95 | 56 |
| IFNγ(120)β(96) | 935 ± 5 | 1060 | 89 | 83 |

*Mean ± standard error from three experiments.
**Gated values were obtained by subtracting the immunofluorescence peak profile of control untreated cells from the profile of cells treated with IFN as indicated.

TABLE 2A

Induction of B7-1 antigen expression on B16-F10 by IFNs

| Interferon treatment time course (hours) | Mean fluorescence (ungated values) | Mean fluorescence (gated values)* | % popln gated | Factor increase over control (ungated) |
|---|---|---|---|---|
| No IFN Control | 8 | | | 1 |
| IFNγ (24) | 36 | 77 | 47 | 5 |
| IFNγ (48) | 30 | 75 | 40 | 4 |
| IFNγ (72) | 6 | 80 | 6 | 1 |
| IFNγ (96) | 13 | 40 | 27 | 2 |
| IFNβ (24) | 30 | 102 | 28 | 4 |
| IFNβ (48) | 12 | 79 | 14 | 2 |
| IFNβ (72) | 5 | 58 | 6 | 1 |
| IFNβ (96) | 8 | 63 | 11 | 1 |
| IFNγ(48)β(24) | 35 | 76 | 44 | 4 |
| IFNγ(72)β(48) | 22 | 63 | 32 | 3 |
| IFNγ(96)β(72) | 6 | 73 | 6 | 1 |
| IFNγ(120)β(96) | 20 | 54 | 34 | 3 |

*Gated values were obtained by subtracting the immunofluorescence peak profile of control untreated cells from the profile of cells treated with IFN as indicated.

TABLE 2B

Induction of ICAM-1 antigen expression on B16-F10 by IFNs

| Time course of IFN treatment (h) | Mean fluorescence (ungated values)* | Mean fluorescence (gated values)** | % popln gated | Factor increase over control (ungated) |
|---|---|---|---|---|
| No IFN Control | 6 ± 2 | | | 1 |
| IFNγ (24) | 34 ± 14 | 64 ± 13 | 60 | 6 |
| IFNγ (48) | 19 ± 7 | 51 ± 8 | 42 | 3 |
| IFNγ (72) | 14 ± 6 | 49 ± 10 | 29 | 2 |
| IFNγ (96) | 19 ± 9 | 49 ± 9 | 44 | 3 |
| IFNβ (24) | 16 ± 7 | 45 ± 7 | 40 | 3 |
| IFNβ (48) | 15 ± 8 | 56 ± 11 | 31 | 3 |
| IFNβ (72) | 10 ± 6 | 65 ± 15 | 18 | 2 |
| IFNβ (96) | 11 ± 4 | 47 ± 5 | 27 | 2 |
| IFNγ(48)β(24) | 30 ± 8 | 56 ± 10 | 42 | 5 |
| IFNγ(72)β(48) | 28 ± 13 | 63 ± 15 | 49 | 5 |
| IFNγ(96)β(72) | 21 ± 10 | 54 ± 14 | 42 | 4 |

*Mean ± standard error from three experiments.
**Gated values were obtained by subtracting the immunofluorescence peak profile of control untreated cells from the profile of cells treated with IFN as indicated.

Bibliography

1. Isaacs, A and J Lindermann (1957) *Proc. R. Soc. Lond.* (*Biol.*) 147: 258-267.
2. Petska, S, J A Langer, K C Koon and C E Samuel (1987) *Annu. Rev. Biochem.* 56: 727-777.
3. Stark G R, Kerr I M, Williams B R, Silverman R H, Schreiber R D. (1998). How cells respond to interferons. *Annu. Rev. Biochem.* 67: 227-264.
4. Hague, S. and Williams B. Signal transduction in the interferon system. (1998) *Semin. Oncol.* 25: 14-22.
5. Wilks, A F and A G Harpur (1994) *Bioessays* 16: 313-320.
6. Wong, L. H., Hatzinisiriou, I., Devenish, R. J. and Ralph, S. J. (1998) Interferon-gamma-priming up-regulates ISGF3 components, augmenting responsiveness of IFN-resistant melanoma cells to type 1 interferons. *J. Immunol.*, 160: 5475-5484.
7. Wong, L. H., Krauer, K., Hatzinisiriou, I., Estcourt, M. J., Hersey, P., Tam, N., Edmondson, S., Devenish, R. and Ralph, S. (1997) Interferon-resistant human melanoma cells are deficient in ISGF3 components, STAT1, STAT2 and p 48-ISGF3γ. *J. Biol. Chem.* 272: 28779-28785.
8. Ralph, S. J., Wong, L. H., Hatzinisiriou, I., Estcourt, M., Hersey, P. and Devenish, R. J. (1998) Revising interferons-prodigies among the cytokines. *Today's Life Sciences*, 10: 37-43.

9. De Maeyer, E. and De Mayer-Guignard, J. (1988). Chpt 14 in "Interferons and other regulatory cytokines." John Wiley & Sons, New York, N.Y.
10. Kaplan D H et al. (1998). Demonstration of an interferon gamma-dependant tumor surveillance system in immuno-competent mice. *Proc. Natl. Acad. Sci. USA* 95: 7556-61.
11. Colamonici, O, P Domanski, L C Platanias and M O Diaz (1992) *Blood* 80: 744-749.
12. Heyman, M D Graders, K Brondum-Nielsen, B Cederblad, Y Liu, B Xu and S Einorn (1994) *Leukemia* 8: 425-434.
13. Billard, C, F Sigaux, S Castaigne, F Valensi, G Flandrin, L Degos, E Falcoff and M Aguet (1986) *Blood* 67: 821-827.
14. Pferrer, L M and D B Donner (1990) *Cancer Rec.* 50: 2654-2659.
15. Aman, P and A von Gabain (1990) *EMBO J.* 9: 147-152.
16. Kanda, D, T Decker, P Aman, M Wahlstrom, A von Gabain and B Kallin (1992) *Mol. Cel Biol.* 12: 4930-4936.
17. Dron, M and M G Tovey (1993) *J Interferon Res* 13: 377-383.
18. Xu, B, D Grander, O Sangfeld and S Einhom (1994) *Blood* 84: 1942-1949.
19. Johns, T G, I R Mackay, K A Callsiter, P J Hertzog, R J Devenish and A W Linnane *J. Natl. Cancer Inst.* 84: 1185-1190.
20. Wines, B D, C C Choe, I Hatzinisiriou, R J Devenish, A W Linnane and S J Ralph (1993) *Biochem. Mol. Biol. Int.* 31: 1111-1120.
21. Johns T G, Mackay I R, Callister K A, Hertzog P J, Devenish R J, Linnane A W. (1992). Antiproliferative potencies of interferons on melanoma cell lines and xenografts: higher efficacy of interferon beta. *J Natl Cancer Inst* 84: 1185-1190.
22. Lehtonen, A., Matikainan S., Julkunen, I. (1997). Interferons up-regulate Stat1, Stat2, and IRF family transcription factor gene expression in human peripheral blood mononuclear cells and macrophages. *J. Immunol.* 159: 794-803.
23. Sims, S., et al. (1993). A novel interferon-inducible domain: structural and functional analysis of the human interferon regulatory factor 1 gene promoter. *Mol. Cell. Biol.* 13: 690-702.
24. Chin, Y. et al. (1996). Cell growth arrest and induction of cyclin dependent kinase inhibitor p $21^{waf1/cip1}$ mediated by STAT1. *Science.* 272: 719-722.
25. Kuniyasu, H. et al. (1997). Growth inhibitory effect of interferon-beta is associated with the induction of cyclin-dependent kinase inhibitor p27 Kip1 in a human gastric carcinoma cell line. *Cell Growth Differ* 8: 47-52.
26. Chin Y E, Kitagawa M, Kuida K, Flavell Ru A, Fu X Y. (1997). Activation of the Stat signaling pathway can cause expression of caspase 1 and apoptosis. *Mol. Cell. Biol.* 17: 5328-37.
27. Kolla, V et al. (1996). Modulation of interferon (IFN)-inducible gene expression by retinoic acid. Up-regulation of STAT1 protein in IFN-unresponsive cells. *J. Biol. Chem.* 271: 10508-14.
28. Perou, C., Jeffrey, S., Van de Rijn, M. et al. (1999). Distinctive gene expression patterns in human mammary epithelial cells and breast cancers. *Proc. Natl. Acad. Sci.* 96: 9212-9217.
29. Sun, W. H. et al. Interferon-alpha resistance in a cutaneous T-cell lymphoma cell line is associated with lack of Stat1 expression. *Blood* 91: 570-576.
30. Abril, E. et al. Unresponsiveness to interferon associated with Stat1 protein deficiency in a gastric adenocarcinoma cell line. *Cancer Immunol Immunother* 47: 1130-120.
31. Levy, D E, D S Kessler, R Pine and J E Darnell Jr (1989) *Genes Dev.* 3: 1362-1371.
32. McAdam A J, Schweitzer A N, Sharpe A H. The role of B7 co-stimulation in activation and differentiation of CD4+ and CD8+ T cells. *Immunol Rev* 1998 October; 165: 231-47.
33. L Chen et al. (1994). Tumour immunogenicity determines the effect of B7 co-stimulation on T cell mediated tumour immunity. *J. Exp. Med.* 179: 523-532.
34. Chen L, Linsley P S, Hellstrom K E. (1993). Co-stimulation of T cells for tumour immunity. *Immunology Today.* 14: 483-485.
35. Ramarathinam L, Castle M, Wu Y, Liu Y. (1994). T cell co-stimulation by B7/BB1 induces CD8 T cell dependent tumour rejection; An important role of B7/BB ini the induction, recruitment, and effector function of antitumour T cells. *J. Exp. Med.* 179: 1205-1214.
36. Cavallo F, Martin-Fontecha A, Bellone M, Heltai S, Gatti E, Tornaghi P, Freschi M, Formi G, Dellabona P, Casorati G. (1995). Co-expression of B7-1 and ICAM-1 on tumours is required for rejection and the establishment of a memory response. *Eur. J. Immunol.* 25: 154-1162.
37. Martin-Fontecha A, Cavallo F, Bellone M, Heltai S, Iezzi G, Tornaghi P, Nabavi N, Formi G, Dellabona P, Casorati G. (1996). *Eur J Immunol* August 26(8): 1851-9 Heterogeneous effects on B7-1 and B7-2 in the induction of both protective and therapeutic anti-tumour immunity against different mouse tumours.
38. Chen L. et al. (1994). Tumour immunogenicity determines the effect of B7 co-stimulation on a T cell-mediated tumor immunity. *J. Exp. Med.* 179: 523-532.
39. Coligan, J. E. Chapt 3.11 in *Current Protocols in Immunology*. (1994). Publ. by John Wiley & Sons.
40. Hersey P, Si Z, Smith M J, Thomas W D. (1994). Expression of the co-stimulatory molecule B7 on melanoma cells. *Int J Cancer* 58: 527-32.
41. Wunderlich, J. and G. Shearer. (1993). Chpt 3.11. In Vitro Assays for Mouse Lymphocyte Function. In *Current Protocols in Immunology*. 1993. J. E. Coligan, A. M. Kruisbeek, D. H. Margulies, E. M. Shevach and W. Strober eds., Greene Pub. Associates And Wiley-Interscience, New York, p3.11.14.
42. Nociari, M. M., Shalev, A., Benias, P., Russo, C. (1998) A novel one-step, highly sensitive fluorometric assay to evaluate cell-mediated cytotoxicity. *J. Immunol. Methods* 213: 157-167.
43. Mashko, S. V., V. P. Veiko, A. L. Lapidus, M. I. Lebedeva, A. V. Mochulsky, I. I. Shechter, M. E. Trukhan, K. I. Ratmanova, B. A. Rebentish, V. E. Kaluzhsky. (1990) TGATG vector: a new expression system for cloned foreign genes in *Escherichia coli* cells. *Gene* 88: 121.
44. Hertzog, P. J., P. Emery, B. F. Cheetham, I. R. Mackay and A. W. Linnane. (1988). Interferons in rheumatoid arthritis: alterations in production and response related to disease activity. *Clin. Immunol. Immunpathol.*, 48: 192.

What is claimed is:

1. A method for enhancing immunopotentiation of animal cells, comprising:
culturing animal cells in the presence of a T-cell co-stimulatory B7molecule selected from the group consisting of B7-1 and B7-2 on the surface of said cells in the presence of a type II interferon (IFN) in exogenous form and at least one type I IFN in exogenous form for a time and under conditions sufficient to enhance the antigen presenting functions of said cells.

2. The method of claim 1, wherein the animal cells are cultured by contacting said cells with a type II IFN in exogenous form for a time and under conditions sufficient to permit cellular responsiveness to at least one type I IFN and contacting the cells with the at least one type I IFN in exogenous form for a time and under conditions sufficient to enhance the antigen presenting function of said cells.

3. The method of claim 1, wherein the type II IFN is present in the culture medium at a concentration of about 100 to about 2000 international units/mL.

4. The method of claim 1, wherein an individual type I IFN is present in the culture medium at a concentration of about 100 to about 2000 international units/mL.

5. The method of claim 1, wherein the cells are cultured in the presence of a type II IFN from about 16 to about 96 hours and subsequently in the presence of at least one type I IFN from about 16 to about 72 hours.

6. The method of claim 1, wherein said animal cells express said T-cell co-stimulatory B7 molecule.

7. The method of claim 6, further comprising modifying the animal cells to express said T-cell co-stimulatory B7 molecule prior to culturing.

8. The method of claim 7, wherein said modification comprises introducing into said animal cells a polynucleotide from which the T-cell co-stimulatory B7molecule is expressed.

9. The method of claim 1, wherein the type II IFN is an IFN-gamma.

10. The method of claim 1, wherein an individual type I IFN is selected from the group consisting of an IFN-alpha and an IFN-beta 11. The method of claim 1, further comprising inactivating said cells.

12. The method of claim 11, wherein said inactivation comprises treating said cells to render them incapable of proliferation.

13. The method of claim 9, wherein the IFN-gamma comprises the amino acid sequence set forth in SEQ ID NO: 2.

14. The method of claim 10, wherein the IFN-beta is an IFN-beta 1.

15. The method of claim 10, wherein the IFN-beta is an IFN-beta 1comprising the amino acid sequence set forth in SEQ ID NO: 4.

16. The method of claim 10, wherein the IFN-beta is an IFN-beta 2.

17. The method of claim 10, wherein the IFN-beta is an IFN-beta 2comprising the amino acid sequence set forth in SEQ ID NO: 6.

18. The method of claim 10, wherein the IFN-alpha comprises the amino acid sequence set forth in SEQ ID NO: 8.

19. The method of claim 10, wherein the IFN-alpha is an IFN-alpha 1.

20. The method of claim 10, wherein the IFN-alpha 1 comprises the amino acid sequence set forth in SEQ ID NO: 10.

21. The method of claim 10, wherein the IFN-alpha is an IFN-alpha 2.

22. The method of claim 10, wherein the IFN-alpha is an IFN-alpha 2comprising the amino acid sequence set forth in SEQ ID NO: 12.

23. The method of claim 1, wherein the animal cells are cultured by contacting the cells with a single type I IFN in exogenous form.

24. The method of claim 23, wherein said type I IFN is selected from the group consisting of an IFN-alpha and an IFN-beta.

25. The method of claim 24, wherein said type I IFN is an IFN-beta.

26. The method of claim 1, wherein the animal cells are cultured by contacting the cells with a first type I IFN in exogenous form and a second type I IFN in exogenous form.

27. The method of claim 26, wherein the first type I IFN and the second type I IFN are each independently selected from the group consisting of an IFN-beta and an IFN-alpha.

28. The method of claim 26, wherein the type II IFN is an IFN-gamma and wherein the first type I IFN and the second type I IFN are individually selected from IFN-alpha and IFN-beta.

29. The method of claim 26, wherein the type II IFN is an IFN-gamma and wherein the first type I IFN is an IFN-beta and the second type I IFN is an IFN-alpha.

30. The method of claim 1, wherein the cells are cultured in the presence of IFN-gamma from about 48 to about 96 hours and subsequently in the presence of IFN-alpha and/or IFN-beta from about 24 to about 72 hours.

31. The method of claim 1, wherein the cells are cultured in the presence of IFN-gamma from about 48 to about 96 hours and subsequently in the presence of IFN-beta from about 24 to about 72 hours.

32. The method for enhancing immunopotentiation of animal cells of claim 1, further comprising:
combining the animal cells with the a T-cell co-stimulatory B7 molecule in soluble form prior to culturing.

33. The method of claim 32, wherein the animal cells are cultured by contacting said cells with a type II IFN in exogenous form for a time and under conditions sufficient to permit cellular responsiveness to at least one type I IFN and contacting the cells with the at least one type I IFN in exogenous form for a time and under conditions sufficient to enhance the antigen presenting function of said cells.

34. The method of claim 32, wherein the type II IFN is present in the culture medium at a concentration of about 100 to about 2000 international units/mL.

35. The method of claim 32, wherein an individual type I IFN is present in the culture medium at a concentration of about 100 to about 2000 international units/mL.

36. The method of claim 32, wherein the cells are cultured in the presence of a type II IFN from about 16 to about 96 hours and subsequently in the presence of at least one type I IFN from about 16 to about 72 hours.

37. The method of claim 32, wherein the type II IFN is an IFN-gamma.

38. The method of claim 32, wherein an individual type I IFN is selected from the group consisting of an IFN-alpha and an IFN-beta.

39. The method of claim 32, further comprising inactivating said cells.

40. The method of claim 39, wherein said inactivation comprises treating said cells to render them incapable of proliferation.

41. The method of claim 37, wherein the IFN-gamma comprises the amino acid sequence set forth in SEQ ID NO: 2.

42. The method of claim 38, wherein the IFN-beta is an IFN-beta 1.

43. The method of claim 38, wherein the IFN-beta is an IFN-beta 1comprising the amino acid sequence set forth in SEQ ID NO: 4.

44. The method of claim 38, wherein the IFN-beta is an IFN-beta 2.

45. The method of claim 38, wherein the IFN-beta is an IFN-beta 2comprising the amino acid sequence set forth in SEQ ID NO: 6.

46. The method of claim 38, wherein the IFN-alpha comprises the amino acid sequence set forth in SEQ ID NO: 8.

47. The method of claim 38, wherein the IFN-alpha is an IFN-alpha 1.

48. The method of claim 38, wherein the IFN-alpha is an IFN-alpha 1comprising the amino acid sequence set forth in SEQ ID NO: 10.

49. The method of claim 38, wherein the IFN-alpha is an IFN-alpha 2.

50. The method of claim 38, wherein the IFN-alpha is an IFN-alpha 2comprising the amino acid sequence set forth in SEQ ID NO: 12.

51. The method of claim 32, wherein the animal cells are cultured by contacting the cells with a single type I IFN in exogenous form.

52. The method of claim 51, wherein said type I IFN is selected from the group consisting of an IFN-alpha and an IFN-beta.

53. The method of claim 52, wherein said type I IFN is an IFN-beta.

54. The method of claim 32, wherein the animal cells are cultured by contacting the cells with a first type I IFN in exogenous form and a second type I IFN in exogenous form.

55. The method of claim 54, wherein the first type I IFN and the second type I IFN are each independently selected from the group consisting of an IFN-beta and an IFN-alpha.

56. The method of claim 54, wherein the type II IFN is an IFN-gamma and wherein the first type I IFN and the second type I IFN are individually selected from IFN-alpha and IFN-beta.

57. The method of claim 54, wherein the type II IFN is an IFN-gamma and wherein the first type I IFN is an IFN-beta and the second type I IFN is an IFN-alpha.

58. The method of claim 32, wherein the cells are cultured in the presence of IFN-gamma from about 48 to about 96 hours and subsequently in the presence of IFN-alpha and/or IFN-beta from about 24 to about 72 hours.

\* \* \* \* \*

UNITED STATES PATENT AND TRADEMARK OFFICE
CERTIFICATE OF CORRECTION

PATENT NO. : 7,964,400 B2
APPLICATION NO. : 12/259194
DATED : June 21, 2011
INVENTOR(S) : Stephen John Ralph Page 1 of 2

It is certified that error appears in the above-identified patent and that said Letters Patent is hereby corrected as shown below:

- Title Page 1 (Item 56) Column 2, Line 40, under Other Publications, change "induction." to --induction--.
- Title Page 2 (Item 56) Column 1, Line 51, under Other Publications, change "allergeneic" to --allogeneic--.
- Title Page 2 (Item 56) Column 1, Line 67, under Other Publications, change "sectertion"," to --secretion",--.
- Title Page 3 (Item 56) Column 1, Line 7, under Other Publications, change "ISGFEγ'" to --ISGF3γ"--.
- Column 1, Line 43, Change "Stat 1." to --Stat1.--.
- Column 8, Line 17 (Approx.), Change "B7-1 High" to --B7-1High--.
- Column 8, Line 34, Change "F10/B7$^{hi}$" to --F10/B7-1$^{hi}$--.
- Column 8, Line 41, Change "B166-F10/B7$^{hi}$" to --B166-F10/B7-1$^{hi}$--.
- Column 8, Line 52-53 (Approx.), Change "B7-1 μl" to --B7-1$^{hi}$--.
- Column 11, Line 55-56, Change "artherosclerosis," to --atherosclerosis,--.
- Column 17, Line 17 (Approx.), Change "Ficol™" to --Ficoll™--.
- Column 18, Line 23, Change "Immunol" to --Immunol.--.
- Column 20, Line 45, Change "fermentors" to --fermenters--.
- Column 24, Line 55-56, Change "brionchoalveolar" to --bronchoalveolar--.
- Column 25, Line 1, Change "oesophageal" to --csophageal--.
- Column 25, Line 38, After "polynucleotides" insert --.--.
- Column 27, Line 53, Change "P-galactosidase," to --β-galactosidase,--.
- Column 28, Line 44, Change "the a" to --a--.
- Column 29, Line 57, Change "DH50α" to --DH5α--.

Signed and Sealed this
Sixth Day of March, 2012

David J. Kappos
*Director of the United States Patent and Trademark Office*

CERTIFICATE OF CORRECTION (continued)
U.S. Pat. No. 7,964,400 B2

- Column 29, Line 64, Change "Infections" to --Infectious--.
- Column 30, Line 11 (Approx.), Change "50 µg/mL" to --50 U/mL--.
- Column 30, Line 20-21, Change "Can berra" to --Canberra--.
- Column 30, Line 23, Change "(Can berra" to --(Canberra--.
- Column 30, Line 23, Change "Packard)." to --Packard)--.
- Column 30, Line 56 (Approx.), Change "(AF Targets" to --{(AF Targets--.
- Column 32, Line 67, Change "B136-F10" to --B16-F10--.
- Column 35, Line 50, Change "B7-1 Hi" to --B7-1Hi--.
- Column 37, Line 62, Change "class 1" to --class I--.
- Column 39, Line 42, Change "B 16-F10" to --B16-F10--.
- Column 41, Line 20, After "application" insert --.--.
- Column 43, Line 11 (Approx.), Change "Einorn" to --Einhorn--.
- Column 43, Line 23, Change "Einhom" to --Einhorn--.
- Column 43, Line 55, Change "Ru A," to --RA,--.
- Column 44, Line 23 (Approx.), Change "ini" to --in--.
- Column 44, Line 27, Change "Formi" to --Forni--.
- Column 44, Line 33, Change "Formi" to --Forni--.
- Column 44, Line 67 (Approx.), Change "Immunpathol.," to --Immunopathol.,--.
- Column 75, Line 5, In Claim 1, change "B7molecule" to --B7 molecule--.
- Column 75, Line 35, In Claim 8, change "B7molecule" to --B7 molecule--.
- Column 75, Line 41, In Claim 10, after "IFN-beta" insert --.--.
- Column 75, Line 52, In Claim 15, change "1comprising" to --1 comprising--.
- Column 75, Line 57, In Claim 17, change "2comprising" to --2 comprising--.
- Column 76, Line 2, In Claim 22, change "2comprising" to --2 comprising--.
- Column 76, Line 36, In Claim 32, change "the a" to --a--.
- Column 77, Line 4, In Claim 43, change "1comprising" to --1 comprising--.
- Column 77, Line 9, In Claim 45, change "2comprising" to --2 comprising--.
- Column 77, Line 16 (Approx.), In Claim 48, change "1comprising" to --1 comprising--.
- Column 77, Line 21 (Approx.), In Claim 50, change "2comprising" to --2 comprising--.

SEQUENCE LISTING

<160> NUMBER OF SEQ ID NOS: 20

<210> SEQ ID NO 1
<211> LENGTH: 501
<212> TYPE: DNA
<213> ORGANISM: Homo sapiens
<220> FEATURE:
<221> NAME/KEY: CDS
<222> LOCATION: (1)...(501)

<400> SEQUENCE: 1

```
atg aaa tat aca agt tat atc ttg gct ttt cag ctc tgc atc gtt ttg        48
Met Lys Tyr Thr Ser Tyr Ile Leu Ala Phe Gln Leu Cys Ile Val Leu
 1               5                  10                  15 ggt tct ctt ggc tgt tac tgc cag gac cca tat gta aaa gaa gca gaa        96
Gly Ser Leu Gly Cys Tyr Cys Gln Asp Pro Tyr Val Lys Glu Ala Glu
            20                  25                  30 aac ctt aag aaa tat ttt aat gca ggt cat tca gat gta gcg gat aat       144
Asn Leu Lys Lys Tyr Phe Asn Ala Gly His Ser Asp Val Ala Asp Asn
        35                  40                  45 gga act ctt ttc tta ggc att ttg aag aat tgg aaa gag gag agt gac       192
Gly Thr Leu Phe Leu Gly Ile Leu Lys Asn Trp Lys Glu Glu Ser Asp
    50                  55                  60 aga aaa ata atg cag agc caa att gtc tcc ttt tac ttc aaa ctt ttt       240
Arg Lys Ile Met Gln Ser Gln Ile Val Ser Phe Tyr Phe Lys Leu Phe
65                  70                  75                  80 aaa aac ttt aaa gat gac cag agc atc caa aag agt gtg gag acc atc       288
Lys Asn Phe Lys Asp Asp Gln Ser Ile Gln Lys Ser Val Glu Thr Ile
                85                  90                  95 aag gaa gac atg aat gtc aag ttt ttc aat agc aac aaa aag aaa cga       336
Lys Glu Asp Met Asn Val Lys Phe Phe Asn Ser Asn Lys Lys Lys Arg
            100                 105                 110 gat gac ttc gaa aag ctg act aat tat tcg gta act gac ttg aat gtc       384
Asp Asp Phe Glu Lys Leu Thr Asn Tyr Ser Val Thr Asp Leu Asn Val
        115                 120                 125 caa cgc aaa gca ata cat gaa ctc atc caa gtg atg gct gaa ctg tcg       432
Gln Arg Lys Ala Ile His Glu Leu Ile Gln Val Met Ala Glu Leu Ser
    130                 135                 140 cca gca gct aaa aca ggg aag cga aaa agg agt cag atg ctg ttt cga       480
Pro Ala Ala Lys Thr Gly Lys Arg Lys Arg Ser Gln Met Leu Phe Arg
145                 150                 155                 160 ggt cga aga gca tcc cag taa                                           501
Gly Arg Arg Ala Ser Gln *
                165
```

<210> SEQ ID NO 2
<211> LENGTH: 166
<212> TYPE: PRT
<213> ORGANISM: Homo sapiens

<400> SEQUENCE: 2

```
Met Lys Tyr Thr Ser Tyr Ile Leu Ala Phe Gln Leu Cys Ile Val Leu
 1               5                  10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
```

```
                65                  70                  75                  80
Lys Asn Phe Lys Asp Asp Gln Ser Ile Gln Lys Ser Val Glu Thr Ile
                    85                  90                  95
Lys Glu Asp Met Asn Val Lys Phe Phe Asn Ser Asn Lys Lys Lys Arg
                100                 105                 110
Asp Asp Phe Glu Lys Leu Thr Asn Tyr Ser Val Thr Asp Leu Asn Val
            115                 120                 125
Gln Arg Lys Ala Ile His Glu Leu Ile Gln Val Met Ala Glu Leu Ser
        130                 135                 140
Pro Ala Ala Lys Thr Gly Lys Arg Lys Ser Gln Met Leu Phe Arg
145                 150                 155                 160
Gly Arg Arg Ala Ser Gln
                165

<210> SEQ ID NO 3
<211> LENGTH: 564
<212> TYPE: DNA
<213> ORGANISM: Homo sapiens
<220> FEATURE:
<221> NAME/KEY: CDS
<222> LOCATION: (1)...(564)

<400> SEQUENCE: 3 atg acc aac aag tgt ctc ctc caa att gct ctc ctg ttg tgc ttc tcc      48
Met Thr Asn Lys Cys Leu Leu Gln Ile Ala Leu Leu Leu Cys Phe Ser
 1               5                  10                  15 act aca gct ctt tcc atg agc tac aac ttg ctt gga ttc cta caa aga      96
Thr Thr Ala Leu Ser Met Ser Tyr Asn Leu Leu Gly Phe Leu Gln Arg
            20                  25                  30 agc agc aat ttt cag tgt cag aag ctc ctg tgg caa ttg aat ggg agg     144
Ser Ser Asn Phe Gln Cys Gln Lys Leu Leu Trp Gln Leu Asn Gly Arg
        35                  40                  45 ctt gaa tac tgc ctc aag gac agg atg aac ttt gac atc cct gag gag     192
Leu Glu Tyr Cys Leu Lys Asp Arg Met Asn Phe Asp Ile Pro Glu Glu
 50                  55                  60 att aag cag ctg cag cag ttc cag aag gag gac gcc gca ttg acc atc     240
Ile Lys Gln Leu Gln Gln Phe Gln Lys Glu Asp Ala Ala Leu Thr Ile
 65                  70                  75                  80 tat gag atg ctc cag aac atc ttt gct att ttc aga caa gat tca tct     288
Tyr Glu Met Leu Gln Asn Ile Phe Ala Ile Phe Arg Gln Asp Ser Ser
                85                  90                  95 agc act ggc tgg aat gag act att gtt gag aac ctc ctg gct aat gtc     336
Ser Thr Gly Trp Asn Glu Thr Ile Val Glu Asn Leu Leu Ala Asn Val
            100                 105                 110 tat cat cag ata aac cat ctg aag aca gtc ctg gaa gaa aaa ctg gag     384
Tyr His Gln Ile Asn His Leu Lys Thr Val Leu Glu Glu Lys Leu Glu
        115                 120                 125 aaa gaa gat ttc acc agg gga aaa ctc atg agc agt ctg cac ctg aaa     432
Lys Glu Asp Phe Thr Arg Gly Lys Leu Met Ser Ser Leu His Leu Lys
    130                 135                 140 aga tat tat ggg agg att ctg cat tac ctg aag gcc aag gag tac agt     480
Arg Tyr Tyr Gly Arg Ile Leu His Tyr Leu Lys Ala Lys Glu Tyr Ser
145                 150                 155                 160 cac tgt gcc tgg acc ata gtc aga gtg gaa atc cta agg aac ttt tac     528
His Cys Ala Trp Thr Ile Val Arg Val Glu Ile Leu Arg Asn Phe Tyr
                165                 170                 175 ttc att aac aga ctt aca ggt tac ctc cga aac tga                     564
Phe Ile Asn Arg Leu Thr Gly Tyr Leu Arg Asn *
                180                 185
```

-continued

<210> SEQ ID NO 4
<211> LENGTH: 187
<212> TYPE: PRT
<213> ORGANISM: Homo sapiens

<400> SEQUENCE: 4

Met Thr Asn Lys Cys Leu Leu Gln Ile Ala Leu Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
    130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
            180                 185

<210> SEQ ID NO 5
<211> LENGTH: 639
<212> TYPE: DNA
<213> ORGANISM: Homo sapiens
<220> FEATURE:
<221> NAME/KEY: CDS
<222> LOCATION: (1)...(639)

<400> SEQUENCE: 5 atg aac tcc ttc tcc aca agc gcc ttc ggt cca gtt gcc ttc tcc ctg      48
Met Asn Ser Phe Ser Thr Ser Ala Phe Gly Pro Val Ala Phe Ser Leu
1               5                   10                  15 ggg ctg ctc ctg gtg ttg cct gct gcc ttc cct gcc cca gta ccc cca      96
Gly Leu Leu Leu Val Leu Pro Ala Ala Phe Pro Ala Pro Val Pro Pro
            20                  25                  30 gga gaa gat tcc aaa gat gta gcc gcc cca cac aga cag cca ctc acc     144
Gly Glu Asp Ser Lys Asp Val Ala Ala Pro His Arg Gln Pro Leu Thr
        35                  40                  45 tct tca gaa cga att gac aaa caa att cgg tac atc ctc gac ggc atc     192
Ser Ser Glu Arg Ile Asp Lys Gln Ile Arg Tyr Ile Leu Asp Gly Ile
    50                  55                  60 tca gcc ctg aga aag gag aca tgt aac aag agt aac atg tgt gaa agc     240
Ser Ala Leu Arg Lys Glu Thr Cys Asn Lys Ser Asn Met Cys Glu Ser
65                  70                  75                  80 agc aaa gag gca ctg gca gaa aac aac ctg aac ctt cca aag atg gct     288
Ser Lys Glu Ala Leu Ala Glu Asn Asn Leu Asn Leu Pro Lys Met Ala
                85                  90                  95 gaa aaa gat gga tgc ttc caa tct gga ttc aat gag gag act tgc ctg     336
Glu Lys Asp Gly Cys Phe Gln Ser Gly Phe Asn Glu Glu Thr Cys Leu

```
              100                 105                  110
gtg aaa atc atc act ggt ctt ttg gag ttt gag gta tac cta gag tac    384
Val Lys Ile Ile Thr Gly Leu Leu Glu Phe Glu Val Tyr Leu Glu Tyr
        115                 120                 125 ctc cag aac aga ttt gag agt agt gag gaa caa gcc aga gct gtc cag    432
Leu Gln Asn Arg Phe Glu Ser Ser Glu Glu Gln Ala Arg Ala Val Gln
130                 135                 140 atg agt aca aaa gtc ctg atc cag ttc ctg cag aaa aag gca aag aat    480
Met Ser Thr Lys Val Leu Ile Gln Phe Leu Gln Lys Lys Ala Lys Asn
145                 150                 155                 160 cta gat gca ata acc acc cct gac cca acc aca aat gcc agc ctg ctg    528
Leu Asp Ala Ile Thr Thr Pro Asp Pro Thr Thr Asn Ala Ser Leu Leu
                165                 170                 175 acg aag ctg cag gca cag aac cag tgg ctg cag gac atg aca act cat    576
Thr Lys Leu Gln Ala Gln Asn Gln Trp Leu Gln Asp Met Thr Thr His
            180                 185                 190 ctc att ctg cgc agc ttt aag gag ttc ctg cag tcc agc ctg agg gct    624
Leu Ile Leu Arg Ser Phe Lys Glu Phe Leu Gln Ser Ser Leu Arg Ala
        195                 200                 205 ctt cgg caa atg tag                                                639
Leu Arg Gln Met  *
    210

<210> SEQ ID NO 6
<211> LENGTH: 212
<212> TYPE: PRT
<213> ORGANISM: Homo sapiens

<400> SEQUENCE: 6

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210
```

```
<210> SEQ ID NO 7
<211> LENGTH: 567
<212> TYPE: DNA
<213> ORGANISM: Homo sapiens
<220> FEATURE:
<221> NAME/KEY: CDS
<222> LOCATION: (1)...(567)

<400> SEQUENCE: 7 atg gcc ttg acc ttt gct tta ctg gtg gcc ctc ctg gtg ctc agc tgc      48
Met Ala Leu Thr Phe Ala Leu Leu Val Ala Leu Leu Val Leu Ser Cys
 1               5                  10                  15 aag tca agc tgc tct gtg ggc tgt gat ctg cct caa acc cac agc ctg      96
Lys Ser Ser Cys Ser Val Gly Cys Asp Leu Pro Gln Thr His Ser Leu
            20                  25                  30 ggt agc agg agg acc ttg atg ctc ctg gca cag atg agg aaa atc tct     144
Gly Ser Arg Arg Thr Leu Met Leu Leu Ala Gln Met Arg Lys Ile Ser
        35                  40                  45 ctt ttc tcc tgc ttg aag gac aga cat gac ttt gga ttt ccc cag gag     192
Leu Phe Ser Cys Leu Lys Asp Arg His Asp Phe Gly Phe Pro Gln Glu
    50                  55                  60 gag ttt ggc aac cag ttc caa aag gct gaa acc atc cct gtc ctc cat     240
Glu Phe Gly Asn Gln Phe Gln Lys Ala Glu Thr Ile Pro Val Leu His
65                  70                  75                  80 gag atg atc cag cag atc ttc aat ctc ttc agc aca aag gac tca tct     288
Glu Met Ile Gln Gln Ile Phe Asn Leu Phe Ser Thr Lys Asp Ser Ser
                85                  90                  95 gct gct tgg gat gag acc ctc cta gac aaa ttc tac act gaa ctc tac     336
Ala Ala Trp Asp Glu Thr Leu Leu Asp Lys Phe Tyr Thr Glu Leu Tyr
            100                 105                 110 cag cag ctg aat gac ctg gaa gcc tgt gtg ata cag ggg gtg ggg gtg     384
Gln Gln Leu Asn Asp Leu Glu Ala Cys Val Ile Gln Gly Val Gly Val
        115                 120                 125 aca gag act ccc ctg atg aag gag gac tcc att ctg gct gtg agg aaa     432
Thr Glu Thr Pro Leu Met Lys Glu Asp Ser Ile Leu Ala Val Arg Lys
    130                 135                 140 tac ttc caa aga atc act ctc tat ctg aaa gag aag aaa tac agc cct     480
Tyr Phe Gln Arg Ile Thr Leu Tyr Leu Lys Glu Lys Lys Tyr Ser Pro
145                 150                 155                 160 tgt gcc tgg gag gtt gtc aga gca gaa atc atg aga tct ttt tct ttg     528
Cys Ala Trp Glu Val Val Arg Ala Glu Ile Met Arg Ser Phe Ser Leu
                165                 170                 175 tca aca aac ttg caa gaa agt tta aga agt aag gaa tga                 567
Ser Thr Asn Leu Gln Glu Ser Leu Arg Ser Lys Glu *
            180                 185

<210> SEQ ID NO 8
<211> LENGTH: 188
<212> TYPE: PRT
<213> ORGANISM: Homo sapiens

<400> SEQUENCE: 8

Met Ala Leu Thr Phe Ala Leu Leu Val Ala Leu Leu Val Leu Ser Cys
 1               5                  10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Lys Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys Ala Glu Thr Ile Pro Val Leu His
```

```
                65                  70                  75                  80
Glu Met Ile Gln Gln Ile Phe Asn Leu Phe Ser Thr Lys Asp Ser Ser
                        85                  90                  95

Ala Ala Trp Asp Glu Thr Leu Leu Asp Lys Phe Tyr Thr Glu Leu Tyr
                100                 105                 110

Gln Gln Leu Asn Asp Leu Glu Ala Cys Val Ile Gln Gly Val Gly Val
                115                 120                 125

Thr Glu Thr Pro Leu Met Lys Glu Asp Ser Ile Leu Ala Val Arg Lys
                130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu
                180                 185

<210> SEQ ID NO 9
<211> LENGTH: 570
<212> TYPE: DNA
<213> ORGANISM: Homo sapiens
<220> FEATURE:
<221> NAME/KEY: CDS
<222> LOCATION: (1)...(570)

<400> SEQUENCE: 9 atg gcc tcg ccc ttt gct tta ctg atg gtc ctg gtg gtg ctc agc tgc     48
Met Ala Ser Pro Phe Ala Leu Leu Met Val Leu Val Val Leu Ser Cys
 1               5                  10                  15 aag tca agc tgc tct ctg ggc tgt gat ctc cct gag acc cac agc ctg     96
Lys Ser Ser Cys Ser Leu Gly Cys Asp Leu Pro Glu Thr His Ser Leu
                20                  25                  30 gat aac agg agg acc ttg atg ctc ctg gca caa atg agc aga atc tct    144
Asp Asn Arg Arg Thr Leu Met Leu Leu Ala Gln Met Ser Arg Ile Ser
            35                  40                  45 cct tcc tcc tgt ctg atg gac aga cat gac ttt gga ttt ccc cag gag    192
Pro Ser Ser Cys Leu Met Asp Arg His Asp Phe Gly Phe Pro Gln Glu
        50                  55                  60 gag ttt gat ggc aac cag ttc cag aag gct cca gcc atc tct gtc ctc    240
Glu Phe Asp Gly Asn Gln Phe Gln Lys Ala Pro Ala Ile Ser Val Leu
65                  70                  75                  80 cat gag ctg atc cag cag atc ttc aac ctc ttt acc aca aaa gat tca    288
His Glu Leu Ile Gln Gln Ile Phe Asn Leu Phe Thr Thr Lys Asp Ser
                85                  90                  95 tct gct gct tgg gat gag gac ctc cta gac aaa ttc tgc acc gaa ctc    336
Ser Ala Ala Trp Asp Glu Asp Leu Leu Asp Lys Phe Cys Thr Glu Leu
                100                 105                 110 tac cag cag ctg aat gac ttg gaa gcc tgt gtg atg cag gag gag agg    384
Tyr Gln Gln Leu Asn Asp Leu Glu Ala Cys Val Met Gln Glu Glu Arg
            115                 120                 125 gtg gga gaa act ccc ctg atg aat gcg gac tcc atc ttg gct gtg aag    432
Val Gly Glu Thr Pro Leu Met Asn Ala Asp Ser Ile Leu Ala Val Lys
        130                 135                 140 aaa tac ttc cga aga atc act ctc tat ctg aca gag aag aaa tac agc    480
Lys Tyr Phe Arg Arg Ile Thr Leu Tyr Leu Thr Glu Lys Lys Tyr Ser
145                 150                 155                 160 cct tgt gcc tgg gag gtt gtc aga gca gaa atc atg aga tcc ctc tct    528
Pro Cys Ala Trp Glu Val Val Arg Ala Glu Ile Met Arg Ser Leu Ser
                165                 170                 175 tta tca aca aac ttg caa gaa aga tta agg agg aag gaa taa             570
Leu Ser Thr Asn Leu Gln Glu Arg Leu Arg Arg Lys Glu *
```

<210> SEQ ID NO 10
<211> LENGTH: 189
<212> TYPE: PRT
<213> ORGANISM: Homo sapiens

<400> SEQUENCE: 10

Met Ala Ser Pro Phe Ala Leu Leu Met Val Leu Val Val Leu Ser Cys
1               5                   10                  15

Lys Ser Ser Cys Ser Leu Gly Cys Asp Leu Pro Glu Thr His Ser Leu
            20                  25                  30

Asp Asn Arg Arg Thr Leu Met Leu Leu Ala Gln Met Ser Arg Ile Ser
        35                  40                  45

Pro Ser Ser Cys Leu Met Asp Arg His Asp Phe Gly Phe Pro Gln Glu
    50                  55                  60

Glu Phe Asp Gly Asn Gln Phe Gln Lys Ala Pro Ala Ile Ser Val Leu
65                  70                  75                  80

His Glu Leu Ile Gln Gln Ile Phe Asn Leu Phe Thr Thr Lys Asp Ser
                85                  90                  95

Ser Ala Ala Trp Asp Glu Asp Leu Leu Asp Lys Phe Cys Thr Glu Leu
            100                 105                 110

Tyr Gln Gln Leu Asn Asp Leu Glu Ala Cys Val Met Gln Glu Glu Arg
        115                 120                 125

Val Gly Glu Thr Pro Leu Met Asn Ala Asp Ser Ile Leu Ala Val Lys
130                 135                 140

Lys Tyr Phe Arg Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Leu Ser Thr Asn Leu Gln Glu Arg Leu Arg Arg Lys Glu
            180                 185

<210> SEQ ID NO 11
<211> LENGTH: 567
<212> TYPE: DNA
<213> ORGANISM: Homo sapiens
<220> FEATURE:
<221> NAME/KEY: CDS
<222> LOCATION: (1)...(567)

<400> SEQUENCE: 11 atg gcc ttg acc ttt gct tta ctg gtg gcc ctc ctg gtg ctc agc tgc      48
Met Ala Leu Thr Phe Ala Leu Leu Val Ala Leu Leu Val Leu Ser Cys
1               5                   10                  15 aag tca agc tgc tct gtg ggc tgt gat ctg cct caa acc cac agc ctg      96
Lys Ser Ser Cys Ser Val Gly Cys Asp Leu Pro Gln Thr His Ser Leu
            20                  25                  30 ggt agc agg agg acc ttg atg ctc ctg gca cag atg agg aga atc tct     144
Gly Ser Arg Arg Thr Leu Met Leu Leu Ala Gln Met Arg Arg Ile Ser
        35                  40                  45 ctt ttc tcc tgc ttg aag gac aga cat gac ttt gga ttt ccc cag gag     192
Leu Phe Ser Cys Leu Lys Asp Arg His Asp Phe Gly Phe Pro Gln Glu
    50                  55                  60 gag ttt ggc aac cag ttc caa aag gct gaa acc atc cct gtc ctc cat     240
Glu Phe Gly Asn Gln Phe Gln Lys Ala Glu Thr Ile Pro Val Leu His
65                  70                  75                  80 gag atg atc cag cag atc ttc aat ctc ttc agc aca aag gac tca tct     288
Glu Met Ile Gln Gln Ile Phe Asn Leu Phe Ser Thr Lys Asp Ser Ser
                85                  90                  95

```
gct gct tgg gat gag acc ctc cta gac aaa ttc tac act gaa ctc tac      336
Ala Ala Trp Asp Glu Thr Leu Leu Asp Lys Phe Tyr Thr Glu Leu Tyr
        100                 105                 110 cag cag ctg aat gac ctg gaa gcc tgt gtg ata cag ggg gtg ggg gtg      384
Gln Gln Leu Asn Asp Leu Glu Ala Cys Val Ile Gln Gly Val Gly Val
    115                 120                 125 aca gag act ccc ctg atg aag gag gac tcc att ctg gct gtg agg aaa      432
Thr Glu Thr Pro Leu Met Lys Glu Asp Ser Ile Leu Ala Val Arg Lys
130                 135                 140 tac ttc caa aga atc act ctc tat ctg aaa gag aag aaa tac agc cct      480
Tyr Phe Gln Arg Ile Thr Leu Tyr Leu Lys Glu Lys Lys Tyr Ser Pro
145                 150                 155                 160 tgt gcc tgg gag gtt gtc aga gca gaa atc atg aga tct ttt tct ttg      528
Cys Ala Trp Glu Val Val Arg Ala Glu Ile Met Arg Ser Phe Ser Leu
            165                 170                 175 tca aca aac ttg caa gaa agt tta aga agt aag gaa tga                  567
Ser Thr Asn Leu Gln Glu Ser Leu Arg Ser Lys Glu *
        180                 185

<210> SEQ ID NO 12
<211> LENGTH: 188
<212> TYPE: PRT
<213> ORGANISM: Homo sapiens

<400> SEQUENCE: 12

Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Arg Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Lys Asp Ser Ser
                85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
    130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu
            180                 185

<210> SEQ ID NO 13
<211> LENGTH: 867
<212> TYPE: DNA
<213> ORGANISM: Homo sapiens
<220> FEATURE:
<221> NAME/KEY: CDS
<222> LOCATION: (1)...(867)

<400> SEQUENCE: 13
```

```
atg ggc cac aca cgg agg cag gga aca tca cca tcc aag tgt cca tac     48
Met Gly His Thr Arg Arg Gln Gly Thr Ser Pro Ser Lys Cys Pro Tyr
1               5                   10                  15 ctc aat ttc ttt cag ctc ttg gtg ctg gct ggt ctt tct cac ttc tgt     96
Leu Asn Phe Phe Gln Leu Leu Val Leu Ala Gly Leu Ser His Phe Cys
            20                  25                  30 tca ggt gtt atc cac gtg acc aag gaa gtg aaa gaa gtg gca acg ctg    144
Ser Gly Val Ile His Val Thr Lys Glu Val Lys Glu Val Ala Thr Leu
        35                  40                  45 tcc tgt ggt cac aat gtt tct gtt gaa gag ctg gca caa act cgc atc    192
Ser Cys Gly His Asn Val Ser Val Glu Glu Leu Ala Gln Thr Arg Ile
50                  55                  60 tac tgg caa aag gag aag aaa atg gtg ctg act atg atg tct ggg gac    240
Tyr Trp Gln Lys Glu Lys Lys Met Val Leu Thr Met Met Ser Gly Asp
65                  70                  75                  80 atg aat ata tgg ccc gag tac aag aac cgg acc atc ttt gat atc act    288
Met Asn Ile Trp Pro Glu Tyr Lys Asn Arg Thr Ile Phe Asp Ile Thr
                85                  90                  95 aat aac ctc tcc att gtg atc ctg gct ctg cgc cca tct gac gag ggc    336
Asn Asn Leu Ser Ile Val Ile Leu Ala Leu Arg Pro Ser Asp Glu Gly
            100                 105                 110 aca tac gag tgt gtt gtt ctg aag tat gaa aaa gac gct ttc aag cgg    384
Thr Tyr Glu Cys Val Val Leu Lys Tyr Glu Lys Asp Ala Phe Lys Arg
        115                 120                 125 gaa cac ctg gct gaa gtg acg tta tca gtc aaa gct gac ttc cct aca    432
Glu His Leu Ala Glu Val Thr Leu Ser Val Lys Ala Asp Phe Pro Thr
130                 135                 140 cct agt ata tct gac ttt gaa att cca act tct aat att aga agg ata    480
Pro Ser Ile Ser Asp Phe Glu Ile Pro Thr Ser Asn Ile Arg Arg Ile
145                 150                 155                 160 att tgc tca acc tct gga ggt ttt cca gag cct cac ctc tcc tgg ttg    528
Ile Cys Ser Thr Ser Gly Gly Phe Pro Glu Pro His Leu Ser Trp Leu
                165                 170                 175 gaa aat gga gaa gaa tta aat gcc atc aac aca aca gtt tcc caa gat    576
Glu Asn Gly Glu Glu Leu Asn Ala Ile Asn Thr Thr Val Ser Gln Asp
            180                 185                 190 cct gaa act gag ctc tat gct gtt agc agc aaa ctg gat ttc aat atg    624
Pro Glu Thr Glu Leu Tyr Ala Val Ser Ser Lys Leu Asp Phe Asn Met
        195                 200                 205 aca acc aac cac agc ttc atg tgt ctc atc aag tat gga cat tta aga    672
Thr Thr Asn His Ser Phe Met Cys Leu Ile Lys Tyr Gly His Leu Arg
210                 215                 220 gtg aat cag acc ttc aac tgg aat aca acc aag caa gag cat ttt cct    720
Val Asn Gln Thr Phe Asn Trp Asn Thr Thr Lys Gln Glu His Phe Pro
225                 230                 235                 240 gat aac ctg ctc cca tcc tgg gcc att acc tta atc tca gta aat gga    768
Asp Asn Leu Leu Pro Ser Trp Ala Ile Thr Leu Ile Ser Val Asn Gly
                245                 250                 255 att ttt gtg ata tgc tgc ctg acc tac tgc ttt gcc cca aga tgc aga    816
Ile Phe Val Ile Cys Cys Leu Thr Tyr Cys Phe Ala Pro Arg Cys Arg
            260                 265                 270 gag aga agg agg aat gag aga ttg aga agg gaa agt gta cgc cct gta    864
Glu Arg Arg Arg Asn Glu Arg Leu Arg Arg Glu Ser Val Arg Pro Val
        275                 280                 285 taa                                                                867
*
```

<210> SEQ ID NO 14
<211> LENGTH: 288
<212> TYPE: PRT
<213> ORGANISM: Homo sapiens

<400> SEQUENCE: 14

| | | | | | | | | | | | | | | | |
|---|---|---|---|---|---|---|---|---|---|---|---|---|---|---|---|
| Met | Gly | His | Thr | Arg | Arg | Gln | Gly | Thr | Ser | Pro | Ser | Lys | Cys | Pro | Tyr |
| 1 | | | | 5 | | | | | 10 | | | | | 15 | |

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
                35                  40                  45

Ser Cys Gly His Asn Val Ser Val Glu Glu Leu Ala Gln Thr Arg Ile
 50                  55                  60

Tyr Trp Gln Lys Glu Lys Lys Met Val Leu Thr Met Met Ser Gly Asp
 65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285

<210> SEQ ID NO 15
<211> LENGTH: 972
<212> TYPE: DNA
<213> ORGANISM: Homo sapiens
<220> FEATURE:
<221> NAME/KEY: CDS
<222> LOCATION: (1)...(972)

<400> SEQUENCE: 15

| atg | gga | ctg | agt | aac | att | ctc | ttt | gtg | atg | gcc | ttc | ctg | ctc | tct | ggt | 48 |
|---|---|---|---|---|---|---|---|---|---|---|---|---|---|---|---|---|
| Met | Gly | Leu | Ser | Asn | Ile | Leu | Phe | Val | Met | Ala | Phe | Leu | Leu | Ser | Gly | |
| 1 | | | | 5 | | | | | 10 | | | | | 15 | | |

| gct | gct | cct | ctg | aag | att | caa | gct | tat | ttc | aat | gag | act | gca | gac | ctg | 96 |
|---|---|---|---|---|---|---|---|---|---|---|---|---|---|---|---|---|
| Ala | Ala | Pro | Leu | Lys | Ile | Gln | Ala | Tyr | Phe | Asn | Glu | Thr | Ala | Asp | Leu | |
| | | | 20 | | | | | 25 | | | | | 30 | | | |

| cca | tgc | caa | ttt | gca | aac | tct | caa | aac | caa | agc | ctg | agt | gag | cta | gta | 144 |
|---|---|---|---|---|---|---|---|---|---|---|---|---|---|---|---|---|
| Pro | Cys | Gln | Phe | Ala | Asn | Ser | Gln | Asn | Gln | Ser | Leu | Ser | Glu | Leu | Val | |
| | | 35 | | | | | 40 | | | | | 45 | | | | |

| | | | | | | | | | | | | | | | | |
|---|---|---|---|---|---|---|---|---|---|---|---|---|---|---|---|---|
| gta | ttt | tgg | cag | gac | cag | gaa | aac | ttg | gtt | ctg | aat | gag | gta | tac | tta | 192 |
| Val | Phe | Trp | Gln | Asp | Gln | Glu | Asn | Leu | Val | Leu | Asn | Glu | Val | Tyr | Leu | |
| | 50 | | | | 55 | | | | | 60 | | | | | | |
| ggc | aaa | gag | aaa | ttt | gac | agt | gtt | cat | tcc | aag | tat | atg | ggc | cgc | aca | 240 |
| Gly | Lys | Glu | Lys | Phe | Asp | Ser | Val | His | Ser | Lys | Tyr | Met | Gly | Arg | Thr | |
| 65 | | | | | 70 | | | | | 75 | | | | | 80 | |
| agt | ttt | gat | tcg | gac | agt | tgg | acc | ctg | aga | ctt | cac | aat | ctt | cag | atc | 288 |
| Ser | Phe | Asp | Ser | Asp | Ser | Trp | Thr | Leu | Arg | Leu | His | Asn | Leu | Gln | Ile | |
| | | | | 85 | | | | | 90 | | | | | 95 | | |
| aag | gac | aag | ggc | ttg | tat | caa | tgt | atc | atc | cat | cac | aaa | aag | ccc | aca | 336 |
| Lys | Asp | Lys | Gly | Leu | Tyr | Gln | Cys | Ile | Ile | His | His | Lys | Lys | Pro | Thr | |
| | | | 100 | | | | | 105 | | | | | 110 | | | |
| gga | atg | att | cgc | atc | cac | cag | atg | aat | tct | gaa | ctg | tca | gtg | ctt | gct | 384 |
| Gly | Met | Ile | Arg | Ile | His | Gln | Met | Asn | Ser | Glu | Leu | Ser | Val | Leu | Ala | |
| | | 115 | | | | | 120 | | | | | 125 | | | | |
| aac | ttc | agt | caa | cct | gaa | ata | gta | cca | att | tct | aat | ata | aca | gaa | aat | 432 |
| Asn | Phe | Ser | Gln | Pro | Glu | Ile | Val | Pro | Ile | Ser | Asn | Ile | Thr | Glu | Asn | |
| 130 | | | | | 135 | | | | | 140 | | | | | | |
| gtg | tac | ata | aat | ttg | acc | tgc | tca | tct | ata | cac | ggt | tac | cca | gaa | cct | 480 |
| Val | Tyr | Ile | Asn | Leu | Thr | Cys | Ser | Ser | Ile | His | Gly | Tyr | Pro | Glu | Pro | |
| 145 | | | | | 150 | | | | | 155 | | | | | 160 | |
| aag | aag | atg | agt | gtt | ttg | cta | aga | acc | aag | aat | tca | act | atc | gag | tat | 528 |
| Lys | Lys | Met | Ser | Val | Leu | Leu | Arg | Thr | Lys | Asn | Ser | Thr | Ile | Glu | Tyr | |
| | | | | 165 | | | | | 170 | | | | | 175 | | |
| gat | ggt | att | atg | cag | aaa | tct | caa | gat | aat | gtc | aca | gaa | ctg | tac | gac | 576 |
| Asp | Gly | Ile | Met | Gln | Lys | Ser | Gln | Asp | Asn | Val | Thr | Glu | Leu | Tyr | Asp | |
| | | | 180 | | | | | 185 | | | | | 190 | | | |
| gtt | tcc | atc | agc | ttg | tct | gtt | tca | ttc | cct | gat | gtt | acg | agc | aat | atg | 624 |
| Val | Ser | Ile | Ser | Leu | Ser | Val | Ser | Phe | Pro | Asp | Val | Thr | Ser | Asn | Met | |
| | | 195 | | | | | 200 | | | | | 205 | | | | |
| acc | atc | ttc | tgt | att | ctg | gaa | act | gac | aag | acg | cgg | ctt | tta | tct | tca | 672 |
| Thr | Ile | Phe | Cys | Ile | Leu | Glu | Thr | Asp | Lys | Thr | Arg | Leu | Leu | Ser | Ser | |
| 210 | | | | | 215 | | | | | 220 | | | | | | |
| cct | ttc | tct | ata | gag | ctt | gag | gac | cct | cag | cct | ccc | cca | gac | cac | att | 720 |
| Pro | Phe | Ser | Ile | Glu | Leu | Glu | Asp | Pro | Gln | Pro | Pro | Pro | Asp | His | Ile | |
| 225 | | | | | 230 | | | | | 235 | | | | | 240 | |
| cct | tgg | att | aca | gct | gta | ctt | cca | aca | gtt | att | ata | tgt | gtg | atg | gtt | 768 |
| Pro | Trp | Ile | Thr | Ala | Val | Leu | Pro | Thr | Val | Ile | Ile | Cys | Val | Met | Val | |
| | | | | 245 | | | | | 250 | | | | | 255 | | |
| ttc | tgt | cta | att | cta | tgg | aaa | tgg | aag | aag | aag | aag | cgg | cct | cgc | aac | 816 |
| Phe | Cys | Leu | Ile | Leu | Trp | Lys | Trp | Lys | Lys | Lys | Lys | Arg | Pro | Arg | Asn | |
| | | | 260 | | | | | 265 | | | | | 270 | | | |
| tct | tat | aaa | tgt | gga | acc | aac | aca | atg | gag | agg | gaa | gag | agt | gaa | cag | 864 |
| Ser | Tyr | Lys | Cys | Gly | Thr | Asn | Thr | Met | Glu | Arg | Glu | Glu | Ser | Glu | Gln | |
| | | 275 | | | | | 280 | | | | | 285 | | | | |
| acc | aag | aaa | aga | gaa | aaa | atc | cat | ata | cct | gaa | aga | tct | gat | gaa | gcc | 912 |
| Thr | Lys | Lys | Arg | Glu | Lys | Ile | His | Ile | Pro | Glu | Arg | Ser | Asp | Glu | Ala | |
| 290 | | | | | 295 | | | | | 300 | | | | | | |
| cag | cgt | gtt | ttt | aaa | agt | tcg | aag | aca | tct | tca | tgc | gac | aaa | agt | gat | 960 |
| Gln | Arg | Val | Phe | Lys | Ser | Ser | Lys | Thr | Ser | Ser | Cys | Asp | Lys | Ser | Asp | |
| 305 | | | | 310 | | | | | 315 | | | | | 320 | | |
| aca | tgt | ttt | taa | | | | | | | | | | | | | 972 |
| Thr | Cys | Phe | * | | | | | | | | | | | | | |

<210> SEQ ID NO 16
<211> LENGTH: 323
<212> TYPE: PRT
<213> ORGANISM: Homo sapiens

<400> SEQUENCE: 16

Met Gly Leu Ser Asn Ile Leu Phe Val Met Ala Phe Leu Leu Ser Gly

```
                1               5                  10                 15
            Ala Ala Pro Leu Lys Ile Gln Ala Tyr Phe Asn Glu Thr Ala Asp Leu
                            20                  25                  30

Pro Cys Gln Phe Ala Asn Ser Gln Asn Gln Ser Leu Ser Glu Leu Val
                            35                  40                  45

Val Phe Trp Gln Asp Gln Glu Asn Leu Val Leu Asn Glu Val Tyr Leu
                50                  55                  60

Gly Lys Glu Lys Phe Asp Ser Val His Ser Lys Tyr Met Gly Arg Thr
            65                  70                  75                  80

Ser Phe Asp Ser Asp Ser Trp Thr Leu Arg Leu His Asn Leu Gln Ile
                            85                  90                  95

Lys Asp Lys Gly Leu Tyr Gln Cys Ile Ile His His Lys Lys Pro Thr
                            100                 105                 110

Gly Met Ile Arg Ile His Gln Met Asn Ser Glu Leu Ser Val Leu Ala
                            115                 120                 125

Asn Phe Ser Gln Pro Glu Ile Val Pro Ile Ser Asn Ile Thr Glu Asn
                130                 135                 140

Val Tyr Ile Asn Leu Thr Cys Ser Ser Ile His Gly Tyr Pro Glu Pro
            145                 150                 155                 160

Lys Lys Met Ser Val Leu Leu Arg Thr Lys Asn Ser Thr Ile Glu Tyr
                            165                 170                 175

Asp Gly Ile Met Gln Lys Ser Gln Asp Asn Val Thr Glu Leu Tyr Asp
                            180                 185                 190

Val Ser Ile Ser Leu Ser Val Ser Phe Pro Asp Val Thr Ser Asn Met
                            195                 200                 205

Thr Ile Phe Cys Ile Leu Glu Thr Asp Lys Thr Arg Leu Leu Ser Ser
                210                 215                 220

Pro Phe Ser Ile Glu Leu Glu Asp Pro Gln Pro Pro Asp His Ile
            225                 230                 235                 240

Pro Trp Ile Thr Ala Val Leu Pro Thr Val Ile Cys Val Met Val
                            245                 250                 255

Phe Cys Leu Ile Leu Trp Lys Trp Lys Lys Lys Arg Pro Arg Asn
                            260                 265                 270

Ser Tyr Lys Cys Gly Thr Asn Thr Met Glu Arg Glu Glu Ser Glu Gln
                275                 280                 285

Thr Lys Lys Arg Glu Lys Ile His Ile Pro Glu Arg Ser Asp Glu Ala
                            290                 295                 300

Gln Arg Val Phe Lys Ser Ser Lys Ser Thr Ser Ser Cys Asp Lys Ser Asp
            305                 310                 315                 320

Thr Cys Phe

<210> SEQ ID NO 17
<211> LENGTH: 690
<212> TYPE: DNA
<213> ORGANISM: Sus scrofa
<220> FEATURE:
<221> NAME/KEY: CDS
<222> LOCATION: (1)...(690)

<400> SEQUENCE: 17 atg tgc cac aca ctg aag tgg gga aca cca tta ccc aag ctc ttt cag     48
Met Cys His Thr Leu Lys Trp Gly Thr Pro Leu Pro Lys Leu Phe Gln
 1               5                  10                  15 ctc ttg gtg ctg gtt ggt ctt ttt gac ttc tgt tca ggc atc gtt cag     96
Leu Leu Val Leu Val Gly Leu Phe Asp Phe Cys Ser Gly Ile Val Gln
                 20                  25                  30
```

| | | | | | | | | | | | | | | | | |
|---|---|---|---|---|---|---|---|---|---|---|---|---|---|---|---|---|
| gtg | acc | aaa | aca | gtg | aaa | gaa | ata | gca | gtg | cta | tcc | tgt | gat | tac | aac | 144 |
| Val | Thr | Lys | Thr | Val | Lys | Glu | Ile | Ala | Val | Leu | Ser | Cys | Asp | Tyr | Asn | |
| | 35 | | | | 40 | | | | | 45 | | | | | | |
| ata | tcc | act | gaa | gaa | ctg | act | aga | gtc | cga | ata | tac | tgg | caa | aag | gat | 192 |
| Ile | Ser | Thr | Glu | Glu | Leu | Thr | Arg | Val | Arg | Ile | Tyr | Trp | Gln | Lys | Asp | |
| 50 | | | | | 55 | | | | | 60 | | | | | | |
| aat | gaa | atg | gtg | ctg | gct | gtc | atg | tct | gga | aaa | gtg | aag | gtg | tgg | ccc | 240 |
| Asn | Glu | Met | Val | Leu | Ala | Val | Met | Ser | Gly | Lys | Val | Lys | Val | Trp | Pro | |
| 65 | | | | 70 | | | | | 75 | | | | | 80 | | |
| aag | tat | gag | aac | cgc | acc | ttc | act | gat | gtc | acc | aat | aac | ctc | tgc | att | 288 |
| Lys | Tyr | Glu | Asn | Arg | Thr | Phe | Thr | Asp | Val | Thr | Asn | Asn | Leu | Cys | Ile | |
| | | | | 85 | | | | | 90 | | | | | 95 | | |
| gtg | atc | ctg | gct | ctg | cgc | ctg | tca | gac | aat | ggc | acc | tac | acc | tgt | gtt | 336 |
| Val | Ile | Leu | Ala | Leu | Arg | Leu | Ser | Asp | Asn | Gly | Thr | Tyr | Thr | Cys | Val | |
| | | | 100 | | | | | 105 | | | | | 110 | | | |
| gtt | cag | aag | cgg | gag | aga | ggg | tct | tat | aag | ctg | gag | cac | ctg | act | tcg | 384 |
| Val | Gln | Lys | Arg | Glu | Arg | Gly | Ser | Tyr | Lys | Leu | Glu | His | Leu | Thr | Ser | |
| | | 115 | | | | | 120 | | | | | 125 | | | | |
| gtg | aag | tta | atg | gtc | aaa | gct | gac | ttt | cct | gtg | cct | agt | att | act | gcc | 432 |
| Val | Lys | Leu | Met | Val | Lys | Ala | Asp | Phe | Pro | Val | Pro | Ser | Ile | Thr | Ala | |
| | 130 | | | | | 135 | | | | | 140 | | | | | |
| ctt | gga | aat | cca | tct | cct | aac | atc | aaa | agg | ata | agg | tgc | tca | acc | tct | 480 |
| Leu | Gly | Asn | Pro | Ser | Pro | Asn | Ile | Lys | Arg | Ile | Arg | Cys | Ser | Thr | Ser | |
| 145 | | | | | 150 | | | | | 155 | | | | | 160 | |
| gga | ggt | ttt | cca | gag | cct | cac | ctc | tcc | tgg | ttg | gaa | aat | gga | gaa | gaa | 528 |
| Gly | Gly | Phe | Pro | Glu | Pro | His | Leu | Ser | Trp | Leu | Glu | Asn | Gly | Glu | Glu | |
| | | | | 165 | | | | | 170 | | | | | 175 | | |
| tta | aat | gct | acc | aac | acg | atg | ctt | tcc | caa | gat | cct | gaa | act | gag | ctc | 576 |
| Leu | Asn | Ala | Thr | Asn | Thr | Met | Leu | Ser | Gln | Asp | Pro | Glu | Thr | Glu | Leu | |
| | | | 180 | | | | | 185 | | | | | 190 | | | |
| tac | atg | att | agc | agt | gaa | ctg | gat | ttc | aat | gtg | aca | ggc | aac | cac | agc | 624 |
| Tyr | Met | Ile | Ser | Ser | Glu | Leu | Asp | Phe | Asn | Val | Thr | Gly | Asn | His | Ser | |
| | | 195 | | | | | 200 | | | | | 205 | | | | |
| ttc | atg | tgt | ctt | gtc | aag | tat | gga | ggc | tta | aca | gtg | tca | cag | acc | ttc | 672 |
| Phe | Met | Cys | Leu | Val | Lys | Tyr | Gly | Gly | Leu | Thr | Val | Ser | Gln | Thr | Phe | |
| | 210 | | | | | 215 | | | | | 220 | | | | | |
| aac | tgg | caa | aaa | tgc | tga | | | | | | | | | | | 690 |
| Asn | Trp | Gln | Lys | Cys | * | | | | | | | | | | | |
| 225 | | | | | | | | | | | | | | | | |

```
<210> SEQ ID NO 18
<211> LENGTH: 229
<212> TYPE: PRT
<213> ORGANISM: Sus scrofa

<400> SEQUENCE: 18
```

Met Cys His Thr Leu Lys Trp Gly Thr Pro Leu Pro Lys Leu Phe Gln
1               5                   10                  15

Leu Leu Val Leu Val Gly Leu Phe Asp Phe Cys Ser Gly Ile Val Gln
            20                  25                  30

Val Thr Lys Thr Val Lys Glu Ile Ala Val Leu Ser Cys Asp Tyr Asn
        35                  40                  45

Ile Ser Thr Glu Glu Leu Thr Arg Val Arg Ile Tyr Trp Gln Lys Asp
    50                  55                  60

Asn Glu Met Val Leu Ala Val Met Ser Gly Lys Val Lys Val Trp Pro
65                  70                  75                  80

Lys Tyr Glu Asn Arg Thr Phe Thr Asp Val Thr Asn Asn Leu Cys Ile
                85                  90                  95

Val Ile Leu Ala Leu Arg Leu Ser Asp Asn Gly Thr Tyr Thr Cys Val
            100                 105                 110

```
Val Gln Lys Arg Glu Arg Gly Ser Tyr Lys Leu Glu His Leu Thr Ser
        115                 120                 125

Val Lys Leu Met Val Lys Ala Asp Phe Pro Val Pro Ser Ile Thr Ala
130                 135                 140

Leu Gly Asn Pro Ser Pro Asn Ile Lys Arg Ile Arg Cys Ser Thr Ser
145                 150                 155                 160

Gly Gly Phe Pro Glu Pro His Leu Ser Trp Leu Glu Asn Gly Glu Glu
                165                 170                 175

Leu Asn Ala Thr Asn Thr Met Leu Ser Gln Asp Pro Glu Thr Glu Leu
            180                 185                 190

Tyr Met Ile Ser Ser Glu Leu Asp Phe Asn Val Thr Gly Asn His Ser
        195                 200                 205

Phe Met Cys Leu Val Lys Tyr Gly Gly Leu Thr Val Ser Gln Thr Phe
    210                 215                 220

Asn Trp Gln Lys Cys
225

<210> SEQ ID NO 19
<211> LENGTH: 702
<212> TYPE: DNA
<213> ORGANISM: Homo sapiens
<220> FEATURE:
<221> NAME/KEY: CDS
<222> LOCATION: (1)...(702)

<400> SEQUENCE: 19 atg ggc cac aca cgg agg cag gga aca tca cca tcc aag tgt cca tac      48
Met Gly His Thr Arg Arg Gln Gly Thr Ser Pro Ser Lys Cys Pro Tyr
1               5                   10                  15 ctc aat ttc ttt cag ctc ttg gtg ctg gct ggt ctt tct cac ttc tgt      96
Leu Asn Phe Phe Gln Leu Leu Val Leu Ala Gly Leu Ser His Phe Cys
            20                  25                  30 tca ggt gtt atc cac gtg acc aag gaa gtg aaa gaa gtg gca acg ctg     144
Ser Gly Val Ile His Val Thr Lys Glu Val Lys Glu Val Ala Thr Leu
        35                  40                  45 tcc tgt ggt cac aat gtt tct gtt gaa gag ctg gca caa act cgc atc     192
Ser Cys Gly His Asn Val Ser Val Glu Glu Leu Ala Gln Thr Arg Ile
    50                  55                  60 tac tgg caa aag gag aag aaa atg gtg ctg act atg atg tct ggg gac     240
Tyr Trp Gln Lys Glu Lys Lys Met Val Leu Thr Met Met Ser Gly Asp
65                  70                  75                  80 atg aat ata tgg ccc gag tac aag aac cgg acc atc ttt gat atc act     288
Met Asn Ile Trp Pro Glu Tyr Lys Asn Arg Thr Ile Phe Asp Ile Thr
                85                  90                  95 aat aac ctc tcc att gtg atc ctg gct ctg cgc cca tct gac gag ggc     336
Asn Asn Leu Ser Ile Val Ile Leu Ala Leu Arg Pro Ser Asp Glu Gly
            100                 105                 110 aca tac gag tgt gtt gtt ctg aag tat gaa aaa gac gct ttc aag cgg     384
Thr Tyr Glu Cys Val Val Leu Lys Tyr Glu Lys Asp Ala Phe Lys Arg
        115                 120                 125 gaa cac ctg gct gaa gtg acg tta tca gtc aaa gct gac ttc cct aca     432
Glu His Leu Ala Glu Val Thr Leu Ser Val Lys Ala Asp Phe Pro Thr
    130                 135                 140 cct agt ata tct gac ttt gaa att cca act tct aat att aga agg ata     480
Pro Ser Ile Ser Asp Phe Glu Ile Pro Thr Ser Asn Ile Arg Arg Ile
145                 150                 155                 160 att tgc tca acc tct gga ggt ttt cca gag cct cac ctc tcc tgg ttg     528
Ile Cys Ser Thr Ser Gly Gly Phe Pro Glu Pro His Leu Ser Trp Leu
                165                 170                 175
```

```
gaa aat gga gaa gaa tta aat gcc atc aac aca aca gtt tcc caa gat    576
Glu Asn Gly Glu Glu Leu Asn Ala Ile Asn Thr Thr Val Ser Gln Asp
            180                 185                 190 cct gaa act gag ctc tat gct gtt agc agc aaa ctg gat ttc aat atg    624
Pro Glu Thr Glu Leu Tyr Ala Val Ser Ser Lys Leu Asp Phe Asn Met
        195                 200                 205 aca acc aac cac agc ttc atg tgt ctc atc aag tat gga cat tta aga    672
Thr Thr Asn His Ser Phe Met Cys Leu Ile Lys Tyr Gly His Leu Arg
    210                 215                 220 gtg aat cag acc ttc aac tgg aat aca tga                            702
Val Asn Gln Thr Phe Asn Trp Asn Thr *
225                 230
```

<210> SEQ ID NO 20
<211> LENGTH: 233
<212> TYPE: PRT
<213> ORGANISM: Homo sapiens

<400> SEQUENCE: 20

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr
225                 230